(12) United States Patent
Kang et al.

(10) Patent No.: US 10,802,283 B2
(45) Date of Patent: Oct. 13, 2020

(54) WEARABLE DEVICE AND METHOD FOR OUTPUTTING VIRTUAL IMAGE

(71) Applicant: Samsung Electronics Co., Ltd., Suwon-si, Gyeonggi-do (KR)

(72) Inventors: Seong-Woon Kang, Suwon-si (KR); Jae-Cheol Bae, Suwon-si (KR); Kwang-Dek An, Yongin-si (KR); In-Hak Na, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/238,058

(22) Filed: Jan. 2, 2019

(65) Prior Publication Data

US 2019/0137764 A1    May 9, 2019

Related U.S. Application Data

(63) Continuation of application No. 14/941,053, filed on Nov. 13, 2015, now Pat. No. 10,175,485.

(30) Foreign Application Priority Data

| Nov. 18, 2014 | (KR) | ........................ 10-2014-0161127 |
| Jul. 13, 2015 | (KR) | ........................ 10-2015-0099358 |

(51) Int. Cl.
*G02B 27/01* (2006.01)
*A61B 3/14* (2006.01)
(Continued)

(52) U.S. Cl.
CPC .......... *G02B 27/0172* (2013.01); *A61B 3/005* (2013.01); *A61B 3/0025* (2013.01);
(Continued)

(58) Field of Classification Search
CPC .... G02B 27/0172; G02B 6/00; G02B 27/017; G02B 3/0081; G02B 2027/0127;
(Continued)

(56) References Cited

U.S. PATENT DOCUMENTS

| 4,987,487 A | 1/1991 | Ichinose et al. |
| 2010/0013739 A1 | 1/2010 | Sko et al. |

(Continued)

FOREIGN PATENT DOCUMENTS

| CN | 101506868 A | 8/2009 |
| CN | 102937745 A | 2/2013 |

(Continued)

OTHER PUBLICATIONS

Extended European Search Report dated Nov. 2, 2017, issued in a counterpart European application No. 15860432.2-1666/3222037.
(Continued)

*Primary Examiner* — William R Alexander
*Assistant Examiner* — Henry A Duong
(74) *Attorney, Agent, or Firm* — Jefferson IP Law, LLP

(57) ABSTRACT

A wearable device and a method of outputting a virtual image by the wearable device area provided. The wearable device includes a projection type display unit that includes a variable lens and configured to project a light forming an image, a first sensor configured to detect a light reflected from an eye of a user, and a processor configured to control to display the virtual image on the projection type display unit by controlling one of a location of the variable lens and refractive power of the variable lens based on retina image information corresponding to the detected light.

19 Claims, 32 Drawing Sheets

(51) Int. Cl.
*A61B 3/12* (2006.01)
*A61B 3/00* (2006.01)
*A61B 3/11* (2006.01)
*A61B 3/103* (2006.01)
*G02B 3/00* (2006.01)
*G02B 6/00* (2006.01)
*H04N 13/122* (2018.01)

(52) U.S. Cl.
CPC .............. *A61B 3/103* (2013.01); *A61B 3/112* (2013.01); *A61B 3/12* (2013.01); *A61B 3/14* (2013.01); *G02B 3/0081* (2013.01); *G02B 6/00* (2013.01); *G02B 27/017* (2013.01); *G02B 2027/014* (2013.01); *G02B 2027/0118* (2013.01); *G02B 2027/0127* (2013.01); *G02B 2027/0138* (2013.01); *G02B 2027/0178* (2013.01); *G02B 2027/0187* (2013.01); *H04N 13/122* (2018.05)

(58) Field of Classification Search
CPC .... G02B 2027/0118; G02B 2027/0187; G02B 2027/0138; G02B 2027/014; G02B 2027/0178; G02B 27/01; G02B 27/0101; G02B 27/0103; G02B 27/0149; G02B 27/0176; G02B 27/0179; G02B 2027/0105; G02B 2027/0107; G02B 2027/0109; G02B 2027/011; G02B 2027/0112; G02B 2027/0114; G02B 2027/0116; G02B 2027/012; G02B 2027/0121; G02B 2027/0123; G02B 2027/0125; G02B 2027/0129; G02B 2027/0132; G02B 2027/0134; G02B 2027/0136; G02B 2027/0141; G02B 2027/0143; G02B 2027/0145; G02B 2027/0147; G02B 2027/015; G02B 2027/0152; G02B 2027/0154; G02B 2027/0156; G02B 2027/0158; G02B 2027/0159; G02B 2027/0161; G02B 2027/0163; G02B 2027/0165; G02B 2027/0167; G02B 2027/0183; G02B 2027/0185; G02B 2027/019; G02B 2027/0192; G02B 2027/0194; G02B 2027/0196; G02B 2027/0198; A61B 3/005; A61B 3/14; A61B 3/12; A61B 3/0025; A61B 3/112; A61B 3/103; H04N 13/122
USPC ........................................................ 359/630
See application file for complete search history.

(56) References Cited

U.S. PATENT DOCUMENTS

| | | |
|---|---|---|
| 2010/0202048 A1 | 8/2010 | Amitai et al. |
| 2012/0113092 A1 | 5/2012 | Bar-Zeev et al. |
| 2012/0254842 A1 | 10/2012 | Henderson |
| 2013/0207887 A1 | 8/2013 | Raffle et al. |
| 2013/0258486 A1* | 10/2013 | Ionescu .............. G02B 27/0172 359/630 |
| 2013/0278631 A1 | 10/2013 | Border et al. |
| 2013/0286053 A1 | 10/2013 | Fleck et al. |
| 2013/0286351 A1 | 10/2013 | Shimizu |
| 2013/0300634 A1 | 11/2013 | White et al. |
| 2014/0063206 A1 | 3/2014 | Chen et al. |
| 2014/0118829 A1 | 5/2014 | Ma et al. |
| 2014/0132485 A1 | 5/2014 | Kim et al. |
| 2014/0152698 A1 | 6/2014 | Kim et al. |
| 2014/0198297 A1 | 7/2014 | Bathiche et al. |
| 2015/0015814 A1 | 1/2015 | Qin |
| 2015/0061995 A1 | 3/2015 | Gustafsson et al. |
| 2016/0018639 A1 | 1/2016 | Spitzer et al. |
| 2016/0179193 A1* | 6/2016 | Du ........................ G06F 3/013 345/633 |

FOREIGN PATENT DOCUMENTS

| | | |
|---|---|---|
| CN | 103605208 A | 2/2014 |
| JP | 2006-195084 A | 7/2006 |
| JP | 2006-195665 A | 7/2006 |
| JP | 4973613 B2 | 4/2012 |
| KR | 10-1294914 B1 | 8/2013 |
| WO | 2006-0057227 A1 | 6/2006 |
| WO | 2013-159264 A1 | 10/2013 |

OTHER PUBLICATIONS

Chinese Office Action dated Jan. 22, 2018, issued in a counterpart Chinese application No. 201580062656.9.

* cited by examiner

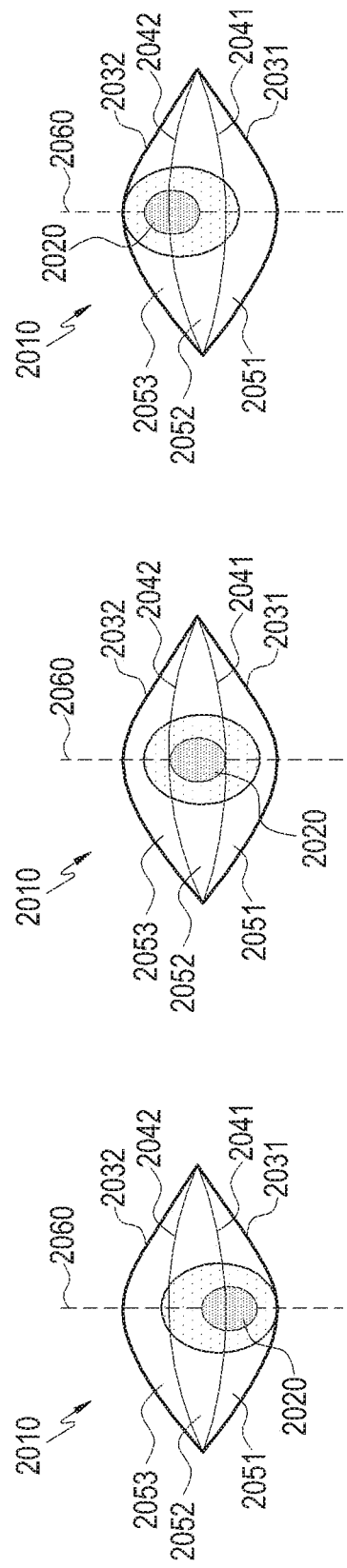

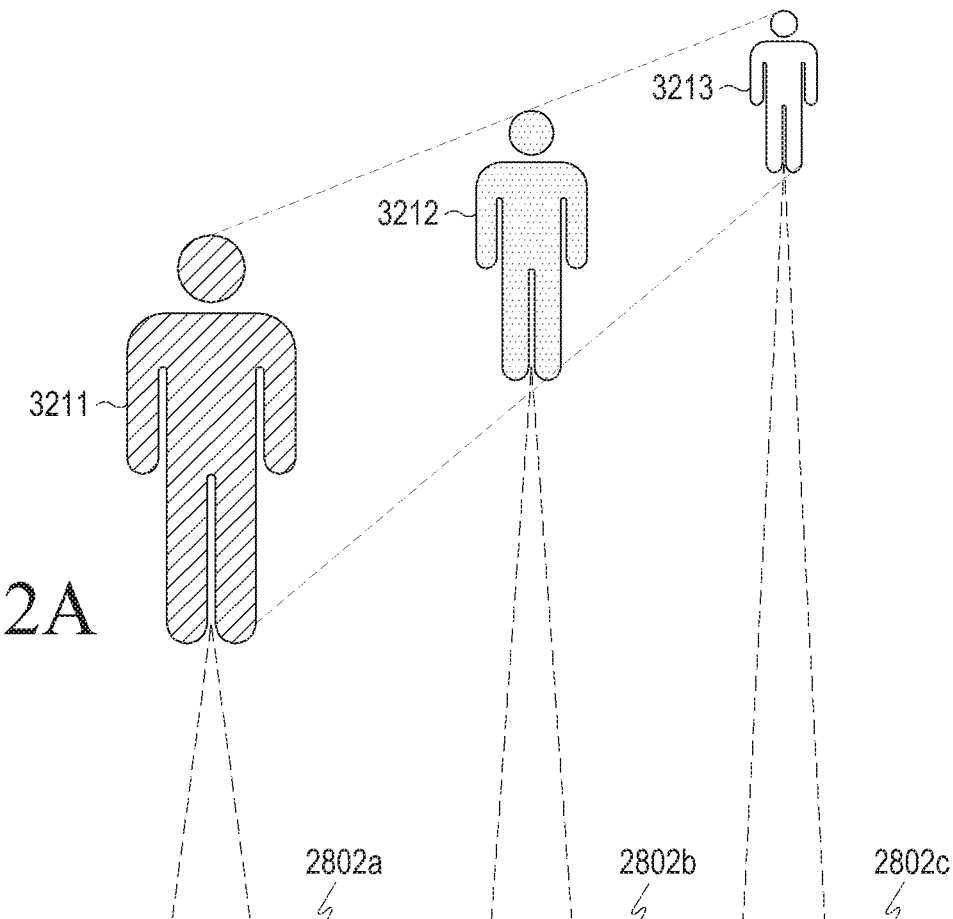
FIG.32A
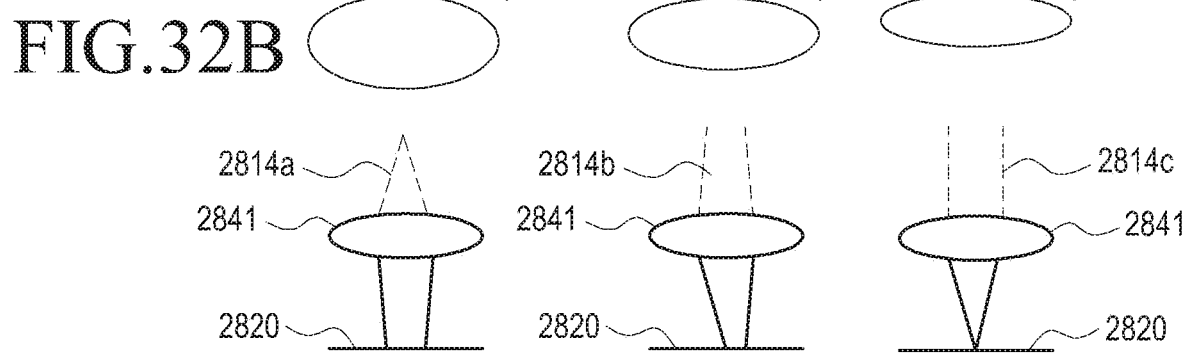
FIG.32B
FIG.32C
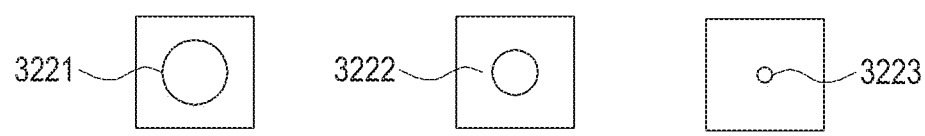
FIG.32D

WEARABLE DEVICE AND METHOD FOR OUTPUTTING VIRTUAL IMAGE

CROSS-REFERENCE TO RELATED APPLICATION(S)

This application is a continuation application of prior application Ser. No. 14/941,053, filed on Nov. 13, 2015, and was based on and claimed priority under 35 U.S.C. § 119(a) of a Korean patent application filed on Nov. 18, 2014 in the Korean Intellectual Property Office and assigned Serial number 10-2014-0161127, and under 35 U.S.C. § 119(a) of a Korean patent application filed on Jul. 13, 2015 in the Korean Intellectual Property Office and assigned Serial number 10-2015-0099358, the entire disclosure of each of which is hereby incorporated by reference.

TECHNICAL FIELD

The present disclosure relates to an electronic device including a projection type display unit (referred to as a projection type display device or a projector). More particularly, the present disclosure relates to a method and an apparatus for providing a virtual image by using a projection type display unit.

BACKGROUND

A wearable device may be divided into a video see-through type and an optical see-through type according to a structure of a display that outputs image information. The video see-through type corresponds to a type in which an image acquired through a camera and image information provided by a computer are combined and the combined image is provided to a user. Accordingly, the user recognizes surroundings only by means of the image acquired through the camera, so that the user may be cut off from an actual surrounding environment. The optical see-through type corresponds to a type in which a virtual image provided by the computer is projected onto the surrounding environment directly recognized by the user. Accordingly, the user may be in harmony with the surrounding environment.

When a user views an object through a wearable device, the user may feel dizzy and may complain of severe pain, since a depth of a projected image does not change according to a location (short, middle, or long distance) of an actual object even though depth information (or an object distance) on an actual image and depth information on the projected image are different.

Therefore, a need exists for a method and an apparatus for providing a virtual image by using a projection type display unit.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide a method and an apparatus for providing a virtual image to address the above described issues or other issues.

In accordance with an aspect of the present disclosure, a method of outputting a virtual image by a wearable device is provided. The method includes radiating a light to an eye of a user (or a wearer), acquiring retina image information by receiving a light which is reflected from the eye (or retina of the eye) of the user, calculating a focal length of a crystalline lens based on the acquired retina image information, and determining a viewing distance of the user based on the calculated focal length.

In accordance with another aspect of the present disclosure, a method of providing a virtual image is provided. The method includes photographing a retina image, calculating a focal length of the crystalline lens based on information on the photographed retina image, determined viewing distance information based on the calculated focal length of the crystalline lens, and displaying the virtual image by adjusting a location or refractive power of the variable lens based on the determined viewing distance information.

In accordance with another aspect of the present disclosure, a method of providing a virtual image by a wearable device including a projection type display unit is provided. The method includes projecting an illumination light to an eye of a user through an illumination unit (or the projection type display unit), detecting a light reflected from the eye (or retina of the eye), acquiring viewing distance information related to a viewing point (or focus) of the eye, and displaying the virtual image on the actual view through the projection type display unit to place the virtual image at a distance corresponding to the viewing point (or the viewing distance information).

In accordance with another aspect of the present disclosure, a method of providing a virtual image by a wearable device including a projection type display unit is provided. The method includes projecting an illumination light to an eye of a user through an illumination unit, detecting a light reflected from the eye (or retina of the eye) through a light receiving unit, adjusting a location or refractive power of a variable lens within the projection type display unit based on retina image information with respect to the detected light, and displaying the virtual image through a control of the projection type display unit.

In accordance with another aspect of the present disclosure, a method of providing a virtual image by a wearable device including a projection type display unit is provided. The method includes displaying a first virtual image on the actual view in the front of the wearable device through the projection type display unit, adjusting a location or refractive power of a variable lens within the projection type display unit, and displaying a second virtual image at a location farther or closer than a location of the first virtual image through the projection type display unit.

In accordance with another aspect of the present disclosure, a method of providing a virtual image by a wearable device is provided. The method includes acquiring information on a location of an eye feature point and/or information on a tilt of the wearable device, acquiring information on a distance between a preset reference point and a viewing point of the actual view based on the information on the location of the feature point and/or the information on the tilt of the wearable device, and displaying a virtual image on the actual view to place the virtual image at a virtual object distance corresponding to the information on the distance.

In accordance with another aspect of the present disclosure, a wearable device is provided. The wearable device includes a projection type display unit that includes a variable lens and configured to project a light forming an image, a first sensor configured to detect a light reflected from an eye of a user (or a wearer), and a processor configured to control the projection type display unit to display a virtual image by controlling one of a location of the variable lens and refractive power of the variable lens based on retina image information corresponding to the detected light.

In accordance with another aspect of the present disclosure, a wearable device is provided. The wearable device includes a projection type display unit configured to project a light forming an image, and a processor configured to project an illumination light onto an eye of a user, detect a light reflected from the eye (or retina of the eye), acquire viewing distance information related to a viewing point (or focus) of the eye based on retina image information with respect to the detected light, and display the virtual image (or first or second virtual image) on the actual view through the projection type display unit to place the virtual image at a distance corresponding to the viewing distance information.

In accordance with another aspect of the present disclosure, a wearable device is provided. The wearable device includes a projection type display unit configured to project a light forming an image, and a processor configured to project an illumination light onto an eye of a user, detect a light reflected from the eye (or retina of the eye), acquire viewing distance information related to a viewing point (or focus) of the eye based on retina image information with respect to the detected light, and display the virtual image (or first or second virtual image) on the actual view through the projection type display unit to place the virtual image at a distance corresponding to the viewing distance information.

In accordance with another aspect of the present disclosure, a wearable device is provided. The wearable device includes a projection type display unit configured to project an illumination light onto an eye of a user through an illumination unit, and a processor configured to detect a light reflected from the eye (or retina of the eye) through a light receiving unit, adjust a location or refractive power of a variable lens within the projection type display unit based on retina image information with respect to the detected light, and display the virtual image through a control of the projection type display unit.

In accordance with another aspect of the present disclosure, a wearable device is provided. The wearable device includes a projection type display unit configured to project a light forming an image, and a processor configured to display a first virtual image on the actual view in the front of the wearable device through the projection type display unit, project an illumination light onto an eye of a user through the projection type display unit, detect a light reflected from the eye (or retina of the eye) through the projection type display unit, adjust a location or refractive power of a variable lens within the projection type display unit based on retina image information with respect to the detected light, and display a second virtual image at a location farther or closer than a location of the first virtual image through the projection type display unit.

In accordance with another aspect of the present disclosure, a wearable device is provided. The wearable device includes a projection type display unit configured to project a light forming an image, and a processor configured to display a first virtual image on the actual view in the front of the wearable device through the projection type display unit, adjust a location or refractive power of a variable lens within the projection type display unit, and displaying a second virtual image at a location farther or closer than a location of the first virtual image through the projection type display unit.

In accordance with another aspect of the present disclosure, a wearable device is provided. The wearable device includes a projection type display unit configured to project a light forming an image, and a processor configured to acquire information on a location of an eye feature point and/or information on a tilt of the wearable device, acquire information on a distance between a preset reference point and a viewing point of the actual view based on the information on the location of the feature point and/or the information on the tilt of the wearable device, and display a virtual image on the actual view to place the virtual image at a virtual object distance corresponding to the information on the distance.

According to various embodiments of the present disclosure, the user of the electronic device may not feel dizzy by projecting a short distance image when the user views a short distance object, projecting a middle distance image when the user views a middle distance object, and projecting a long distance image when the user views a long distance object.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 20A, 20B, and 20C illustrate a method of providing a virtual image according to various embodiments of the present disclosure;

FIGS. 32A, 32B, 32C, and 32D illustrate a method of providing a virtual image according to an embodiment of the present disclosure;

Throughout the drawings, it should be noted that like reference numbers are used to depict the same or similar elements, features, and structures.

DETAILED DESCRIPTION

Figure 1:
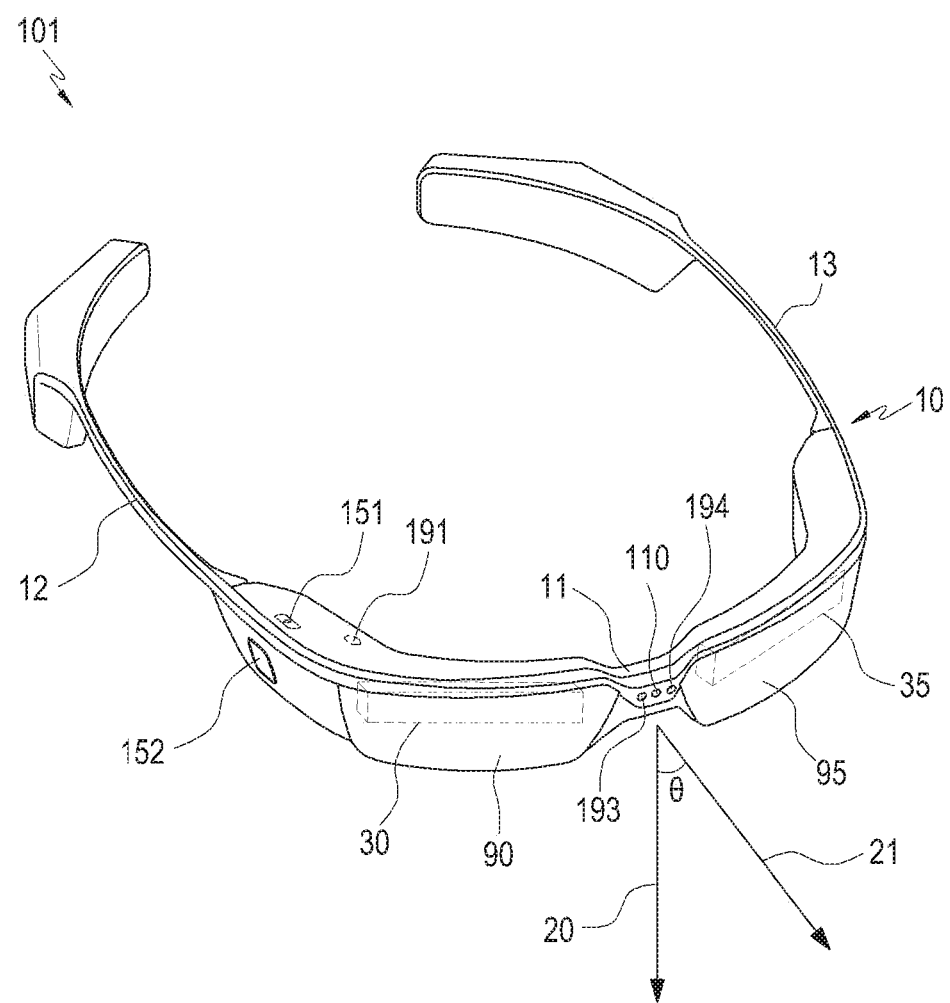
FIG. 1 is a perspective view illustrating a wearable device according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the expression "have", "may have", "include", or "may include" refers to the existence of a corresponding feature (for example, a numeral, a function, an operation, or a constituent element, such as a component), and does not exclude one or more additional features.

As used herein, the expression "A or B", "at least one of A and/or B", or "one or more of A and/or B" may include any or all possible combinations of items enumerated together. For example, the expression "A or B", "at least one of A and B", or "at least one of A or B" may include (1) at least one A, (2) at least one B, or (3) both at least one A and at least one B.

The expression "a first", "a second", "the first", or "the second" used in various embodiments of the present disclosure may modify various components regardless of the order and/or the importance but does not limit the corresponding components. The above expressions are used merely for the purpose of distinguishing an element from the other elements. For example, a first user device and a second user device indicate different user devices although both of them are user devices. For example, a first element may be termed a second element, and similarly, a second element may be termed a first element without departing from the scope of the present disclosure.

When it is mentioned that one element (for example, a first element) is "(operatively or communicatively) coupled with/to or connected to" another element (for example, a second element), it should be construed that the one element is directly connected to the another element or the one element is indirectly connected to the another element via yet another element (for example, a third element). In contrast, it may be understood that when an element (for example, a first element) is referred to as being "directly connected," or "directly coupled" to another element (e.g., a second element), there are no element for example, a third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (for example, an embedded processor) only for performing the corresponding operations or a generic-purpose processor (for example, a central processing unit (CPU) or an application processor (AP)) that can perform the corresponding operations by executing one or more software programs stored in a memory device.

The terms used herein are merely for the purpose of describing particular embodiments and are not intended to limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary are to be interpreted to have the meanings equal to the contextual meanings in the relevant field of the art, and are not to be interpreted to have ideal or excessively formal meanings unless clearly defined in the present disclosure. In some cases, even the term defined in the present disclosure should not be interpreted to exclude embodiments of the present disclosure.

Hereinafter, an electronic device according to various embodiments will be described with reference to the accompanying drawings. As used herein, the term "user" may indicate a person who uses an electronic device or a device (for example, an artificial intelligence electronic device) that uses an electronic device.

FIG. 1 is a perspective view illustrating a wearable device according to an embodiment of the present disclosure.

Referring to FIG. 1, a wearable device 101 may have an overall appearance of glasses, and may be referred to as a wearable electronic device, an electronic device, a portable terminal, a mobile terminal, a wearable type device, a display device, smart glasses, or the like.

The wearable device 101 may include a housing 10, first and second windows 90 and 95, first and third sensors 191 and 193, a power button 151, a touch sensor 152, and first and second light guide units 30 and 35.

The housing 10 may include some components of the wearable device 101 therein, and some components of the wearable device 101 may be mounted to the housing 10 to be exposed to the outside.

The housing 10 may include a front frame 11, to which the first and second windows 90 and 95 facing a user's right and left eyes are fixed, and first and second temple frames 12 and 13 extending from both ends of the front frame 11. The user's right and left eyes may be referred to as first and second eyes. The first and second windows 90 and 95 may be referred to as first and second glasses.

The first sensor 191, a camera module 110, and an illumination sensor 194 may be disposed on a rear surface and a front surface of the front frame 11, and the power button 151 and the touch sensor 152 may be further disposed on an upper surface and a side surface of the front frame 11.

The first sensor 191 may be disposed on the rear surface of the front frame 11 to face the user's eyes, and may radiate an illumination light (for example, an infrared light or laser) to the user's eyes and detect the illumination light reflected from the user's eyes. The first sensor 191 may output images generated by photographing the user's eyes to a processor of the wearable device 101.

The illumination sensor 194 detects an amount of the ambient light of the wearable device 101. Further, the illumination sensor 194 may transmit an illumination signal corresponding to the detected illumination (or brightness) to the processor 120 according to a control of the processor 120.

According to an embodiment of the present disclosure, the first sensor 191 may include an illumination unit (or an light source or a light emitting unit) for projecting the illumination light into the user's eye, and a light receiving unit for detecting the light reflected from the eye (or retina of the eye). The first sensor 191 may output a signal/data (for example, an image) indicating the reflected light to the processor 120. For example, the first sensor 191 may detect the reflected light in the form of an image and output the image to the processor 120.

According to an embodiment of the present disclosure, the processor 120 may calculate an amount of the light detected by the illumination sensor 194 to determine the size of pupils and may calculate viewing distance information related to a viewing point of the eye. The viewing point may refer to a point or an object on an actual view at which the user is looking.

According to an embodiment of the present disclosure, the processor 120 may acquire the viewing distance information related to the viewing point (or focus) of the eye based on retina image information with respect to the detected light (or image of the detected light). The processor 120 may display a virtual image on an actual view (or an optical image of the view) to place the virtual image at a distance corresponding to the viewing distance information.

According to an embodiment of the present disclosure, the processor 120 drives a light receiving unit (camera) by outputting a driving signal to the light receiving unit. When the light reflected from the retina among the illumination light projected toward the pupils penetrates a lens and an aperture of the light receiving unit and reaches an image sensor (for example, a charge-coupled device (CCD) or a complementary metal-oxide semiconductor CMOS) of the light receiving unit, information on an intensity of the light incident to the lens and an area of the image is recorded in the image sensor. At this time, the light of the image photographed by the image sensor may be converted into an electrical signal by a photosensitive element included in the image sensor. The photographed image is generated by the image sensor using the converted electrical signal. At this time, the retina image information (for example, retina reflective surface size information or pixel information on an image signal processor (ISP) sensor or the image sensor) acquired by photographing the light reflected from the retina may include at least one piece of size information, area information, location information, pattern information and brightness (or brightness distribution) on the photographed image. For example, each piece of the information may include a corresponding value, a corresponding range, or a corresponding level (or an identifier/code indicating one of them). Further, the light receiving unit may be one of an infrared camera and a visible light camera.

According to an embodiment of the present disclosure, the viewing distance information may include at least one piece of distance measurement information using a third sensor (for example, the third sensor 193), object distance information calculated based on focal length information on the crystalline lens, size information on the retina reflective surface (that is, some areas of the retina where the illumination light is incident and reflected) calculated based on the retina image information (that is, defocus size), magnification information, refractive power information, curvature (or radius of curvature) information, and thickness information on the crystalline lens.

For example, each piece of the information may include a corresponding value, a corresponding range, or a corresponding level (or an identifier/code indicating one of them).

Figure 16:
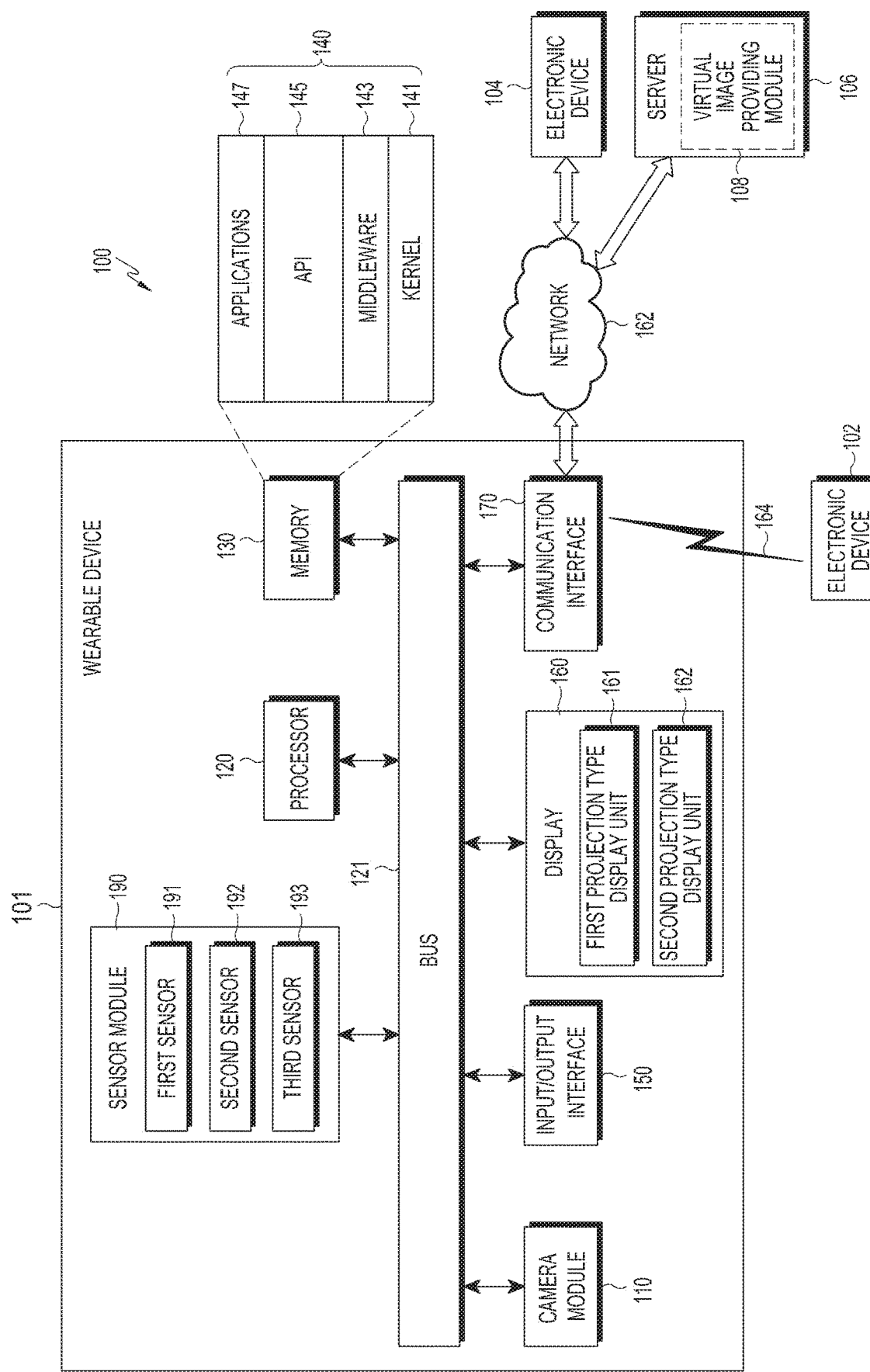
FIG. 16 illustrates a network environment including an electronic device according to an embodiment of the present disclosure.

According to an embodiment of the present disclosure, at least some of the first sensor 191 may be disposed outside or inside first and/or second projection type display units 161 and 162 of FIG. 16 and may be included in the first and/or second projection type display units 161 and 162 of FIG. 16.

The third sensor 193 is disposed on the front surface of the front frame 11 frontward (i.e., to face forward), and may radiate an infrared light or laser forward from the wearable device 101 and detect the infrared light or laser reflected from an actual object. The third sensor 193 may output a detection signal indicating a distance between the third sensor 193 and the actual object to the processor of the wearable device 101.

The camera module 110 is disposed on the front surface of the front frame 11 to face forward and may output an image generated by photographing a front view (that is, a front surrounding scene or surrounding environment) of the wearable device 101 to the processor.

Each of the first sensor 191 and the camera module 110 may include a lens system and an image sensor. Each of the first sensor 191 and the camera module 110 may convert the light received (or photographed) through the lens system into an electrical image signal and output the converted signal to the processor. Each of the first sensor 191 and the camera module 110 may photograph a dynamic image or a still image. The camera module 110 may be provided to receive a user input by a user's motion or gesture.

The lens system may form an image of a subject for photography by making the light received from the outside converge. The lens system includes one or more lenses, and each lens may be a convex lens, an aspheric lens, or the like. The lens system may have symmetry based on an optical axis passing the center, and the optical axis may be defined as the center axis. The image sensor may detect an optical image formed by the external light received through the lens system as an electrical image signal. The image sensor may include a plurality of pixel units which are aligned in a matrix structure of M×N, and the pixel units may include a photodiode and a plurality of transistors. The pixel unit may accumulate electric charges generated by the received light and a voltage by the accumulated electric charges may indicate illumination (or brightness) of the received light. When one image included in a still image or a dynamic image is processed, the image signal output from the image sensor may include a set of voltages (that is, pixel value) output from the pixel units and the image signal may indicate one frame (that is, still image). Further, the frame may consist of M×N pixels. A CCD image sensor or a CMOS image sensor may be employed as the image sensor.

The image sensor may operate all pixels of the image sensor or only pixels in an area of interest among all the pixels according to a control signal received from the processor, and image data output from the pixels may be output to the processor.

The power button 151 may be disposed on a top surface of the front frame 11, and the wearable device 101 may be turned on/off by a user input through the power button 151.

The touch sensor 152 may be disposed on the side surface of the front frame 11, and may detect at least one touch/hovering input and transmit input information to the processor. For example, the user may touch the touch sensor 152 through a user's body part (for example, a finger) or other touch means (for example, an electronic pen), and the touch sensor 152 may receive the user's touch input. Further, the touch sensor 152 may receive an input (that is, a swipe/drag input) according to successive touch motions. Touch input information may include a touch coordinate and/or a touch state. The touch state may be a state in which the touch sensor 152 is pressed, a state in which the finger is separated from the touch sensor 152, or a drag state in which sliding is made while the touch sensor 152 is pressed. The processor may detect user input information, such as selection or movement of a menu item or an item or a writing input from the touch input information and perform a function (for example, call connection, camera photography, message writing/viewing, and/or data transmission) corresponding to the user input information.

A touch is not limited to a contact between the touch sensor 152 and a touch input means and may include non-contact (for example, when the touch sensor 152 and the touch input means are separated from each other). The non-contact touch input may be referred to as a hovering input. The touch sensor 152 may be implemented by a resistive type, a capacitive type, an infrared type, an acoustic wave type, an electromagnetic resonance (EMR) type, or a combination thereof.

The touch sensor 152 may have a fingerprint detection function, and may generate fingerprint information corresponding to a fingerprint pattern of the finger when the user's finger contacts the surface of the touch sensor 152. Further, the touch sensor 152 may have a switch structure and generate press detection data according to the press by the user. The touch sensor 152 may output the generated fingerprint data and/or press detection data to the processor. Alternatively, the touch sensor 152 may generate fingerprint input direction data by detecting a user's fingerprint input direction and output the generated fingerprint input direction data to the processor. For example, fingerprint information may include fingerprint pattern information and fingerprint input direction information.

The processor may recognize a user's fingerprint from the fingerprint information received from the touch sensor 152. The processor may map at least one fingerprint and at least one executable function or a user and store the mapped information in a memory of the wearable device 101. Further, the memory may store pre-registered user fingerprint information, and the processor may search for fingerprint information, which matches the fingerprint information received from the touch sensor 152, in the memory and determine a user or a function mapped to the found fingerprint information. When a function is mapped to the found fingerprint information, the processor may execute the mapped function.

The executable function may be an unlock function, an application execution function, a user account change function, a multimedia control function, and/or the like.

The unlock function may correspond to a function of unlocking the wearable device 101 through a fingerprint input. For example, when a user input is not received for a certain time, the processor may restrict the execution of the function of the wearable device 101. The unlock function is a function of releasing the restriction of the execution of the function. The application execution function may correspond to a function of executing a game application, an SNS application, a document writing application, a multimedia application, or the like, or a function of automatically making a connection to a preset contact by a phone call application, a message application, or the like. The user account change function may correspond to a function of selecting one of a plurality of user accounts. The multimedia control function may correspond to a function of displaying a control menu, such as a volume control menu or a play menu, a function of controlling a volume, such as a volume increase, a volume decrease, or mute, or a function of controlling multimedia, such as rewind, fast forward, pause, or play.

The first light guide unit 30 may be included in the first projection type display unit and disposed between the user's right eye and the first window 90, and may project the light forming an image into the right eye.

The second light guide unit 35 may be included in the second projection type display unit and disposed between the user's left eye and the second window 95, and may project the light forming an image into the left eye.

Since the first and second projection type display units have the same configuration, the configuration of the first projection type display unit will be representatively described below. Further, the projection type display unit may be referred to as a projector.

According to an embodiment of the present disclosure, the wearable device 101 may include only one of the first and second projection type display units, and the first sensor 191 may be included in one of the first and second projection type display units or separately provided.

According to an embodiment of the present disclosure, at least one of the first and second projection type display units and/or the first sensor 191 may be fixed to the wearable device 101 or may be provided in the form of a removable module which can be mounted and separated.

According to an embodiment of the present disclosure, the wearable device 101 may be fixed to glasses or may be provided in the form of a removable module which can be mounted and separated.

Figure 2:
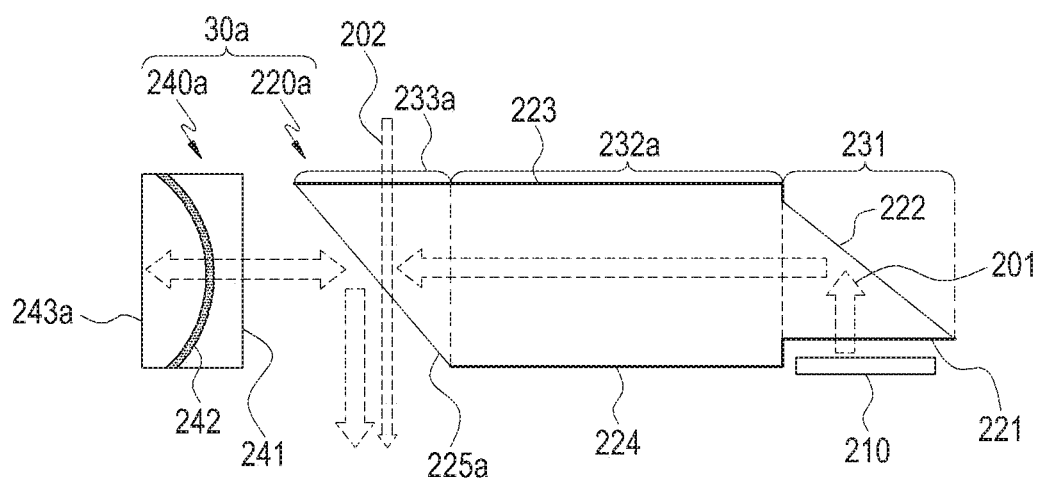
FIG. 2 illustrates a first projection type display unit according to an embodiment of the present disclosure.

FIG. 2 illustrates a first projection type display unit according to an embodiment of the present disclosure.

Referring to FIG. 2, a first projection type display unit 161a may include a display element 210 and a light guide unit 30a. The light guide unit 30a may include a light guide element 220a and a variable lens 240a. Similarly, the second projection type display unit may include a display element and a light guide unit, and the light guide unit may include a light guide element and a variable lens.

The display element 210 may output a first light 201 forming an image to the light guide element 220a. The display element 210 may have the form of a quadrangular flat panel. The display element 210 may display an image in the unit of pixels according to data input from the processor. The display element 210 may include pixel elements corresponding to the preset resolution and display an image by driving the pixel elements. For example, the display element 210 may include pixel elements arranged in an M×N (for example, 1190×720, 854×480, and the like) matrix structure. The display element 210 may be a light emitting diode (LED), an organic light emitting diode (OLED), a liquid crystal display (LCD), a liquid crystal on silicon (LCOS), or the like.

The light guide element 220a may include first to fifth surfaces 221 to 225a. The light guide element 220a may guide the first light 201 received from the display element 210 through internal reflection (or internal total reflection) toward the variable lens 240a.

The first surface 221 may correspond to a part of the rear surface of the light guide element 220a facing the display element 210, and may allow the first light 201 received from the display element 210 to pass therethrough toward the second surface 222.

The second surface 222 corresponds to a first side surface of the light guide element 220a located between the first surface 221 and a third surface 223, and may reflect the first light 201 having penetrated the first surface 221 toward the third surface 223 or a fourth surface 224.

The third surface 223 corresponds to the front surface of the light guide element 220a facing the first window 90, the fourth surface 224 corresponds to the remaining part of the rear surface of the light guide element 220a facing the user, and the third and fourth surface 223 and 224 may reflect (or totally reflect) the received first light 201 to make the first light 201 reach the fifth surface 225a. The total reflection means that the first light 201 received by a boundary surface between the light guide element 220a and an external air layer (that is, the third or fourth surface 223 or 224) from the inside of the light guide element 220 is totally reflected from the boundary surface.

The fifth surface 225a corresponds to a second side surface of the light guide element 220a located between a third surface 223a and the fourth surface 224, and may allow the received first light 201 to pass therethrough toward the variable lens 240a and reflect the first light 201 received from the variable lens 240a toward the user's eye. The fifth surface 225a may allow a second light 202 forming a front view (or an optical image of the view) of the wearable device 101 to pass therethrough toward the user's eye.

The light guide element 220a may include a body part 232a between the third and fourth optical surfaces 223 and 224 having a uniform thickness, a first inclined part 231 between the first and second surfaces 221 and 222, of which the thickness gradually decrease from one end thereof (or from one end of the body part 232a) to the other end thereof, and a second inclined part 233a between the third and fourth surfaces 223 and 224, of which the thickness gradually decrease from one end thereof (or from the other end of the body part 232a) to the other end thereof. The second inclined part 233a may have the fifth surface 225a corresponding to a slope which faces the variable lens 240a and the user's eye.

The variable lens 240a may include a penetration surface 241 for allowing the received first light 201 to pass therethrough, a refraction surface 242 for refracting the received first light 201, and a reflection surface 243a for reflecting the received first light 201. A shape (or form) or curvature of the refraction surface 242 may vary according to a control of the processor. The variable lens 240a may control a location (or a virtual object distance between the user's eye and a virtual object) of a virtual image displayed on an actual view (or an optical image of the view) in the front of the wearable device (for example, the wearable device 101) by adjusting an angle of the first light 201 (that is, an incident light) incident to the user's eye according to a change in the shape (or form) or curvature of the refraction surface 242.

Figure 3A:
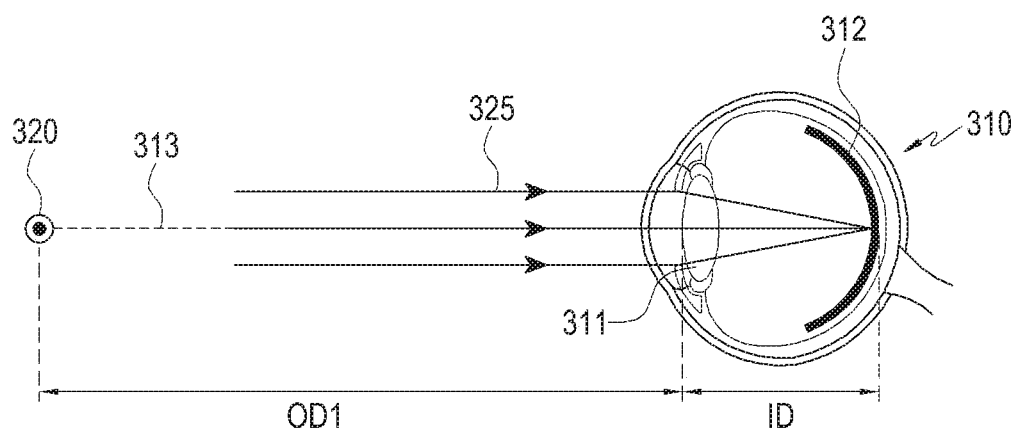
FIGS. 3A and 3B illustrate controlling eye focus according to various embodiments of the present disclosure.
Figure 3B:
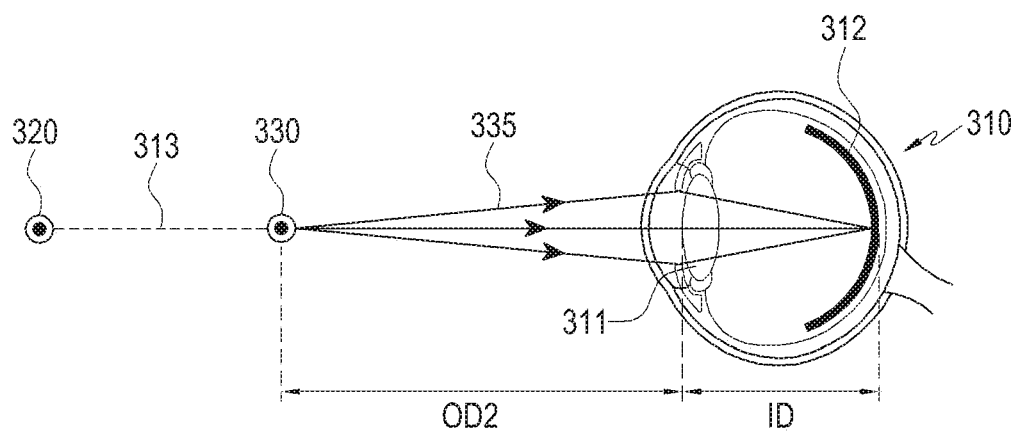

FIGS. 3A and 3B illustrate controlling eye focus according to various embodiments of the present disclosure.

Referring to FIGS. 3A and 3B, an eye 310 of the user includes a crystalline lens 311 and a retina 312.

The crystalline lens 311 changes a curvature of the surface thereof (each of the front surface and the rear surface) according to a distance of an object (that is, object distance)

which crystalline lens 311 desires to focus. The eye focuses on a long distance object when the crystalline lens 311 changes to be thin (that is, when the curvature of the surface is small), and focuses on a short distance object when the crystalline lens 311 changes to be thick (that is, when the curvature of the surface is large).

Referring to FIG. 3A, the crystalline lens 311 changes to be thin (or the curvature of the surface decreases) and the eye 310 focuses on a long distance object 320. A light 325 starting from the long distance object 320 progresses in parallel to an optical axis of the eye 310 to be incident to the crystalline lens 311, and the crystalline lens 311 refracts the light 325 to make the light 325 converge on the retina 312. For example, the crystalline lens 311 serves to form an image of the long distance object 320 on the retina 312. For example, when the long distance object 320 (or the image of the object) is in focus (that is, in focus state), a distance of the long distance object from the crystalline lens 311 may be referred to as a first object distance (OD1) and a distance of the retina 312 from the crystalline lens 311 may be referred to as an image distance (ID). The object distance and the ID may be distances measured along the optical axis of the eye.

Referring to FIG. 3B, the crystalline lens 311 changes to be thick (or the curvature of the surface increases) and the eye 310 focuses on a short distance object 330. A light 335 starting from the short distance object 330 diverges (or diffuses) along the optical axis 313 of the eye 310 to be incident to the crystalline lens 311, and the crystalline lens 311 refracts the light 335 to make the light 335 converge on the retina 312. For example, the crystalline lens 311 serves to form an image of the short distance object 330 on the retina. For example, when the short distance object (or the image of the short distance object) is in focus, a distance of the short distance object 330 from the crystalline lens 311 may be referred to as a second object distance (OD2) and a distance of the retina 312 from the crystalline lens 311 may be referred to as an ID.

Since the crystalline lens changes and focuses according to the distance of the object, the ID is constant and the object distance changes in an in focus state according to a change in the distance of the object.

An object shown by the user's eye may be an actual object or a virtual object (for example, an image on the display element).

When the eye focuses the short distance object, an image of the short distance object is formed clearly (that is, in focus state) and an image of the long distance object is formed blurredly (that is, out of focus state).

In contrast, when the eye focuses on the long distance object, the image of the long distance object is formed clearly (that is, in focus state) and the image of the short distance object is formed blurredly (that is, out of focus).

For example, when a long distance actual object and a short distance virtual object, which displays information on the actual object, overlap each other, concentration on an augmented reality may deteriorate or the user may feel dizzy.

Figure 4A:
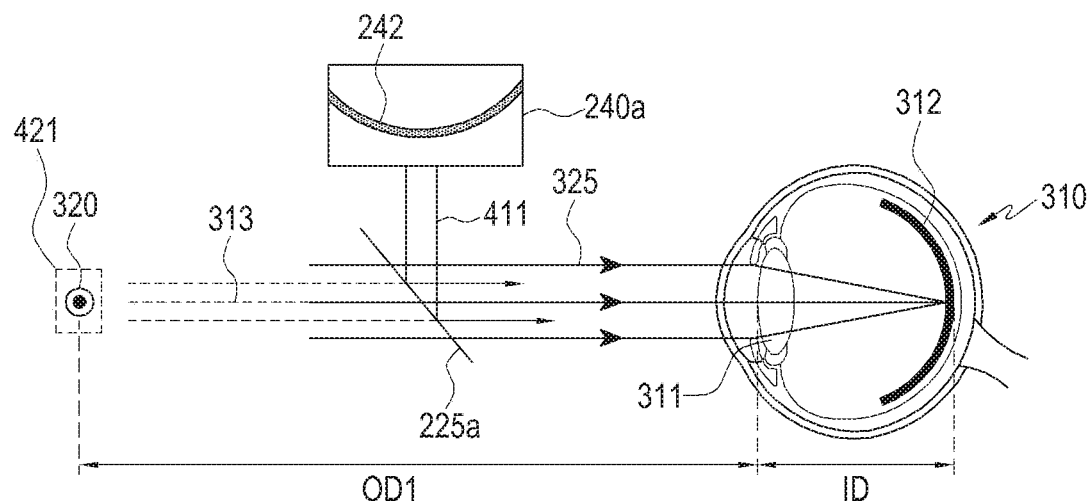
FIGS. 4A and 4B illustrate adjusting a virtual object distance by a variable lens according to various embodiments of the present disclosure.
Figure 4B:
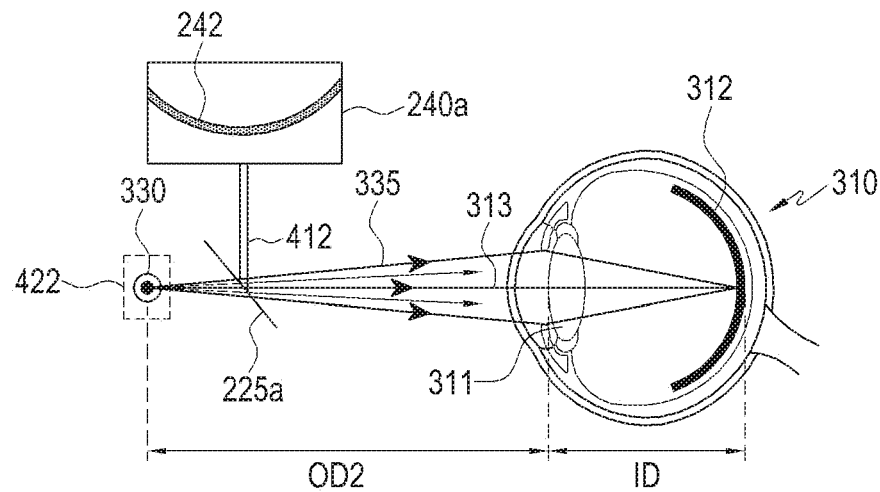

FIGS. 4A and 4B illustrate adjusting a virtual object distance by a variable lens according to various embodiments of the present disclosure.

Referring to FIGS. 4A and 4B, the variable lens 240a may control a location of the virtual image (or a virtual object distance between the user's eye 310 and a virtual object 421 recognized by the user) displayed on an actual view (or an optical image of the view) in the front of the wearable device (for example, the wearable device 101) by adjusting an incident angle of a first light 411 incident to the user's eye 310 according to a control of the variable lens 240a.

Referring to FIG. 4A, the crystalline lens 311 changes to be thin and the eye focuses on the long distance actual object 320. A second light 325 starting from the long distance actual object 320 progresses in parallel to the optical axis 313 of the eye 310 and penetrates the fifth surface 225a of the light guide element 220a to be incident to the crystalline lens 311, and the crystalline lens 311 refracts the second light 325 to make the second light 325 converge on the retina 312. For example, the crystalline lens 311 serves to form an image of the actual object 320 on the retina.

The variable lens 240a may project the first light 411 onto the fifth surface 225a. The first light 411 reflected from the fifth surface 225a progresses in parallel to the optical axis 313 of the eye 310 to be incident to the crystalline lens 311, and the crystalline lens 311 refracts the first light 411 to make the first light 411 converge on the retina 312. For example, the crystalline lens 311 serves to form an image of the virtual object 421 on the retina. For example, when the actual object 320 (or the image of the actual object 320) is in focus, the actual object 320 (or the image of the actual object 320) and the virtual object 421 (or the image of the virtual object 421) may have the same OD1 and the same ID.

Referring to FIG. 4B, the crystalline lens 311 changes to be thick and the eye focuses on the short distance actual object 330. The second light 335 starting from the short distance actual object 330 progresses while diverging (or diffusing) along the optical axis 313 of the eye 310 and penetrates the fifth surface 225a of the light guide element 220a to be incident to the crystalline lens 311, and the crystalline lens 311 refracts the second light 335 to make the second light 335 converge on the retina 312. For example, the crystalline lens 311 serves to form the image of the actual object 330 on the retina 312. The variable lens 240a may project the first light 412 onto the fifth surface 225a. The first light 412 reflected from the fifth surface 225a progresses while diverging (or diffusing) along the optical axis 313 of the eye 310 to be incident to the crystalline lens 311, and the crystalline lens 311 refracts the first light 412 to make the first light 412 converge on the retina 312. For example, the crystalline lens 311 serves to form the image of the virtual object 422 on the retina 312. For example, when the actual object 330 (or the image of the actual object 330) is in focus, the actual object 330 (or the image of the actual object 330) and the virtual object 422 (or the image of the virtual object 422) may have the same OD2 and the same ID.

Figure 5A:
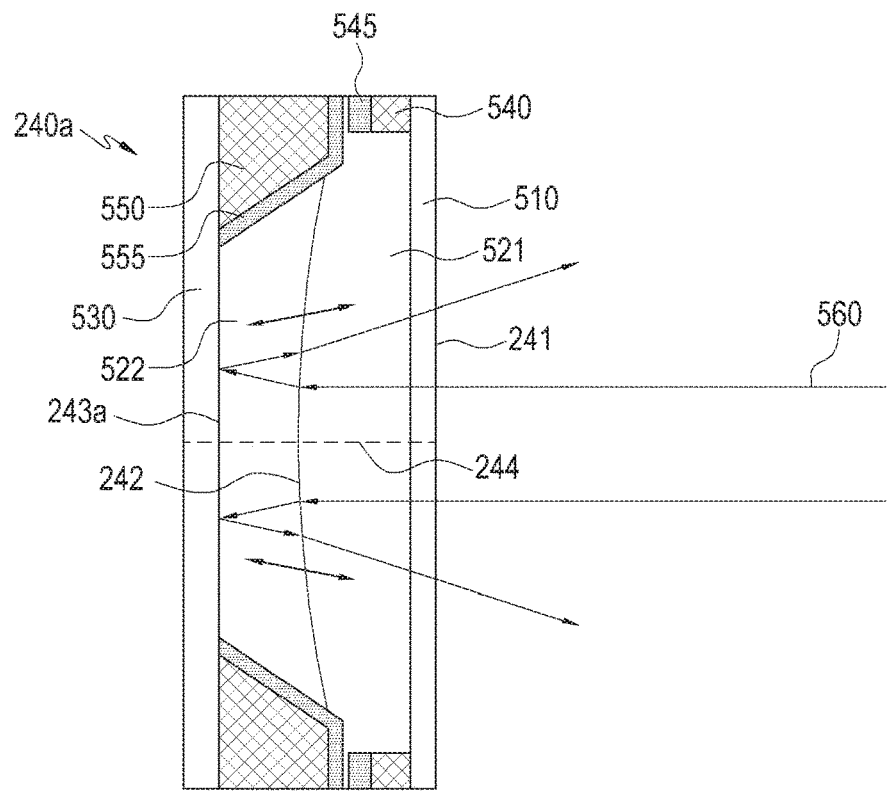
FIGS. 5A and 5B illustrate a variable lens according to various embodiments of the present disclosure.
Figure 5B:
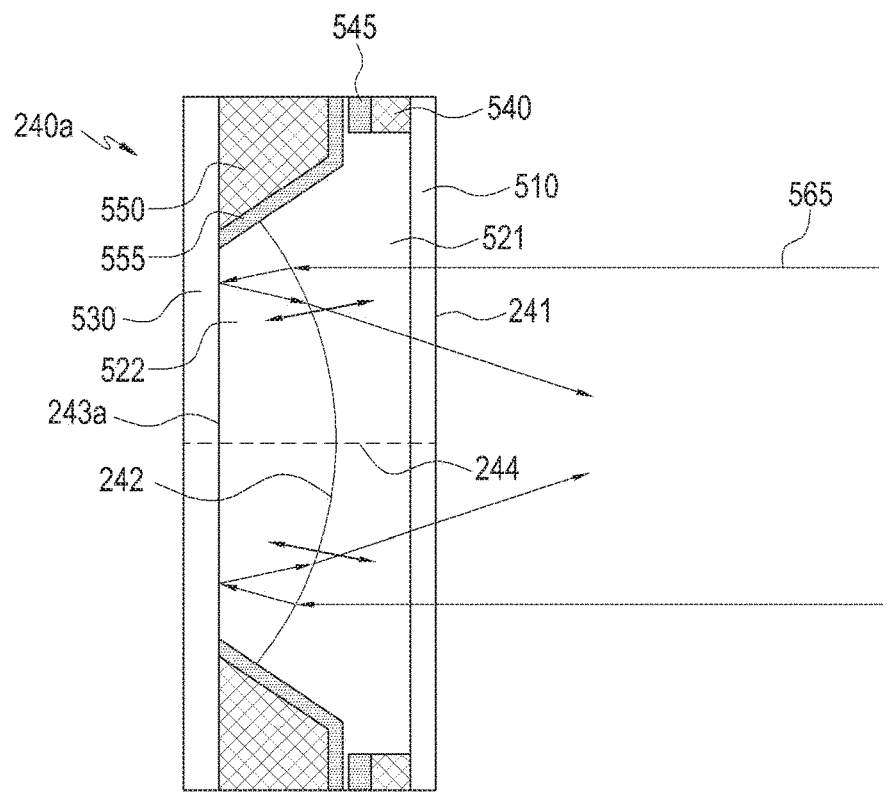

FIGS. 5A and 5B illustrate a variable lens according to various embodiments of the present disclosure.

Referring to FIG. 5A, the variable lens 240a may include first and second substrate 510 and 530, first and second electrodes 540 and 550, and first and second liquids 521 and 522.

The first substrate 510 may be a transparent flat panel, and may allow a first light 560 received from the light guide element 220a to pass therethrough. A front surface of the first substrate 510 may correspond to the penetration surface 241.

The second substrate 530 may be a transparent or opaque flat panel, and may reflect the first light 560, which has penetrated the first substrate 510, the first liquid 521 and the second liquid 522 sequentially, toward the light guide element 220a. A front surface of the second substrate 530 may correspond to the reflection surface 243a.

The first electrode 540 may be formed on the edge of the rear surface of the first substrate 510. A first insulation layer 545 having an electricity insulating characteristic may be formed on the surface of the first electrode 540.

The second electrode 550 may be formed on the edge of the front surface of the second substrate 530. A second insulation layer 555 having an electricity insulating characteristic may be formed on the surface of the second electrode 550.

The first liquid 521 and the second liquid 522 may be injected into an internal space of the variable lens 540a and may be disposed between the first substrate 510 and the second substrate 530. The first liquid 521 and the second liquid 522 may not be mixed, and a refractive index of the second liquid 522 may be larger than that of the first liquid 521. For example, the first liquid 521 may be water and the second liquid 522 may be oil. An interface between the first liquid 521 and the second liquid 522 may correspond to the refraction surface 242.

The processor may control the shape (or the form) of the refraction surface 242 (or a refractive power or a curvature of the refraction surface 242) by adjusting voltages applied to the first electrode 540 and the second electrode 550. For example, the refractive power may be defined as a reciprocal of the focal length with respect to a parallel light. For example, the first electrode 540 is connected to the ground (or the ground electrode/line/cable) and a control voltage according to a control signal of the processor may be applied to the second electrode 550. For example, a concave refraction surface has a negative (−) curvature (or the radius of curvature) and a convex refraction surface has a positive (+) curvature (or the radius of curvature). The curvature corresponds to a reciprocal of the radius of curvature. In a case of the refraction surface corresponding to an aspherical surface, the curvature may refer to a curvature at the peak of the refraction surface (or a point wherein the refraction surface and the optical axis meet).

For example, when the refraction surface 242 is concave as seen from the side of the first substrate 510, the variable lens 240a may perform the same function as that of a bi-concave lens. The first light 560 progressing in parallel to the optical axis may penetrate the first substrate 510 and primarily refract from the refraction surface 242 in a direction to be farther away from the optical axis 244, and the first light 560 may be reflected from the reflection surface 243a. The reflected first light 560 may secondarily refract on the refraction surface 242 in a direction to be farther away from the optical axis 244, and the secondarily refracted first light may penetrate the first substrate 510.

Referring to FIG. 5B, for example, when the refraction surface 242 is convex as seen from the side of the first substrate 510, the variable lens 240a may perform the same function as that of a bi-convex lens. A first light 565 progressing in parallel to the optical axis 244 may penetrate the first substrate 510 and primarily refract from the refraction surface 242 in a direction to be closer to the optical axis 244, and the first light 565 may be reflected from the reflection surface 243a. The reflected first light 565 may secondarily refract on the refraction surface 242 in a direction to be closer to the optical axis 244, and the secondarily refracted first light 565 may penetrate the first substrate 510.

Figure 5C:
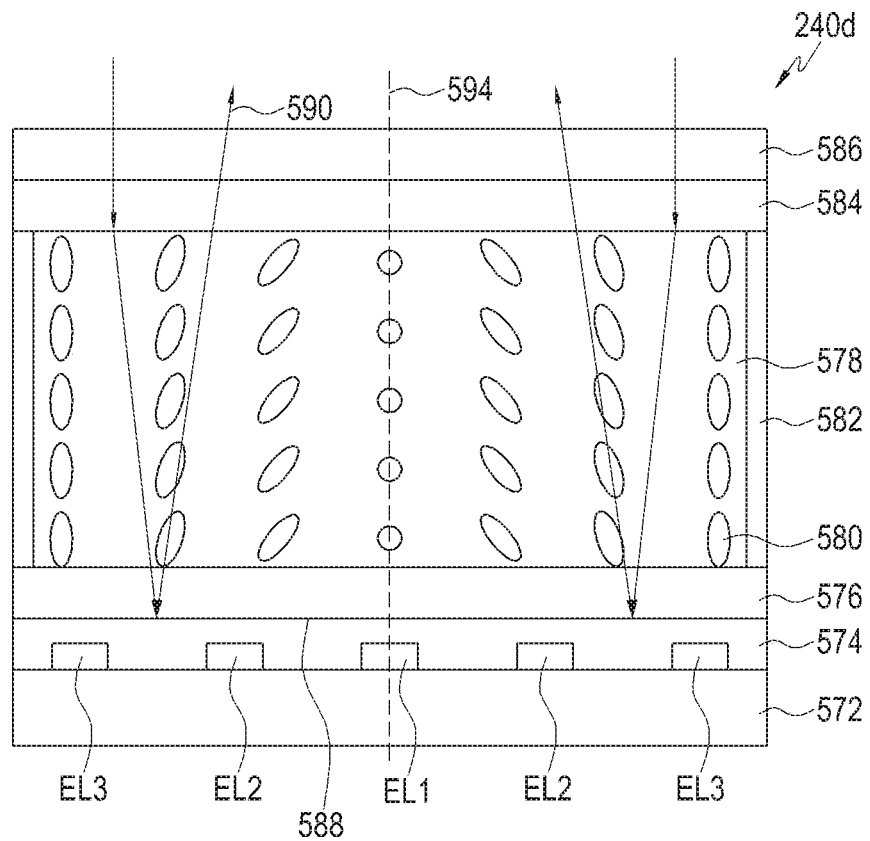
FIGS. 5C and 5D illustrate a variable lens according to various embodiments of the present disclosure.
Figure 5D:
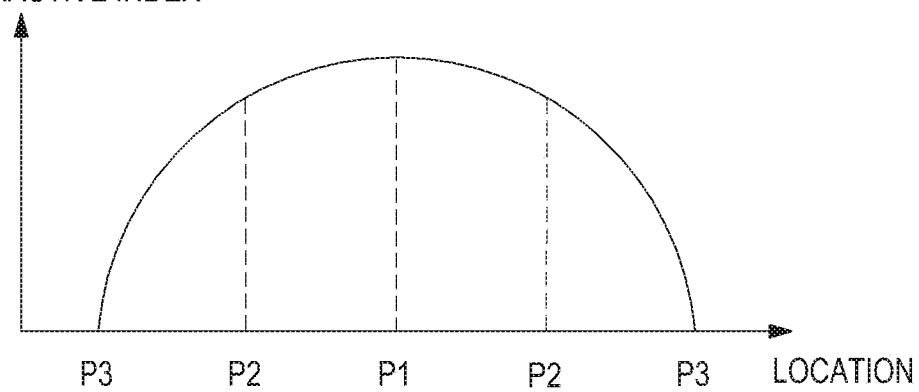

FIGS. 5C and 5D illustrate a variable lens according to various embodiments of the present disclosure.

Referring to FIG. 5C, a variable lens 240d may include first and second substrates 572 and 586, an insulation layer 574, a plurality of electrodes EL1, EL2, and EL3, first and second alignment films (or layers) 576 and 584, a liquid crystal layer 578, and a sealant 582.

Each of the first and second substrates 572 and 586 may be formed with plastic or glass.

The insulation layer 574 may be disposed on the surface (or top surface) of the first substrate 572 and may be formed with an organic material or inorganic material having an insulating nature (or electrical insulating properties).

The plurality of electrodes EL1, EL2, and EL3 may be disposed on the surface (or top surface) of the first substrate 572 and disposed within the insulation layer 574. The electrode may be formed with a transparent conductive material, such as indium tin oxide (ITO).

The first alignment film 576 may be disposed on the surface (or top surface) of the insulation layer 574 and may perform a function of pretilting liquid molecules 580 within the liquid crystal layer 578.

The liquid crystal layer 578 may be disposed on the surface (or top surface) of the first alignment film 576 and may include a plurality of liquid crystal molecules 580 of which orientations are controlled according to an intensity of an electric field applied by the plurality of electrodes EL1, EL2, and EL3.

The second alignment film 584 may be disposed on the surface (or top surface) of the liquid crystal layer 578 and may perform a function of pretilting liquid molecules 580 within the liquid crystal layer 578.

The second substrate 586 may be disposed on the surface (or top surface) of the second alignment film 584.

The sealant 582 may be disposed between the first and second alignment films 576 and 584 to surround side surface(s) of the liquid crystal layer 578 and may perform a function of sealing the liquid crystal layer 578.

A reflection surface 588 (or a reflection layer) that reflects the incident first light 590 may be disposed between the first alignment film 576 and the insulation layer 574 (or the surface of one of the first alignment film 576, the insulation layer 574, and the first substrate 572).

Although not illustrated, for example, a patternless grounding electrode in a flat panel form may be disposed on the surface of one of the second substrate 586 and the second alignment film 584.

According to an embodiment of the present disclosure, the first light 590 may be incident to the first substrate 572 from the outside, and the grounding electrode may perform a function of the reflection surface, or a reflection surface may be disposed on the surface of one of the second substrate 586 and the second alignment 584.

The processor may control the orientations of the liquid crystal molecules 580 by adjusting voltages applied to the plurality of electrodes EL1, EL2, and EL3.

For example, the processor may control distribution (or profile) of the orientations or tilt angles of the liquid crystal molecules 580 by increasing or decreasing the voltages applied to the plurality of electrodes EL1, EL2, and EL3. The voltage applied to the electrode EL1, EL2, and EL3 may increase or decrease as the electrode is positioned farther away from the center of the liquid crystal layer 578 in a width direction of the liquid crystal layer 578. According to the increase (or decrease) in the voltage, the tilt angle of the liquid crystal molecules 580 based on the surface (or top surface) of the first substrate 572 may increase (or decrease) as the liquid crystal molecules 580 are positioned farther away from the center. For example, the liquid crystal molecules 580 at the center may be arranged such that the major axes thereof are parallel to the surface of the first substrate 572 as the lowest voltage is applied to the first electrode EL1. The liquid crystal molecules 580 positioned between the center and the edge of the liquid crystal layer 578 in the width direction may be arranged such that the major axes thereof have a slope, which is not the right angle, with the surface of the first substrate 572 as the intermediate voltage is applied to the second electrodes EL2. The liquid crystal molecules 580 at the edge may be arranged such that the major axes thereof have the right angle with the surface of the first substrate 572 as the highest voltage is applied to the third electrodes EL3.

In FIG. 5D, a horizontal axis indicates a location according to the width direction of the liquid crystal layer 578 and a vertical axis indicates a refractive index. P1 denotes a location corresponding to the first electrode EL1, P2 denotes a location corresponding to the second electrode EL2, and P3 denotes a location corresponding to the third electrode EL3.

Referring to FIG. 5D, tilt angles of the liquid crystal molecules 580 based on the surface (or top surface) of the first substrate 572 may gradually increase as the location changes from the center toward the edge based on the width direction of the liquid crystal layer 578 and the voltages applied to the plurality of electrodes EL1, EL2, and EL3 increase. According to the gradual increase in the tilt angles of the liquid crystal molecules 580 as the location changes from the center toward the edges, the refractive index of the liquid crystal layer 578 may gradually decrease. In the refractive index profile as illustrated in FIG. 5D, the variable lens 240d may perform the same function as that of the bi-convex lens. According to an embodiment of the present disclosure, the processor may control the variable lens 240d to perform the same function as that of the bi-concave lens by decreasing the voltages applied to the plurality of electrodes EL1, EL2, and EL3 as the location changes from the center toward the edge.

Referring to FIG. 5C, the first light 590 sequentially penetrates the second substrate 586 and the second alignment film 584 and primarily refracts in a direction to be closer to an optical axis 594 of the liquid crystal layer 578, and the first light 590 may be reflected from the reflection surface 588. The reflected first light 590 may secondarily refract in a direction to be closer to the optical axis 594 of the liquid crystal layer 578, and the secondarily refracted first light 590 may sequentially penetrate the second alignment film 584 and the second substrate 586.

According to an embodiment of the present disclosure, the variable lens 240d may replace the variable lens 240a illustrated in FIG. 5A.

Figure 6:
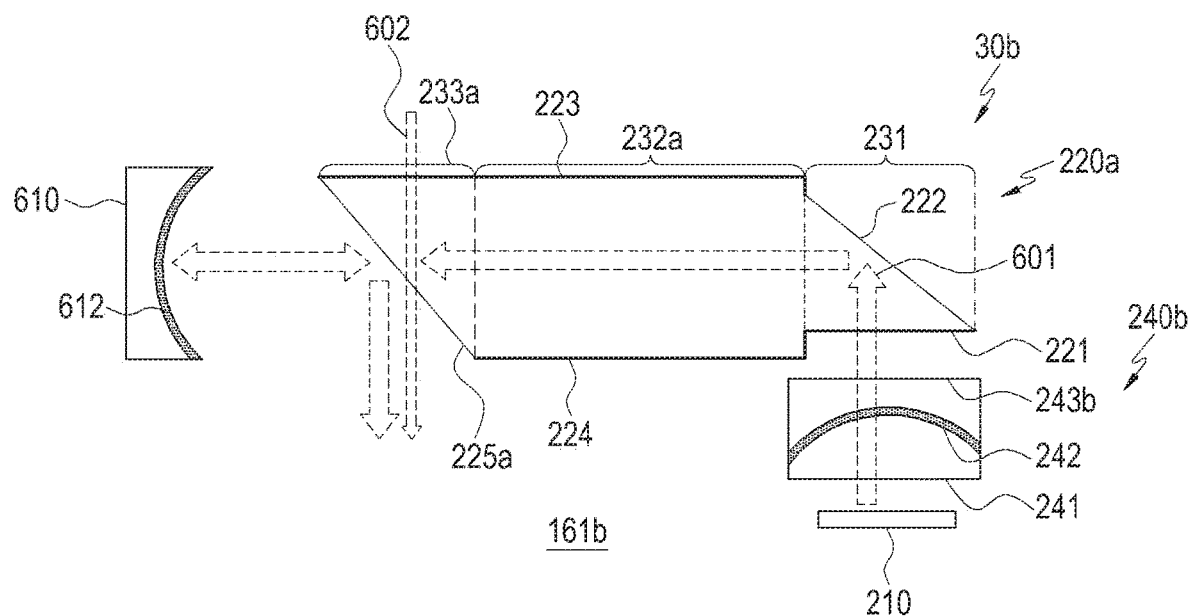
FIG. 6 illustrates a first projection type display unit according to an embodiment of the present disclosure.

FIG. 6 illustrates a first projection type display unit according to an embodiment of the present disclosure.

Referring to FIG. 6, the first projection type display unit 161b has a similar configuration to that of the first projection type display unit 161a illustrated in FIG. 2, and there is only a difference in that the configuration and location of the variable lens change and a mirror is further included in FIG. 6. Accordingly, an overlapping description will be omitted.

The first projection type display unit 161b may include the display element 210 and a light guide unit 30b. The light guide unit 30b may include the light guide element 220a, a mirror 610, and the variable lens 240b.

The first surface 221 may correspond to a part of the rear surface of the light guide element 220a facing the variable lens 240b, and may allow the first light 601, which is received after being output from the display element 210 and penetrating the variable lens 240b, to pass therethrough toward the second surface 222.

The fifth surface 225a corresponds to a second side surface of the light guide element 220a located between the third and fourth surfaces 223 and 224, and may allow the received first light 601 to pass therethrough toward the mirror 610 and reflect the first light 601 received from the mirror 610 toward the user's eye. The fifth surface 225a may allow a second light 602 forming a front view (or an optical image of the view) of the wearable device 101 to pass therethrough toward the user's eye.

The mirror 610 may include a reflection surface 612, and the reflection surface 612 may reflect the first light 601 received from the light guide element 220a toward the fifth surface 225a. The reflection surface 612 may be an aspherical surface or a spherical surface having a constant curvature (or radius of curvature).

The variable lens 240b may include a first penetration surface 241 for allowing the first light 601 received after being output from the display element 210 to pass therethrough, a refraction surface 242 for refracting the first light 601 having penetrated the penetration surface 241, and a second penetration surface 243b for allowing the first light 601 having penetrated the refraction surface 242 to pass therethrough. A shape (or form) or curvature of the refraction surface 242 may vary according to a control of the processor. The variable lens 240b may control a location (or a virtual object distance between the user's eye and a virtual object) of a virtual image displayed on an actual view (or an optical image of the view) in the front of the wearable device (for example, the wearable device 101) by adjusting an incident angle of the first light 601 incident to the user's eye according to a change in the shape (or form) or curvature of the refraction surface 242.

Figure 7A:
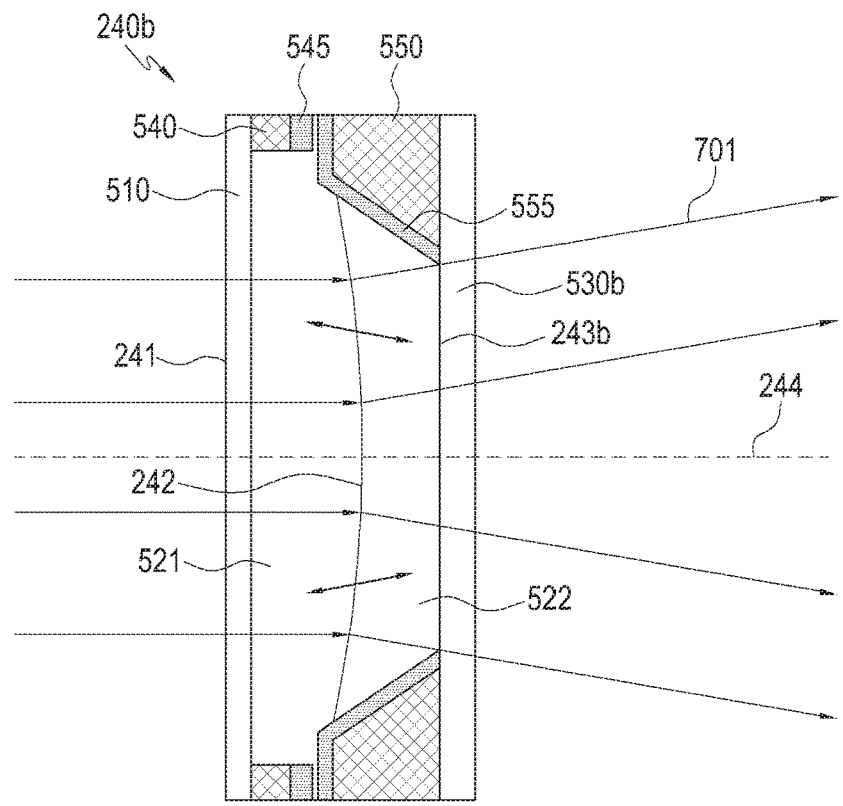
FIGS. 7A and 7B illustrate a variable lens according to various embodiments of the present disclosure.
Figure 7B:
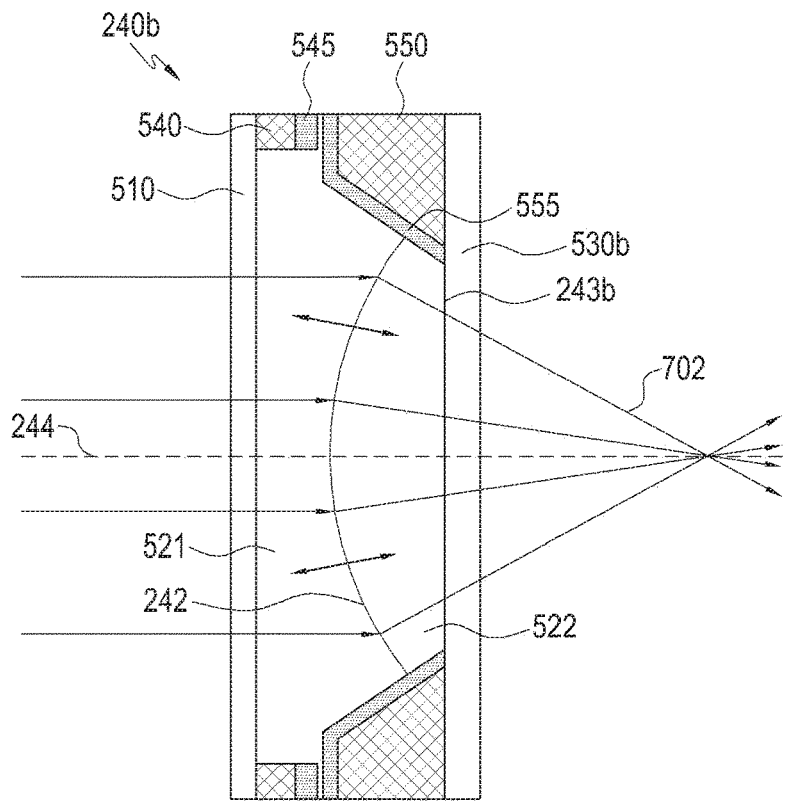

FIGS. 7A and 7B illustrate a variable lens according to various embodiments of the present disclosure.

Referring to FIGS. 7A and 7B, the variable lens 240b has a similar configuration as that of the variable lens 240a illustrated in FIG. 5A, and there is only difference in that the reflection surface is replaced with the second penetration surface in FIG. 7A. Accordingly, an overlapping description will be omitted.

Referring to FIG. 7A, the variable lens 240b may include first and second substrate 510 and 530b, first and second electrodes 540 and 550, and first and second liquids 521 and 522.

The first substrate 510 may be a transparent flat panel, and may allow a first light 701 received from the light guide element 220 to pass therethrough. A front surface of the first substrate 510 may correspond to the first penetration surface 241.

The second substrate 530b may be a transparent flat panel, and may allow the first light 701, which has penetrated the first substrate 510, the first liquid 521, and the second liquid 522, to pass therethrough. Each of the front surface and the rear surface of the second substrate 530b may correspond to the second penetration surface 243b.

The first electrode 540 may be formed on the rear surface of the first substrate 510. A first insulation layer 545 may be formed on the surface of the first electrode 540.

The second electrode 550 may be formed on the front surface of the second substrate 530b. The second insulation layer 555 may be formed on the surface of the second electrode 550.

The first liquid 521 and the second liquid 522 may be injected into an internal space of the variable lens 240b and may be disposed between the first substrate 510 and the second substrate 530b. The first liquid 521 and the second liquid 522 may not be mixed, and a refractive index of the second liquid 522 may be larger than that of the first liquid 521. For example, the first liquid 521 may be water and the second liquid 522 may be oil. An interface between the first liquid 521 and the second liquid 522 may correspond to the refraction surface 242.

The processor may control the shape (or form) of the refraction surface 242 by adjusting voltages applied to the first electrode 540 and the second electrode 550. For example, the first electrode 540 is connected to the ground (or the ground electrode/line/cable) and a control voltage according to a control signal of the processor may be applied to the second electrode 550.

For example, when the refraction surface 242 is concave as seen from the side of the first substrate 510, the variable lens 240b may perform the same function as that of a concave lens (or a plane-concave lens). The first light 701 progressing in parallel to the optical axis 244 may penetrate the first substrate 510 and refract in a direction to be farther away from the optical axis 244, and the refracted first light 701 may penetrate the second substrate 530b.

Referring to FIG. 7B, for example, when the refraction surface 242 is convex as seen from the side of the first substrate 510, the variable lens 240b may perform the same function as that of a bi-convex lens. A first light 702 progressing in parallel to the optical axis 244 may penetrate the first substrate 510 and refract on the refraction surface 242 in a direction to be closer to the optical axis 244, and the refracted first light 702 may penetrate the second substrate 530b.

Figure 7C:
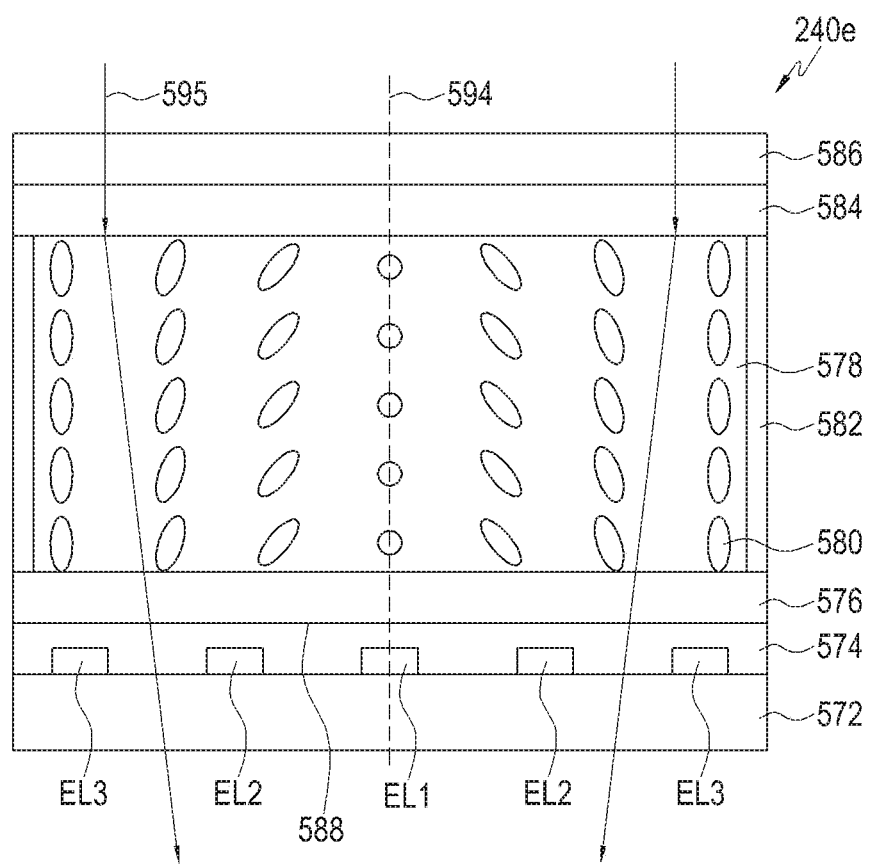
FIG. 7C illustrates a variable lens according to an embodiment of the present disclosure.

FIG. 7C illustrates a variable lens according to an embodiment of the present disclosure.

Referring to FIG. 7C, a variable lens 240e has a similar configuration as that of the variable lens 240d illustrated in FIG. 5B, and there is only difference in that the reflection surface is removed in FIG. 7B. Accordingly, an overlapping description will be omitted.

The variable lens 240e may include the first and second substrates 572 and 586, the insulation layer 574, the plurality of electrodes EL1, EL2, and EL3, the first and second alignment films (or layers) 576 and 584, the liquid crystal layer 578, and the sealant 582.

The first light 595 may sequentially penetrate the second substrate 586 and the second alignment 584 and refract on the liquid crystal layer 578 in a direction to be closer to the optical axis 594. The refracted first light 595 may sequentially penetrate the first alignment film 576, the insulation layer 574, and the first substrate 572.

According to an embodiment of the present disclosure, the variable lens 240e may replace the variable lens 240b illustrated in FIG. 7A.

Figure 8:
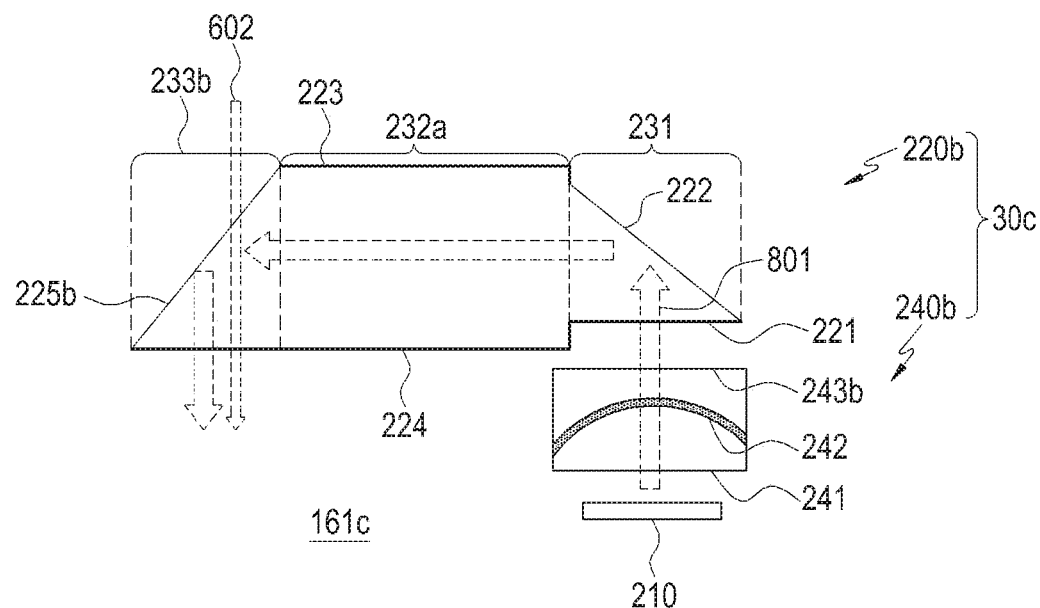
FIG. 8 illustrates a first projection type display unit lens according to an embodiment of the present disclosure.

FIG. 8 illustrates a first projection type display unit according to an embodiment of the present disclosure.

Referring to FIG. 8, the first projection type display unit 161c has a similar configuration to that of the first projection type display unit 161b illustrated in FIG. 6, and there is only a difference in that the mirror is removed and the fifth surface serves as the reflection surface in FIG. 8. Accordingly, an overlapping description will be omitted.

The first projection type display unit 161c may include the display element 210 and a light guide unit 30c. The light guide unit 30c may include a light guide element 220b, and the variable lens 240b.

A fifth surface 225b corresponds to a second side surface of the light guide element 220b located between the third and fourth surfaces 223 and 224, and may reflect an incident first light 801 toward the user's eye. The fifth surface 225b may allow the second light 602 forming a front view (or an optical image of the view) of the wearable device 101 to pass therethrough toward the user's eye.

The light guide element 220b may include the body part 232a between the third and fourth optical surfaces 223 and 224 having a uniform thickness, the first inclined part 231 between the first and second surfaces 221 and 222, of which the thickness gradually decrease from one end thereof (or from one end of the body part 232a) to the other end thereof, and a second inclined part 233b between the third and fourth surfaces 223 and 224, of which the thickness gradually decrease from one end thereof (or from the other end of the body part 232a) to the other end thereof. The second inclined part 233b may have the fifth surface 225b corresponding to an inclined surface facing the view in the front of the wearable device 101.

Figure 9:
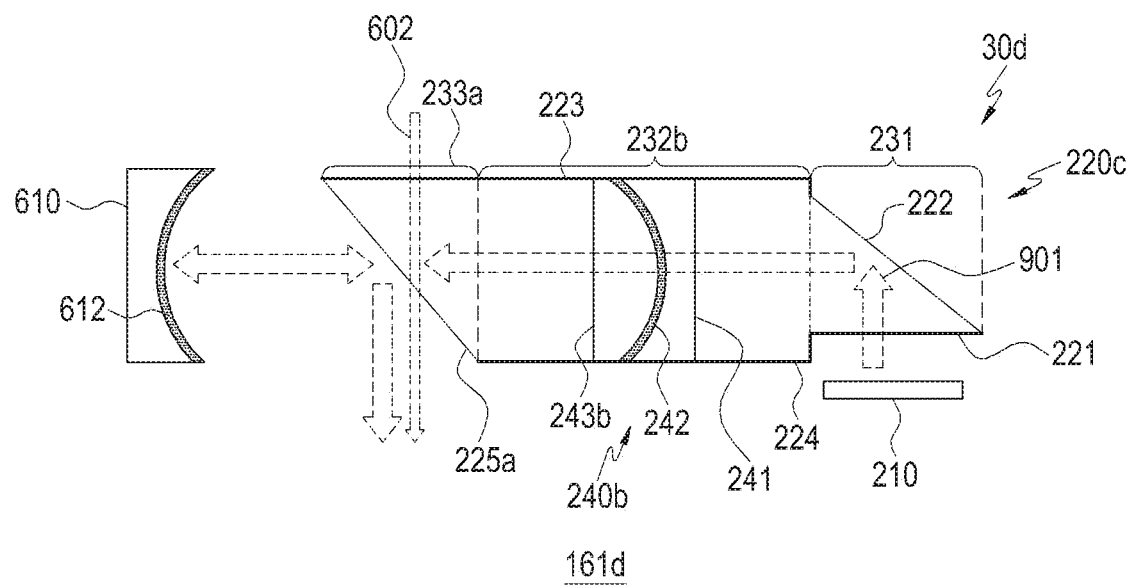
FIG. 9 illustrates a first projection type display unit lens according to an embodiment of the present disclosure.

FIG. 9 illustrates a first projection type display unit according to an embodiment of the present disclosure.

Referring to FIG. 9, the first projection type display unit 161d has a similar configuration to that of the first projection type display unit 161b illustrated in FIG. 6, and there is only a difference in that the location of the variable lens changes in FIG. 9. Accordingly, an overlapping description will be omitted.

The first projection type display unit 161d may include the display element 210 and a light guide unit 30d. The light guide unit 30d may include a light guide element 220c, the mirror 610, and the variable lens 240b.

The first surface 221 may correspond to a part of the rear surface of the light guide element 220c facing the display element 210, and may allow a first light 901 received from the display element 210 to pass therethrough toward the second surface 222.

The third surface 223 corresponds to the front surface of the light guide element 220c facing the first window 90, the fourth surface 224 corresponds to the remaining part of the rear surface of the light guide element 220c facing the user, and the third and fourth surfaces 223 and 224 may reflect (or totally reflect) the received first light 901 to make the first light 901 reach the fifth surface 225a.

The light guide element 220c may include a body part 232b between the third and fourth optical surfaces 223 and 224 having a uniform thickness, the first inclined part 231 between the first and second surfaces 221 and 222, of which the thickness gradually decrease from one end thereof (or from one end of the body part 232b) to the other end thereof, and the second inclined part 233a between the third and fourth surfaces 223 and 224, of which the thickness gradually decrease from one end thereof (or from the other end of the body part 232b) to the other end thereof.

The variable lens 240b may be inserted into the middle of the body part 232b. The body part 232b may include a groove or a hole to accommodate the variable lens 240b or include two parts separated from each other. The variable lens 240b may include the first penetration surface 241 for allowing the first light 901 progressing inside the body part 232b to pass therethrough, the refraction surface 242 for refracting the first light having penetrated the penetration surface 241, and the second penetration surface 243b for allowing the first light 901 having penetrated the refraction surface 242 to pass therethrough. A shape (or form) or curvature of the refraction surface 242 may vary according to a control of the processor. The variable lens 240b may control a location (or a virtual object distance between the user's eye and a virtual object) of a virtual image displayed on an actual view (or an optical image of the view) in the front of the wearable device (for example, the wearable device 101) by adjusting an incident angle of the first light 901 incident to the user's eye according to a change in the shape (or form) or curvature of the refraction surface 242.

Figure 10:
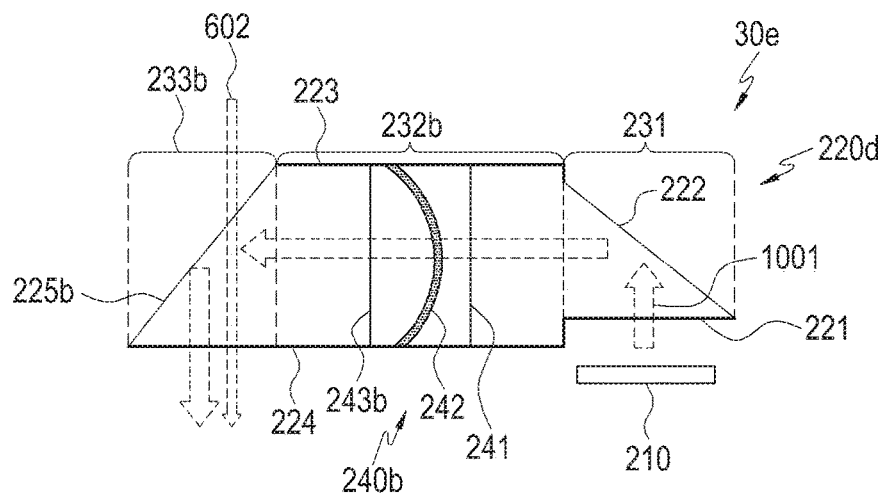
FIG. 10 illustrates a first projection type display unit lens according to an embodiment of the present disclosure.

FIG. 10 illustrates a first projection type display unit according to an embodiment of the present disclosure.

Referring to FIG. 10, a first projection type display unit 161e has a similar configuration to that of the first projection type display unit 161c illustrated in FIG. 8, and there is only a difference in that the location of the variable lens changes in FIG. 10. Accordingly, an overlapping description will be omitted.

The first projection type display unit 161e may include the display element 210 and a light guide unit 30e. The light guide unit 30e may include a light guide element 220d, and the variable lens 240b.

The first surface 221 may correspond to a part of the rear surface of the light guide element 220d facing the display element 210, and may allow a first light 1001 received from the display element 210 to pass therethrough toward the second surface 222.

The third surface 223 corresponds to the front surface of the light guide element 220d facing the first window 90, the fourth surface 224 corresponds to the remaining part of the rear surface of the light guide element 220d facing the user, and the third and fourth surfaces 223 and 224 may reflect (or totally reflect) the received first light 1001 to make the first light 1001 reach the fifth surface 225b.

The light guide element 220d may include the body part 232b between the third and fourth optical surfaces 223 and 224 having a uniform thickness, the first inclined part 231 between the first and second surfaces 221 and 222, of which the thickness gradually decrease from one end thereof (or from one end of the body part 232b) to the other end thereof, and the second inclined part 233b between the third and fourth surfaces 223 and 224, of which the thickness gradually decrease from one end thereof (or from the other end of the body part 232b) to the other end thereof. The second inclined part 233b may have the fifth surface 225b corresponding to an inclined surface facing the view in the front of the wearable device 101.

The variable lens 240b may be inserted into the middle of the body part 232b. The body part 232b may include a groove or a hole to accommodate the variable lens 240b or include two parts separated from each other. The variable lens 240b may include the first penetration surface 241 for allowing the first light progressing inside the body part 232b to pass therethrough, the refraction surface 242 for refracting the first light having penetrated the penetration surface 241, and the second penetration surface 243b for allowing the first light having penetrated the refraction surface 242 to pass therethrough. A shape (or form) or curvature of the refraction surface 242 may vary according to a control of the processor. The variable lens 240b may control a location (or a virtual object distance between the user's eye and a virtual object) of a virtual image displayed on an actual view (or an optical image of the view) in the front of the wearable device (for example, the wearable device 101) by adjusting an incident angle of the first light 1001 incident to the user's eye according to a change in the shape (or form) or curvature of the refraction surface 242.

Figure 11:
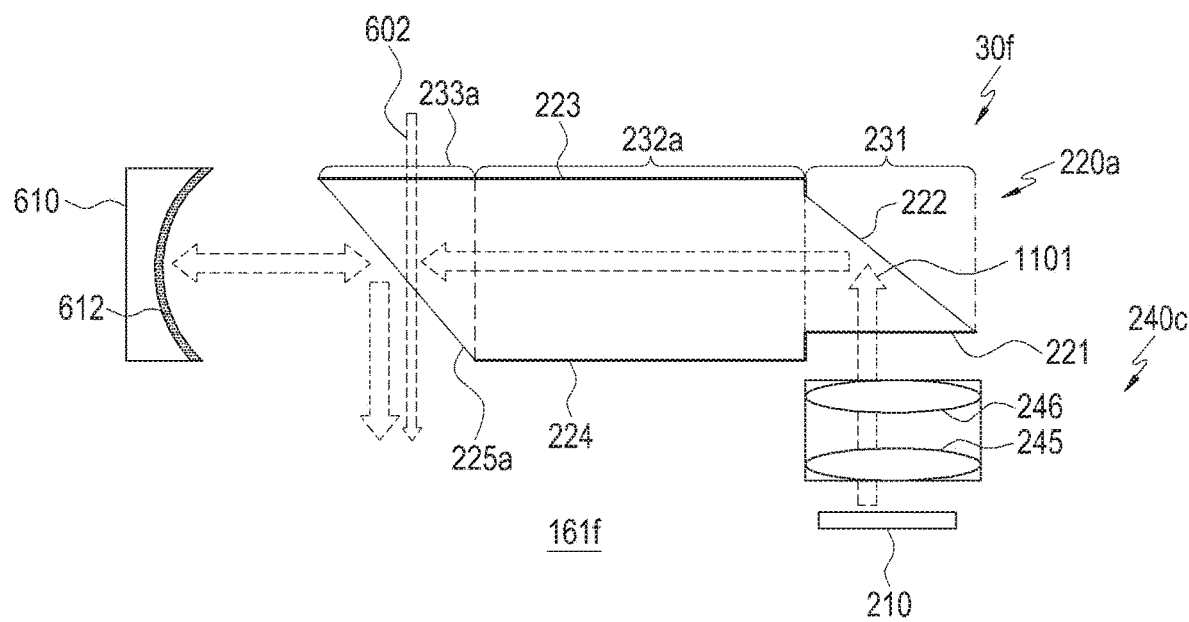
FIG. 11 illustrates a first projection type display unit lens according to an embodiment of the present disclosure.

FIG. 11 illustrates a first projection type display unit according to an embodiment of the present disclosure.

Figure 12:
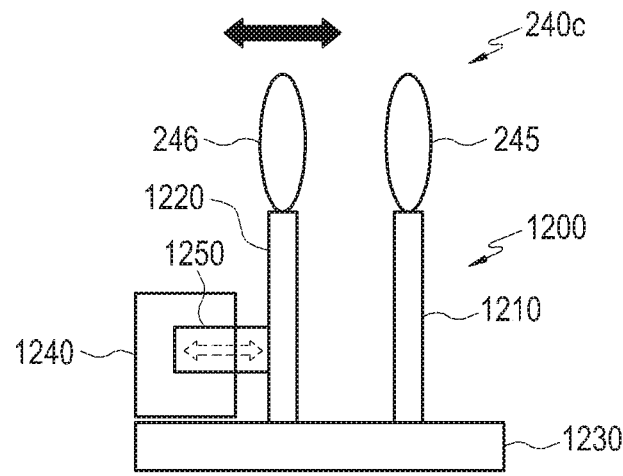
FIG. 12 illustrates a lens driver lens according to an embodiment of the present disclosure.

Referring to FIG. 11, a first projection type display unit 161f has a similar configuration to that of the first projection type display unit 161b illustrated in FIG. 6, and there is only a difference in that the configuration of the variable lens changes and a lens driver 1200 illustrated in FIG. 12 is further included in FIG. 11. Accordingly, an overlapping description will be omitted. Referring to FIG. 11, the lens driver 1200 is not illustrated.

The first projection type display unit 161f may include the display element 210, a light guide unit 30f and the lens driver 1200. The light guide unit 30f may include the light guide element 220a, the mirror 610, and a variable lens 240c.

The first surface 221 may correspond to a part of the rear surface of the light guide element 220a facing the variable lens 240c, and may allow a first light 1101, which is received after being output from the display element 210 and penetrating the variable lens 240c, to pass therethrough toward the second surface 222.

The fifth surface 225a corresponds to a second side surface of the light guide element 220a located between the third and fourth surfaces 223 and 224, and may penetrate the received first light 1101 toward the mirror 610 and reflect the first light 1101 received from the mirror 610 toward the user's eye. The fifth surface 225a may allow a second light 602 forming a front view (or an optical image of the view) of the wearable device 101 to pass therethrough toward the user's eye.

The mirror 610 may include the reflection surface 612, and the reflection surface 612 may reflect the first light 1101 received from the light guide element 220a toward the fifth surface 225a. The reflection surface 612 may be an aspherical surface or a spherical surface having a constant curvature (or radius of curvature).

The variable lens 240c may include a first sub lens 245 for primarily refracting the first light 1101 received after being output from the display element 210 and a second sub lens 246 for secondarily refracting the primarily refracted first light 1101. A distance between the first and second sub lenses 245 and 246 may vary according to a control of the processor. The variable lens 240c may control a location (or a virtual object distance between the user's eye and a virtual object) of a virtual image displayed on an actual view (or an optical image of the view) in the front of the wearable device (for example, the wearable device 101) by adjusting an incident angle of the first light 1101 incident to the user's eye according to a change in the distance between the first and second sub lenses 245 and 246.

FIG. 12 illustrates a lens driver according to an embodiment of the present disclosure.

Referring to FIG. 12, a lens driver 1200 may include first and second supporting parts 1210 and 1220, a guide 1230, and an actuator 1240.

The first sub lens 245 is fixed to one end of the first supporting part 1210, and the other end of the first supporting part 1210 is fixed to the guide 1230.

The second sub lens 246 is fixed to one end of the second supporting part 1220 and the other end of the second supporting part 1220 is fixed to the guide 1230 to be movable.

The actuator 1240 may include a forward and backward movable arm 1250, and the arm 1250 may be fixed to the second supporting part 1220. The actuator 1240 may move the arm 1250 in a direction of a length of the guide 1230 to correspond to a distance or a location according to a control signal of the processor.

Figure 13:
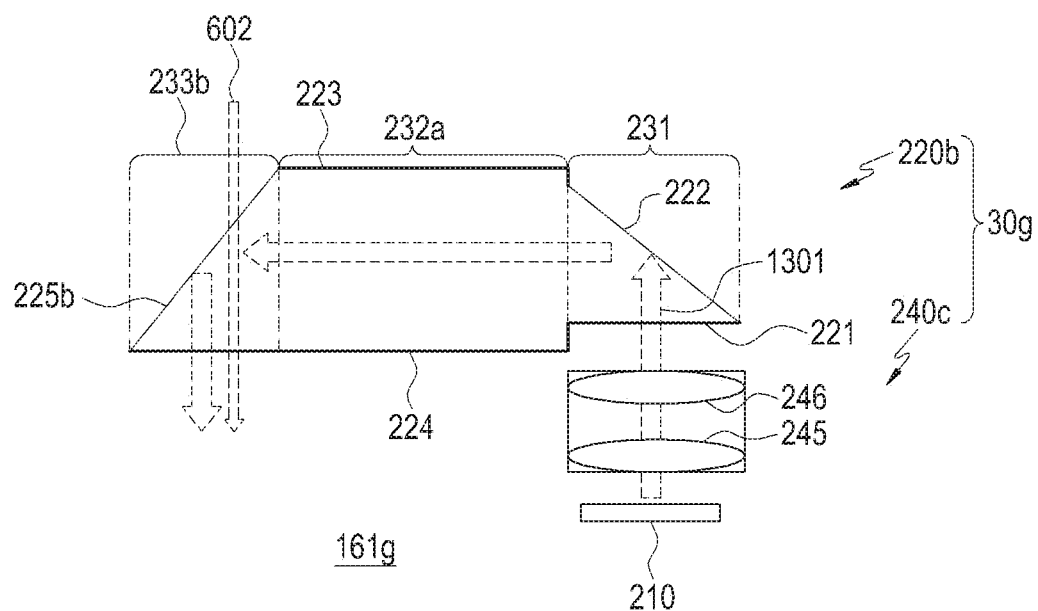
FIG. 13 illustrates a first projection type display unit lens according to an embodiment of the present disclosure.

FIG. 13 illustrates a projection type display unit according to an embodiment of the present disclosure.

Referring to FIG. 13, a first projection type display unit 161g has a similar configuration to that of the first projection type display unit 161c illustrated in FIG. 8, and there is only a difference in that the configuration of the variable lens changes and the lens driver 1200 illustrated in FIG. 12 is further included in FIG. 13. Accordingly, an overlapping description will be omitted. Referring to FIG. 13, the lens driver 1200 is not illustrated.

The first projection type display unit 161g may include the display device 210, a light guide unit 30g and the lens driver 1200. The light guide unit 30g may include the light guide element 220b, and the variable lens 240c.

The first surface 221 may correspond to a part of the rear surface of the light guide element 220b facing the variable lens 240c, and may allow a first light 1301, which is received after being output from the display element 210 and penetrating the variable lens 240c, to pass therethrough toward the second surface 222.

The fifth surface 225b corresponds to a second side surface of the light guide element 220b located between the third and fourth surfaces 223 and 224, and may reflect an incident first light 1301 toward the user's eye. The fifth surface 225 may allow the second light 602 forming a front view (or an optical image of the view) of the wearable device 101 to pass therethrough toward the user's eye.

The light guide element 220b may include the body part 232a between the third and fourth optical surfaces 223 and 224 having a uniform thickness, the first inclined part 231 between the first and second surfaces 221 and 222, of which the thickness gradually decrease from one end thereof (or from one end of the body part 232a) to the other end thereof, and a second inclined part 233b between the third and fourth surfaces 223 and 224, of which the thickness gradually decrease from one end thereof (or from the other end of the body part 232a) to the other end thereof. The second inclined part 233b may have the fifth surface 225b corresponding to an inclined surface facing the view in the front of the wearable device 101.

The variable lens 240c may include a first sub lens 245 for primarily refracting the first light 1301 received after being output from the display element 210 and a second sub lens 246 for secondarily refracting the primarily refracted first light 1301. A distance between the first and second sub lenses 245 and 246 may vary according to a control of the processor. The variable lens 240c may control a location (or a virtual object distance between the user's eye and a virtual object) of a virtual image displayed on an actual view (or an optical image of the view) in the front of the wearable device (for example, the wearable device 101) by adjusting an incident angle of the first light 1301 incident to the user's eye according to a change in the distance between the first and second sub lenses 245 and 246.

Figure 14:
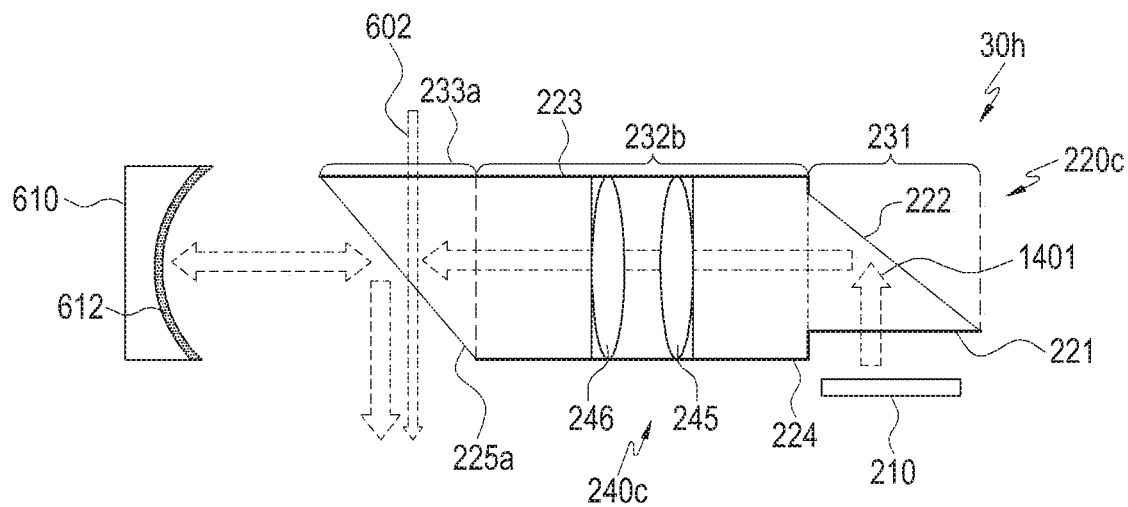
FIG. 14 illustrates a first projection type display unit lens according to an embodiment of the present disclosure.

FIG. 14 illustrates a first projection type display unit according to an embodiment of the present disclosure.

Referring to FIG. 14, the first projection type display unit 161h has a similar configuration to that of the first projection type display unit 161d illustrated in FIG. 9, and there is only a difference in that the configuration of the variable lens changes in FIG. 14. Accordingly, an overlapping description will be omitted.

The first projection type display unit 161h may include the display element 210, a light guide unit 30h and the lens driver 1200 illustrated in FIG. 12. The light guide unit 30h may include the light guide element 220c, the mirror 610, and the variable lens 240c.

The third surface 223 corresponds to the front surface of the light guide element 220c facing the first window 90, the fourth surface 224 corresponds to the remaining part of the rear surface of the light guide element 220c facing the user, and the third and fourth surfaces 223 and 224 may reflect (or totally reflect) the received first light 1401 to make the first light 1401 reach the fifth surface 225a.

The light guide element 220c may include the body part 232b between the third and fourth optical surfaces 223 and 224 having a uniform thickness, the first inclined part 231 between the first and second surfaces 221 and 222, of which the thickness gradually decrease from one end thereof (or from one end of the body part 232b) to the other end thereof, and the second inclined part 233a between the third and fourth surfaces 223 and 224, of which the thickness gradually decrease from one end thereof (or from the other end of the body part 232b) to the other end thereof.

The variable lens 240c may be inserted into the middle of the body part 232b. The body part 232b may include a groove or a hole to accommodate the variable lens 240c or include two parts separated from each other.

The variable lens 240c may include the first sub lens 245 for primarily refracting the first light 1401 progressing inside the body part 232b and the second sub lens 246 for secondarily refracting the primarily refracted first light 1401. A distance between the first and second sub lenses 245 and 246 may vary according to a control of the processor. The variable lens 240c may control a location (or a virtual object distance between the user's eye and a virtual object) of a virtual image displayed on an actual view (or an optical image of the view) in the front of the wearable device (for example, the wearable device 101) by adjusting an incident angle of the first light 1401 incident to the user's eye according to a change in the distance between the first and second sub lenses 245 and 246.

Figure 15:
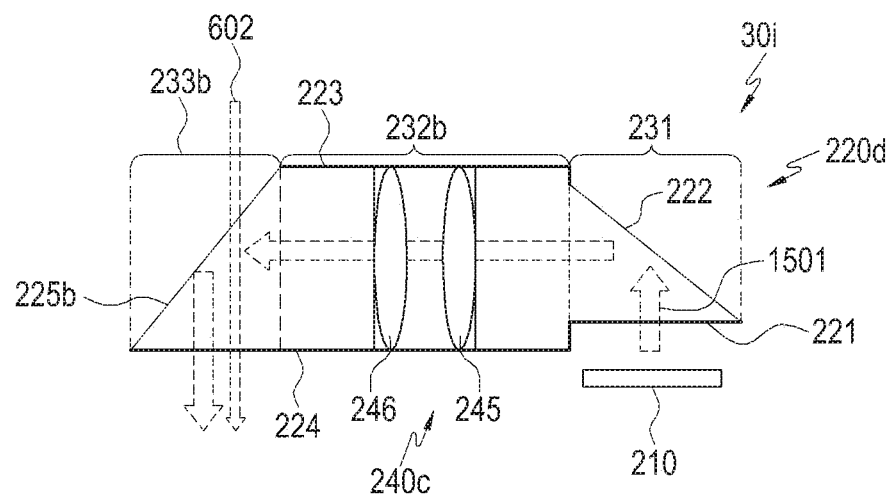
FIG. 15 illustrates a first projection type display unit lens according to an embodiment of the present disclosure.

FIG. 15 illustrates a first projection type display unit according to an embodiment of the present disclosure.

Referring to FIG. 15, the first projection type display unit 161i has a similar configuration to that of the first projection type display unit 161e illustrated in FIG. 10, and there is only a difference in that the configuration of the variable lens changes in FIG. 15. Accordingly, an overlapping description will be omitted.

The first projection type display unit 161i may include the display element 210, a light guide unit 30i and the lens driver 1200 illustrated in FIG. 12. The light guide unit 30i may include the light guide element 220d, and the variable lens 240c.

The first surface 221 may correspond to a part of the rear surface of the light guide element 220d facing the display element 210, and may allow the first light 1501 received from the display element 210 to pass therethrough toward the second surface 222.

The third surface 223 corresponds to the front surface of the light guide element 220d facing the first window 90, the fourth surface 224 corresponds to the remaining part of the rear surface of the light guide element 220d facing the user, and the third and fourth surfaces 223 and 224 may reflect (or totally reflect) the received first light 1501 to make the first light 1501 reach the fifth surface 225b.

The light guide element 220d may include the body part 232b between the third and fourth optical surfaces 223 and 224 having a uniform thickness, the first inclined part 231 between the first and second surfaces 221 and 222, of which the thickness gradually decrease from one end thereof (or from one end of the body part 232b) to the other end thereof, and the second inclined part 233b between the third and fourth surfaces 223 and 224, of which the thickness gradually decrease from one end thereof (or from the other end of the body part 232b) to the other end thereof. The second inclined part 233b may have the fifth surface 225b corresponding to an inclined surface facing the view in the front of the wearable device 101.

The variable lens 240c may be inserted into the middle of the body part 232b. The body part 232b may include a groove or a hole to accommodate the variable lens 240c or include two parts separated from each other.

The variable lens 240c may include the first sub lens 245 for primarily refracting the first light 1501 progressing inside the body part 232b and the second sub lens 246 for secondarily refracting the primarily refracted first light 1501. A distance between the first and second sub lenses 245 and 246 may vary according to a control of the processor. The variable lens 240c may control a location (or a virtual object distance between the user's eye and a virtual object) of a virtual image displayed on an actual view (or an optical image of the view) in the front of the wearable device (for example, the wearable device 101) by adjusting an incident angle of the first light 1501 incident to the user's eye according to a change in the distance between the first and second sub lenses 245 and 246.

FIG. 16 illustrates a network environment including a wearable device according to an embodiment of the present disclosure.

Referring to FIG. 16, the wearable device 101 within a network environment 100 according to various embodiments is described. The wearable device 101 may include a camera module 110, a processor 120, a bus 121, a memory 130, an input/output interface 150, a display 160, a communication interface 170, and a sensor module 190. According to some embodiments of the present disclosure, the wearable device 101 may omit at least some of the above components or further include other components.

The bus 121 may include, for example, a circuit for connecting the components 110 to 130 and transmitting communication between the components (for example, control messages and/or data).

The processor 120 may include one or more of a CPU, an AP, and a communication processor (CP). The processor 120 may control, for example, one or more other components of the wearable device 101 and/or process an operation or data related to communication. The processor 120 may be called a controller, or may include a controller as a part thereof or constitute a part of the controller.

The memory 130 may include a volatile memory and/or a non-volatile memory. The memory 130 may store, for example, commands or data related to one or more other components of the wearable device 101. According to an embodiment of the present disclosure, the memory 130 may store software and/or a program 140. The program 140 may include a kernel 141, middleware 143, an application programming interface (API) 145, and/or an application program (or "application") 147. At least some of the kernel 141, the middle 143, and the API 145 may be referred to as an operating system (OS).

The kernel 141 may control or manage system resources (for example, the bus 121, the processor 120, or the memory 130) used for executing an operation or function implemented by other programs (for example, the middleware 143, the API 145, or the application 147). Furthermore, the kernel 141 may provide an interface through which the middleware 143, the API 145, or the application program 147 may access individual components of the wearable device 101 to control or manage system resources.

The middleware 143 may serve as, for example, an intermediary such that the API 145 or the application program 147 communicate with the kernel 141 to transmit/ receive data. Furthermore, in regard to task requests received from the application program 147, the middleware 143 may perform a control (for example, scheduling or load balancing) for the task requests using, for example, a method of assigning a priority for using the system resources (for example, the bus 121, the processor 120, or the memory 130) of the wearable device 101 to at least one application.

The API 145 is an interface by which the applications 147 control functions provided from the kernel 141 or the middleware 143, and may include, for example, at least one interface or function (for example, commands) for file control, window control, image processing, text control, and the like.

For example, the input/output interface 150 may serve as an interface that may transfer commands or data, which are input from a user or another external device, to the other component(s) of the wearable device 101. Further, the input/output interface 150 may output commands or data received from other component(s) of the wearable device 101 to the user or another external device. The input/output interface 150 may include the power button 151, the touch sensor 152, a microphone, and a speaker.

The display 160 may include the first and second projection type display units 161 and 162, and each projection type display unit may project a light forming an image of a virtual object (that is, a virtual image) onto the user's eye. The display 160 may be called a display unit.

The communication interface 170 may set, for example, communication between the wearable device 101 and an external device (for example, a first external electronic device 102, a second external electronic device 104, or a server 106). For example, the communication interface 170 may be connected to a network 162 through wireless or wired communication to communicate with the external device (for example, the second external electronic device 104 or the server 106). The communication interface 170 may be called a communication unit or a communication module. For example, the communication interface 170 may perform direct communication 164 with the first external electronic device 102.

The wireless communication may use, for example, at least one of LTE, LTE-A, CDMA, WCDMA, UMTS, WiBro, and GSM, for example, as a cellular communication protocol. The wired communication may include, for example, at least one of a universal serial bus (USB), a high definition multimedia interface (HDMI), recommended standard 232 (RS-232), and a plain old telephone Service (POTS). The network 162 may include at least one of communication networks, such as a computer network (for example, a LAN or a WAN), the Internet, and a telephone network.

Each of the first external electronic device 102 and the second external electronic device the second external electronic device 104 may be a device which is the same type as or different type from the wearable device 101. According to an embodiment of the present disclosure, the server 106 may include a group of one or more servers. According to various embodiments of the present disclosure, all or some of the operations performed by the wearable device 101 may be performed by another electronic device or a plurality of electronic devices (for example, the first external electronic device 102 or the second external electronic device 104 or the server 106). According to an embodiment of the present disclosure, when the wearable device 101 should perform some functions or services automatically or by request, the wearable device 101 may make a request for performing at least some of the functions related to the functions or services to another device (for example, the electronic device 102 or the second external electronic device 104 or the server 106) instead of performing the functions or services by itself. The other electronic device (for example, the first external electronic device 102 or the second external electronic device 104 or the server 106) may carry out the requested function or the additional function and transfer a result thereof to the wearable device 101. The wearable device 101 may provide the requested functions or services based on the received result or after additionally processing the received result. To achieve this, for example, a cloud computing, distributed computing, or client-server computing technology may be used.

According to an embodiment of the present disclosure, the server 106 may support driving of the wearable device 101 by conducting at least one of the operations (or functions) implemented in the wearable device 101. For example, the server 106 may include a virtual image providing server module 108 which may support the wearable device 101. The virtual image providing server module 108 may perform (act as a proxy) at least one of the operations performed by the processor 120.

The sensor module 190 may include first to third sensors 191 to 193.

The first sensor 191 may be disposed on the rear surface of the front frame 11 to face the user's eye, and may radiate an infrared light to the user's eye and detect the infrared light reflected from the user's eye. The first sensor 191 may output images generated by photographing the user's eye to a processor 120. The processor 120 may acquire information on a location of an eye feature point (for example, pupil) through the image received from the first sensor 191.

The second sensor 192 may detect a tilt of the wearable device 101 and output a detection signal indicating the tilt to the processor of the wearable device 101. The second sensor 192 may include a gyro sensor or a tilt sensor.

The third sensor 193 is disposed on the front surface of the front frame 11 to face the front, and may radiate an infrared light or laser to the front of the wearable device 101 and detect the infrared light or laser reflected from an actual object. The third sensor 193 may output a detection signal indicating a distance between the third sensor 193 and the actual object to the processor 120 of the wearable device 101.

Figure 17:
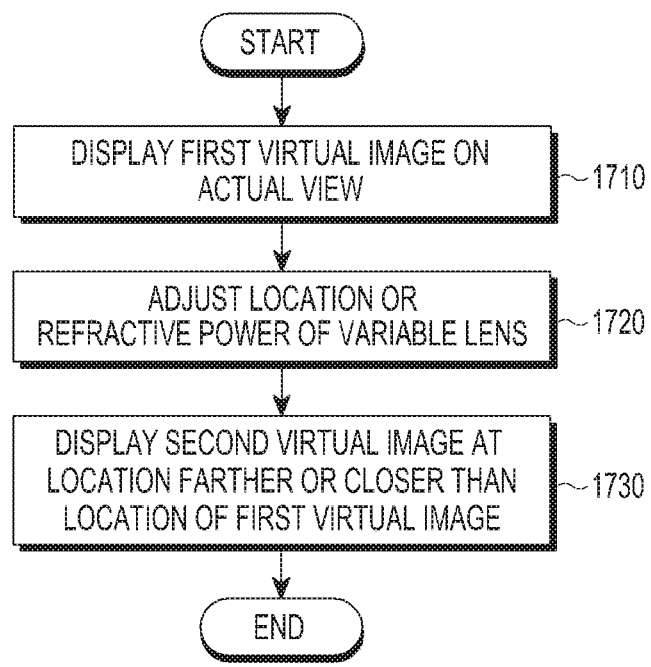
FIG. 17 is a flowchart illustrating a method of providing a virtual image according to an embodiment of the present disclosure.

FIG. 17 is a flowchart illustrating a method of providing a virtual image according to an embodiment of the present disclosure.

Referring to FIG. 17, the method of providing the virtual image may include operations 1710 to 1730.

In operation 1710, the processor (for example, the processor 120) of the wearable device (for example, the wearable device 101) may display a first virtual image on an actual view (or an optical image of the view) in the front of the wearable device through the projection type display unit (for example, the first projection type display unit 161*a*).

For example, the processor may display the first virtual image at a location corresponding to a location of a first object within the actual view (for example, a location identical to or close to the location of the first object within the actual view) through the projection type display unit.

In another example, the processor may display the first virtual image at a preset location within the actual view through the projection type display unit.

In operation 1720, the processor may adjust a location or a refractive power of the variable lens (for example, the variable lens 240*a*, 240*b*, 240*c*, 240*d*, or 240*e*) within the projection type display unit by controlling the projection type display unit.

For example, when the first object and/or the wearable device moves, the processor may adjust the location or the refractive power of the variable lens within the projection type display unit according to the changed location of the first object.

In another example, when it is detected that the user looks at a second object within the actual view, which is different from the first object, the processor may adjust the location or the refractive power of the variable lens within the projection type display unit according to a change in the viewing point.

In operation 1730, the processor may display a second virtual image at a location, which is farther or closer than the location of the first virtual image, through a control of the projection type display unit.

For example, when the first object and/or the wearable device moves, the processor may display the second virtual image at a location corresponding to the changed location of the first object (for example, a location identical or close to the location of the first object within the actual view) through the projection type display unit. In this case, the second virtual image may have the content identical to that of the first image, differing only in the location.

In another example, when it is detected that the user looks at the second object within the actual object, which is different from the first object, the processor may display the second virtual image at a location corresponding to the location of the second object (for example, a location identical or close to the location of the second object within the actual view) through the projection type display unit. In this case, the second virtual image may have the content and location different from those of the first virtual image or may have the content identical to that of the first virtual image, differing only in the location.

Figure 18:
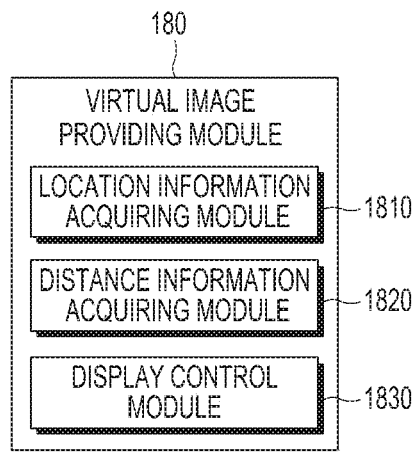
FIG. 18 is a block diagram illustrating a virtual image providing module of a wearable device according to an embodiment of the present disclosure.

FIG. 18 illustrates a block diagram of a virtual image providing module of a wearable device according to an embodiment of the present disclosure.

Referring to FIG. 18, the virtual image providing module 180 may process at least some of the information obtained from other components (for example, at least one of the camera module 110, the processor 120, the memory 130, the input/output interface 150, the communication interface 170, and the sensor module 190) and utilize the same in various manners. For example, the virtual image providing module 180 may control at least some functions of the wearable device 101 by using the processor 120 or independently therefrom so that the wearable device 101 may interwork with other electronic devices (for example, the first external electronic device 102 or the second external electronic device 104 or the server 106). All or some of the virtual image providing module 180 may be integrated into the processor 120. According to an embodiment of the present disclosure, at least one component of the virtual image providing module 180 may be included in the server 106 (for example, a virtual image providing server module 108) and receive supporting of at least one operation implemented by the virtual image providing module 180 from the server 106.

The virtual image providing module 180 may include a location information acquiring module 1810, a distance information acquiring module 1820, and a display control module 1830. All or some of the virtual image providing module 180 may be provided separately from the processor (for example, the processor 120) or may be integrated into the processor.

The location information acquiring module 1810 according to various embodiments may acquire information on a location of an eye feature point (for example, iris or pupil). For example, the location information acquiring module 1810 may acquire the information on the location of the feature point through an eye image input through the first sensor (for example, the first sensor 191).

According to an embodiment of the present disclosure, the information on the location of the feature point may include a coordinate, a value, a location range, or the like.

According to an embodiment of the present disclosure, the location information acquiring module 1810 may acquire the information on the location based on one of preset different location ranges of the eye.

According to an embodiment of the present disclosure, the location information acquiring module 1810 may acquire, as the information on the location, a location range including the feature point among the preset different location ranges of the eye or a particular location within the location range.

According to an embodiment of the present disclosure, the information on the location may include a location on a preset axis of the eye.

The distance information acquiring module 1820 according to various embodiments may acquire information on a distance between a preset reference point (for example, user's eye or the wearable device 101) and a viewing point of the actual view (for example, an actual object) based on the information on the location of the feature point.

According to an embodiment of the present disclosure, the information on the distance may include a distance value or a distance range.

According to an embodiment of the present disclosure, the distance information acquiring module 1820 may acquire the information on the distance based on one of preset different location ranges.

According to an embodiment of the present disclosure, the different distance ranges may include a first distance range, a second distance range farther and/or wider than the first distance range, and a third distance range farther and/or wider than the second distance range.

According to an embodiment of the present disclosure, the information on the distance may include a distance on a preset axis.

According to an embodiment of the present disclosure, the distance information acquiring module 1820 may acquire, as the information on the distance, a distance range corresponding to the information on the location of the feature point among the preset different distance ranges or a particular location within the distance range.

According to an embodiment of the present disclosure, the distance information acquiring module 1820 may determine whether the location of the feature point is fixed for a preset threshold time, and, when the location of the feature point is fixed for the preset threshold time, acquire the information on the distance.

According to an embodiment of the present disclosure, the distance information acquiring module 1820 may acquire information on a tilt of the wearable device through the second sensor (for example, the second sensor 192), and acquire the information on the distance based on the information on the location of the feature point and the information on the tilt.

According to an embodiment of the present disclosure, the distance information acquiring module 1820 may acquire the information on the tilt of the wearable device through the second sensor, and acquire, as the information on the distance, a distance range corresponding to the information on the tilt and the information on the location of the feature point among the preset different distance ranges or a particular location within the distance range.

According to an embodiment of the present disclosure, the distance information acquiring module 1820 may acquire the information on the tilt of the wearable device through the second sensor, determine a first distance range corresponding to the information on the tilt among the preset different distance ranges, and acquire, as the information on the distance, a second distance range corresponding to the information on the location of the feature point among the preset different distance ranges within the first distance range or a particular location within the second distance range.

According to an embodiment of the present disclosure, the distance information acquiring module 1820 may measure a distance between the preset reference point and at least one actual object within the actual view through the third sensor (for example, the third sensor 193) and acquire the information on the distance based on the information on the location of the feature point and the measured distance.

According to an embodiment of the present disclosure, the distance information acquiring module 1820 may measure the distance between the preset reference point and at least one actual object within the actual view through the third sensor, determine a distance range corresponding to the information on the location of the feature point among the preset different distance ranges, determine whether the measured distance is included in the determined distance range, and acquire, as the information on the distance, the measured distance when the measured distance is included in the determined distance range, and acquire, as the information on the distance, the determined distance range or a particular location within the determined distance range when the measured distance is not included in the determined distance range.

According to an embodiment of the present disclosure, the distance information acquiring module 1820 may measure distances between the preset reference point and actual objects within the actual view through the third sensor, determine a distance range corresponding to the information on the location of the feature point among the preset different distance ranges, and acquire, as the information on the distance, a distance included in the determined distance range among the measured distances.

According to an embodiment of the present disclosure, the distance information acquiring module 1820 may acquire the information on the tilt of the wearable device through the second sensor, measure the distance between the preset reference point and at least one actual object within the actual view, and acquire the information on the distance based on the information on the location of the feature point, information on the tilt, and the measured distance.

According to an embodiment of the present disclosure, the distance information acquiring module 1820 may acquire the information on the tilt of the wearable device through the second sensor, measure the distance between the preset reference point and at least one actual object within the actual view through the third sensor, determine a distance range corresponding to the information on the location of the feature point and the information on the tilt of the wearable device among the preset different distance ranges, determine whether the measured distance is included in the determined distance range, and acquire, as the information on the distance, the measured distance when the measured distance is included in the determined distance range, and acquire, as the information on the distance, the determined distance range or a particular location within the determined distance range when the measured distance is not included in the determined distance range.

According to an embodiment of the present disclosure, the distance information acquiring module 1820 may acquire the information on the tilt of the wearable device through the second sensor, measure distances between the preset reference point and actual objects within the actual view through the third sensor, determine a distance range corresponding to the information on the tilt and the information on the location of the feature point among the preset different distance ranges, and acquire, as the information on the distance, a distance included in the determined distance range among the measured distances.

The display control module 1830 according to various embodiments may display the first virtual image on the actual view (or optical image of the view) in the front of the wearable device through the first and/or second projection type display units (for example, the first and/or second projection type display units 161 and 162). The display control module 1830 may adjust a location or a refractive power of the corresponding variable lens within the first and/or second projection type display units by controlling the first and/or second projection type display units. The display control module 1830 may display the second virtual image at a location, which is farther or closer than the first virtual image, through a control of the first and/or second projection type display units. For example, the display control module 1830 may adjust the distance of the virtual image to correspond to the distance of the actual object within the actual view in front of the wearable device, so that the user may recognize that the actual object and the virtual image exist at the same or close locations on the actual view.

According to an embodiment of the present disclosure, the display control module 1830 may display the virtual image on the actual view (or optical image of the view) to locate at a virtual object distance corresponding to the information on the distance. For example, the display control module 1830 may project a first light, of which an incident angle is controlled to have the virtual object distance corresponding to the information on the distance, onto the user's eye through the first and/or second projection type display units, so that a virtual object image (that is, a virtual image) formed by the first light and the optical image of the actual view may overlap each other. The user may recognize that the virtual object exists on the actual view.

According to an embodiment of the present disclosure, the display control module 1830 may adjust the location or the refractive power of the variable lens within the first and/or second projection type display units to make the image displayed by the first and/or second projection type display units have the virtual object distance and control the first and/or second projection type display units to project the light forming the virtual image to be located at the virtual object distance.

Figure 19:
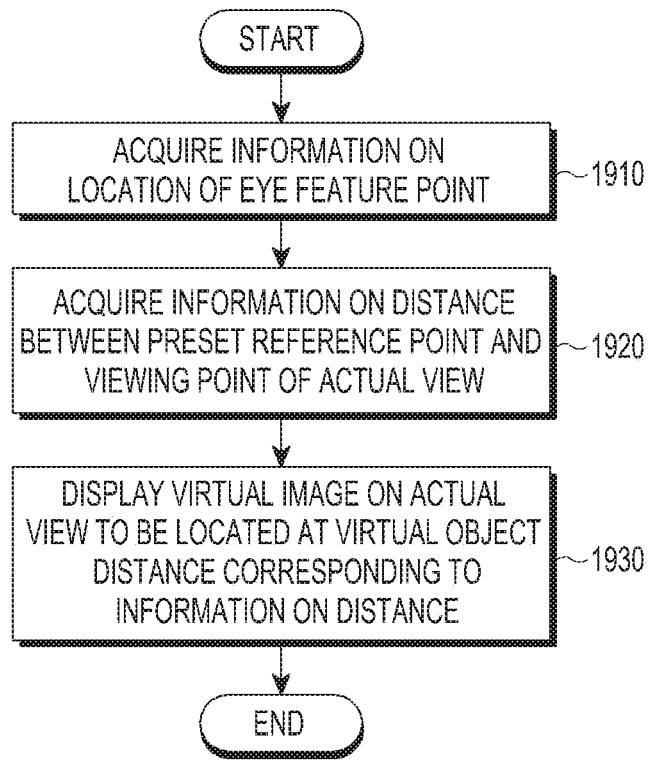
FIG. 19 is a flowchart illustrating a method of providing a virtual image according to an embodiment of the present disclosure.

FIG. 19 is a flowchart illustrating a method of providing a virtual image according to an embodiment of the present disclosure.

FIGS. 20A, 20B, and 20C illustrate a method of providing a virtual image according to various embodiments of the present disclosure.

Figures 21A, 21B, 21C:
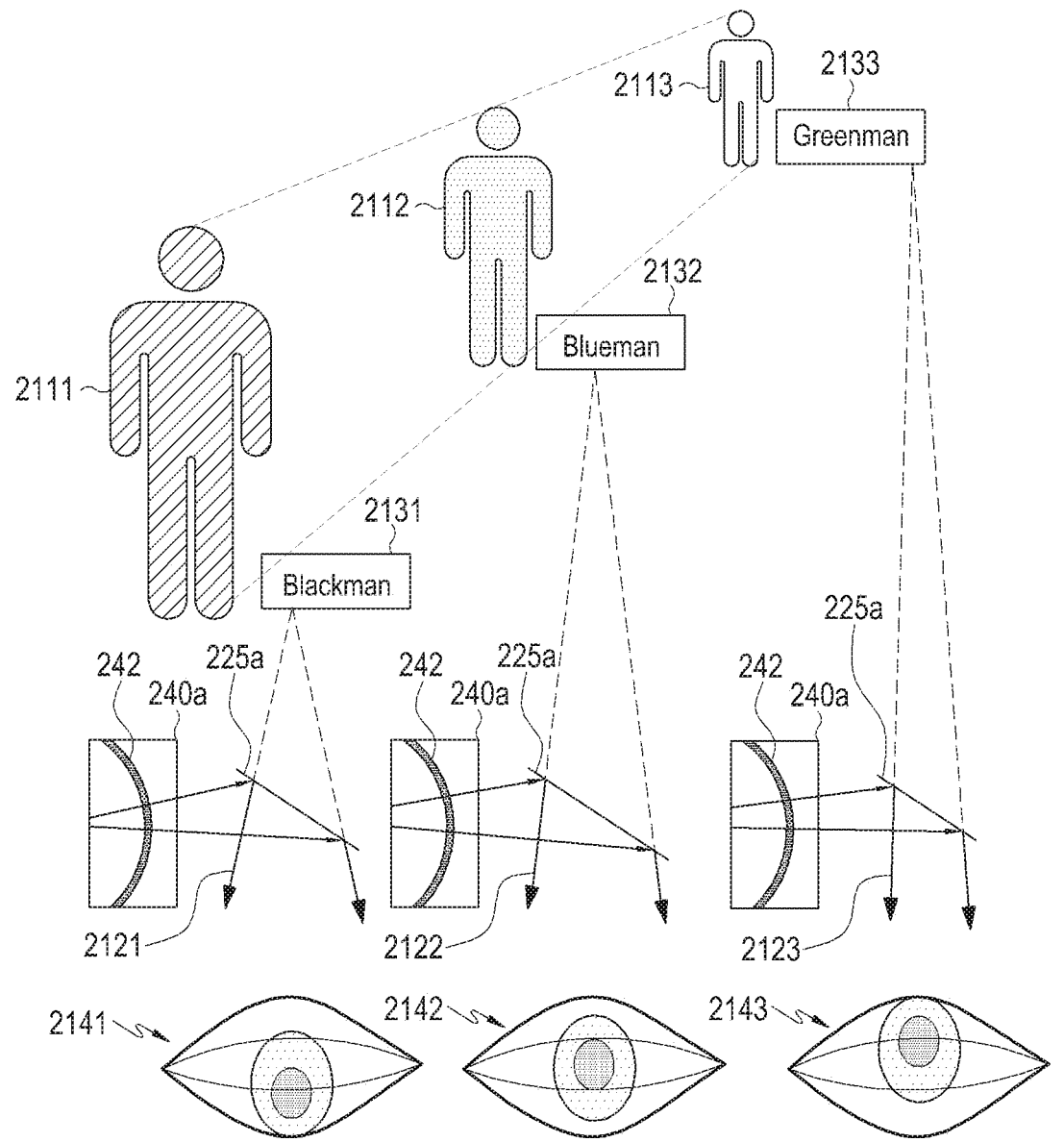
FIGS. 21A, 21B, and 21C illustrate a method of providing a virtual image according to various embodiments of the present disclosure.

FIGS. 21A, 21B, and 21C illustrate a method of providing a virtual image according to various embodiments of the present disclosure.

Referring to FIG. 19, the method of providing the virtual image may include operations 1910 to 1930.

In operation 1910, the processor (for example, the processor 120) of the wearable device (for example, the wearable device 101) may acquire an eye image through the first sensor (for example, the first sensor 191) and acquire information on a location of an eye feature point (for example, iris or pupil) from the image.

Referring to FIG. 20A, for example, the processor may acquire information on a location of a pupil 2020 in an image of an eye 2010. The processor may set first and second reference lines 2041 and 2042 to the eye 2010 and set a first location range 2051 limited by a lower outline 2031 of the eye and the first reference line 2041, a second location range 2052 limited by the first reference line 2041 and the second reference line 2042, and a third location range 2053 limited by the second reference line 2042 and an upper outline 2032 of the eye. According to this example, although the horizontal reference lines 2041 and 2042 are described, the processor may set vertical reference lines and a plurality of location ranges limited by the vertical reference line(s) and/or the outline(s) of the eye.

The processor may determine which location range among the first to third location ranges 2051 to 2053 includes the pupil 2020.

According to an embodiment of the present disclosure, the processor may determine which location range among the first to third location ranges 2051 to 2053 includes a center point of the pupil 2020.

According to an embodiment of the present disclosure, the processor may determine which location range among the first to third location ranges 2051 to 2053 includes the biggest part of the pupil 2020.

According to an embodiment of the present disclosure, the processor may determine a location on a center axis 2060 of the eye corresponding to the center point of the pupil 2020 and determine a location range including the location on the center axis 2060.

The processor may acquire, as the information on the location of the eye feature point, the determined location range or a preset location within the determined location range (for example, a center location, a start location, an end location of the location range, and/or the like).

In operation 1920, the processor may acquire information on a distance between a preset reference point (for example, user's eye or the wearable device 101) and a viewing point of the actual view (for example, an actual object) based on the information on the location of the feature point.

Referring to FIG. 20A, when the center point of the pupil 2020 is included in the first location range 2051, the processor may determine that the user looks at the actual object within the first location range (for example, a short distance range).

Referring to FIG. 20B, when the center point of the pupil 2020 is included in the second location range 2052, the processor may determine that the user looks at the actual object within the second location range (for example, a middle distance range).

Referring to FIG. 20C, when the center point of the pupil 2020 is included in the third location range 2053, the processor may determine that the user looks at the actual object within the third location range (for example, a long distance range).

The processor may acquire, as the information on the distance between the preset reference point and the viewing point of the actual view, the determined location range or a preset location within the determined location range (for example, a center location, a start location, an end location of the location range, and the like).

According to an embodiment of the present disclosure, the processor may determine a distance or a distance range according to an optical axis of the eye, a viewing axis, an axis parallel to the ground, or the like.

In operation 1930, the processor may display a virtual image on the actual view (or an optical image of the view)

to place the virtual image at the virtual object distance corresponding to the information on the distance.

Referring to FIG. 21A, the processor may determine that the user looks at a first actual object 2111 within the first distance range (for example, a short distance range from 0 to 1 m) through an image of an eye 2141 having the pupil located within the first location range. The processor may acquire, as the information on a distance between the preset reference point (for example, the user's eye) and the first actual object 2111, the first location range or a preset location within the first location range (for example, a center location, a start location, an end location of the location range, or the like). The processor may display a first virtual object 2131 (for example, an image describing the first actual object) having a virtual object distance corresponding to the first distance range or a preset location within the first distance range (for example, a distance between the user's eye and the first virtual object) on the actual view including the first actual object 2111. The following description is made based on the first projection type display unit 161a illustrated in FIG. 2 as an example. The processor may control a virtual object distance between the user's eye and the first virtual object 2131 recognized by the user to correspond to the first distance range or a preset location within the first distance range by changing the variable lens 240a (or by changing a curvature of the refraction surface 242 of the variable lens 240a) to adjust an incident angle of a first light 2121 incident to the user's eye.

Referring to FIG. 21B, the processor may determine that the user looks at a second actual object 2112 within the second distance range (for example, a middle distance range from 1 to 5 m) through an image of an eye 2142 having the pupil located within the second location range. The processor may acquire, as the information on a distance between the preset reference point (for example, the user's eye) and the second actual object 2112, the second location range or a preset location within the second location range (for example, a center location, a start location, an end location of the location range, or the like). The processor may display a second virtual object 2132 (for example, an image describing the second actual object) having a virtual object distance corresponding to the second distance range or the preset location within the second distance range (for example, the distance between the user's eye and the second virtual object) on the actual view including the second actual object 2112. The following description is made based on the first projection type display unit 161a illustrated in FIG. 2 as an example. The processor may control the virtual object distance between the user's eye and the second virtual object 2132 recognized by the user to correspond to the second distance range or the preset location within the second distance range by changing the variable lens 240a (or by changing a curvature of the refraction surface 242 of the variable lens 240a) to adjust an incident angle of a first light 2122 incident to the user's eye.

Referring to FIG. 21C, the processor may determine that the user looks at a third actual object 2113 within the third distance range (for example, a long distance range from 5 m to infinity) through an image of an eye 2143 having the pupil located within the third location range. The processor may acquire, as the information on a distance between the preset reference point (for example, the user's eye) and the third actual object 2113, the third location range or a preset location within the third location range (for example, a center location, a start location, an end location of the location range, or the like). The processor may display a third virtual object 2133 (for example, an image describing the third actual object) having a virtual object distance corresponding to the third distance range or the preset location within the third distance range (for example, the distance between the user's eye and the third virtual object) on the actual view including the third actual object 2113. The following description is made based on the first projection type display unit 161a illustrated in FIG. 2 as an example. The processor may control the virtual object distance between the user's eye and the third virtual object 2133 recognized by the user to correspond to the third distance range or the preset location within the third distance range by changing the variable lens 240a (or by changing a curvature of the refraction surface 242 of the variable lens 240a) to adjust an incident angle of a first light 2123 incident to the user's eye.

Figure 22:
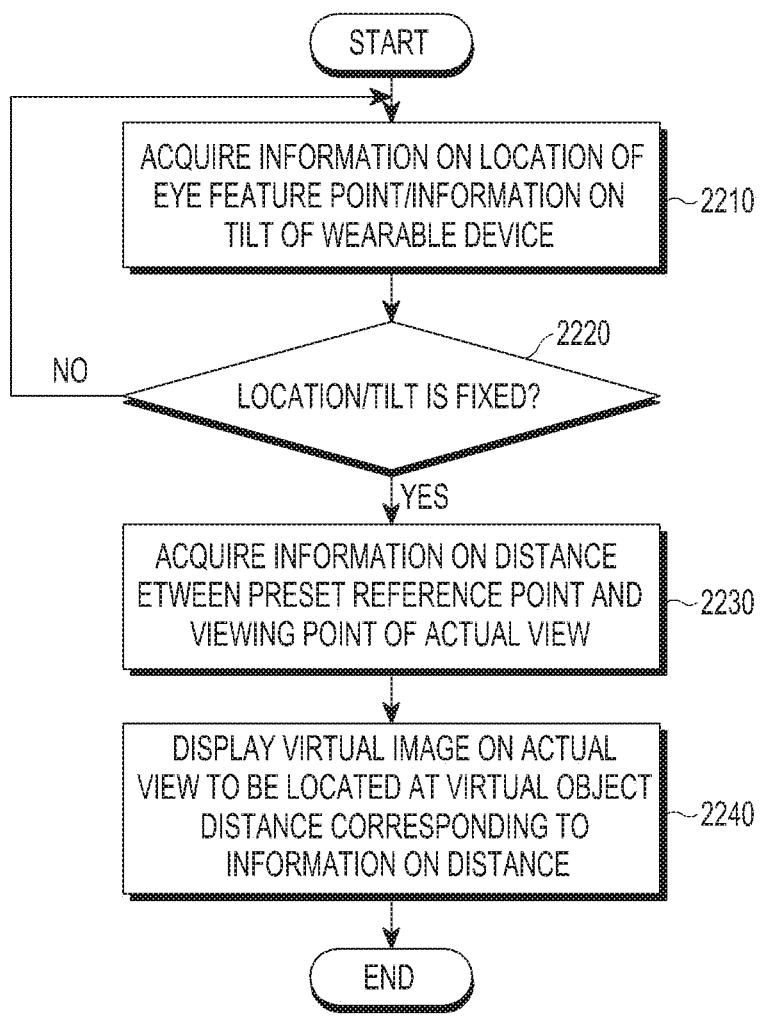
FIG. 22 is a flowchart illustrating a method of providing a virtual image according to an embodiment of the present disclosure.

FIG. 22 is a flowchart illustrating a method of providing a virtual image according to an embodiment of the present disclosure.

Referring to FIG. 22, the method of providing the virtual image may include operations 2210 to 2240.

In operation 2210, the processor (for example, the processor 120) of the wearable device (for example, the wearable device 101) may acquire an eye image through the first sensor (for example, the first sensor 191) and acquire information on a location of an eye feature point (for example, iris or pupil) from the image.

The processor may acquire information on a tilt of the wearable device through the second sensor (for example, the second sensor 192).

Referring back to FIG. 1, the processor may acquire information on an angle θ of an axis of symmetry 21 in a length direction of the wearable device 101 with respect to a direction 20 orthogonal to the ground through the second sensor. For example, when the wearable device 101 faces the ground, the angle θ may be 0 degrees. When the wearable device is parallel to the ground, the angle θ may be 90 degrees.

The processor may set a range from 0 degrees to a first threshold angle (for example, 45 degrees) as a first tilt range, a range from the first threshold angle to a second threshold angle (for example, 70 degrees) as a second tilt range, and a range from the second threshold angle to a third threshold angle (for example, 90 degrees or more) as a third tilt range.

The processor may determine to which tilt range the tilt of the wearable device belongs among the first to third tilt ranges.

The processor may acquire information on a distance between a preset reference point (for example, user's eye or the wearable device 101) and a viewing point of the actual view (for example, the actual object) based on the information on the tilt of the wearable device.

For example, when the tilt of the wearable device belongs to the first tilt range, the processor may determine that the user looks at the actual object within the first distance range (for example, the short distance range).

For example, when the tilt of the wearable device belongs to the second tilt range, the processor may determine that the user looks at the actual object within the second distance range (for example, the middle distance range).

For example, when the tilt of the wearable device belongs to the third tilt range, the processor may determine that the user looks at the actual object within the third distance range (for example, the long distance range).

The processor may acquire, as the information on the distance between the preset reference point and the viewing point of the actual view, the determined location range or a preset location within the determined location range (for example, a center location, a start location, an end location of the location range, or the like).

The processor may acquire information on the distance between the preset reference point (for example, user's eye or the wearable device 101) and the viewing point of the actual view (for example, the actual object) based on the location of the eye feature point and/or the information on the tilt of the wearable device.

For example, when the information on the location of the eye feature point corresponds to the first distance range (for example, the short distance range from 0 to 1 m) and the information on the tilt of the wearable device corresponds to the second distance range (for example, the middle distance range from 1 m to 5 m), the processor may acquire, as the information on the distance, a distance (for example, 1 m) corresponding to a middle between the first distance range and the second distance range.

In operation 2220, the processor may determine whether the location of the feature point and/or the tilt of the wearable device are fixed for a preset threshold time. The processor may perform operation 2230 when the location/tilt is fixed, and repeat operation 2210 when the location/tilt is not fixed.

In operation 2230, the processor may acquire the information on the distance between the preset reference point (for example, user's eye or the wearable device 101) and the viewing point of the actual view (for example, the actual object) based on information on the location of the feature point and/or the information on the tilt of the wearable device.

In operation 2240, the processor may display a virtual image on the actual view (or an optical image of the view) to place the virtual image at the virtual object distance corresponding to the information on the distance.

Figure 23:
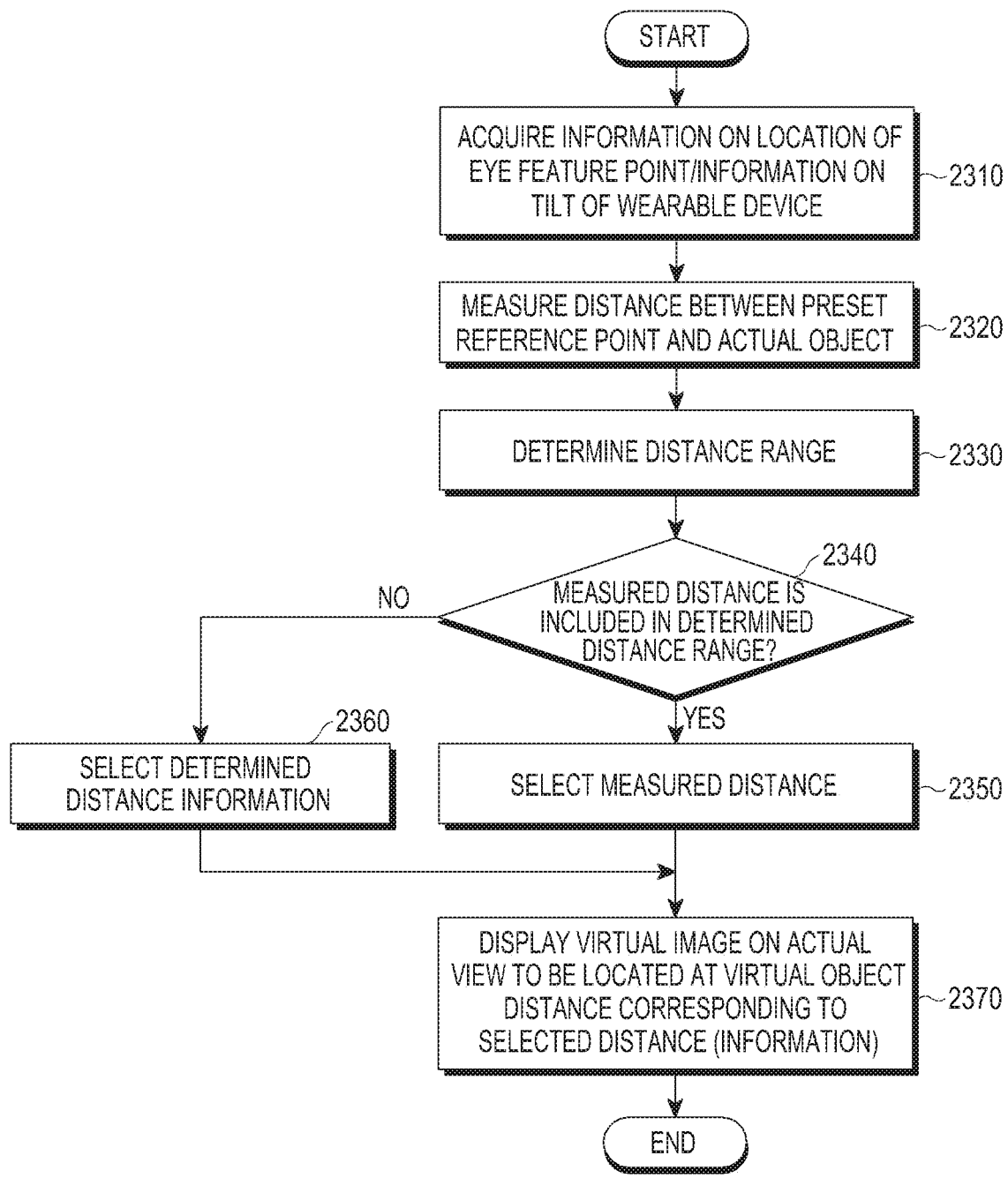
FIG. 23 is a flowchart illustrating a method of providing a virtual image according to an embodiment of the present disclosure.

FIG. 23 is a flowchart illustrating a method of providing a virtual image according to an embodiment of the present disclosure.

Referring to FIG. 23, the method of providing the virtual image may include operations 2310 to 2370.

In operation 2310, the processor (for example, the processor 120) of the wearable device (for example, the wearable device 101) may acquire an eye image through the first sensor (for example, the first sensor 191) and acquire information on a location of an eye feature point (for example, iris or pupil) from the image.

The processor may acquire information on a tilt of the wearable device through the second sensor (for example, the second sensor 192).

In operation 2320, the processor may measure a distance between a preset reference point (for example, the user's eye or the wearable device 101) and an actual object of the actual view through the third sensor (for example, the third sensor 193).

In operation 2330, the processor may determine a distance range between the preset reference point and a viewing point based on information on a location of the feature point and/or a tilt of the wearable device.

In operation 2340, the processor may determine whether the measured distance belongs to the determined distance range. When the measured distance belongs to the determined distance range, the processor may perform operation 2350. When the measured distance does not belong to the determined distance range, the processor may perform operation 2360.

In operation 2350, the processor may select, determine, or acquire the measured distance as the information on the distance between the preset reference point and the viewing point of the actual view.

In operation 2360, the processor may select, determine, or acquire the determined distance range as the information on the distance between the preset reference point and the viewing point of the actual view.

In operation 2370, the processor may display a virtual image on the actual view (or the optical image of the view) to place the virtual image at a virtual object distance corresponding to the selected distance (or distance range).

Referring to FIGS. 21A, 21B, and 21C, when the actual view includes first and second actual objects 2111 and 2112, the third sensor may measure a distance between the preset reference point and the first actual object 2111, which is closer than the second actual object 2112. When the determined distance range corresponds to the second distance range (for example, the middle distance range from 1 m to 5 m) rather than the first distance range (for example, the short distance range from 0 to 1 m), the processor may determine or acquire the determined distance range as the information on the distance between the preset reference point and the viewing point of the actual view.

Figure 24:
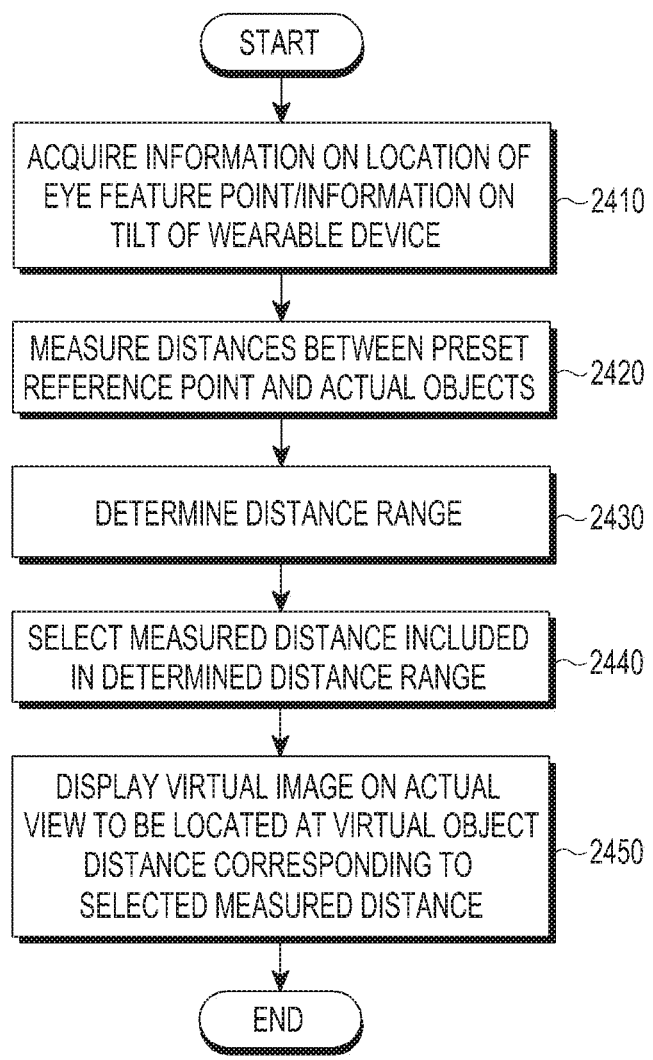
FIG. 24 is a flowchart illustrating a method of providing a virtual image according to an embodiment of the present disclosure.

FIG. 24 is a flowchart illustrating a method of providing a virtual image according to an embodiment of the present disclosure.

Referring to FIG. 24, the method of providing the virtual image may include operations 2410 to 2450.

In operation 2410, the processor (for example, the processor 120) of the wearable device (for example, the wearable device 101) may acquire an eye image through the first sensor (for example, the first sensor 191) and acquire information on a location of an eye feature point (for example, iris or pupil) from the image.

The processor may acquire information on a tilt of the wearable device through the second sensor (for example, the second sensor 192).

In operation 2420, the processor may measure distances between a preset reference point (for example, the user's eye or the wearable device 101) and actual objects within the actual view through the third sensor (for example, the third sensor 193).

In operation 2430, the processor may determine a distance range between the preset reference point and a viewing point based on information on a location of the feature point and/or a tilt of the wearable device.

In operation 2440, the processor may select, determine, or acquire a measured distance included in the determined distance range among the measured distances as information on the distance between the preset reference point and the viewing point of the actual view.

In operation 2450, the processor may display a virtual image on the actual view (or the optical image of the view) to place the virtual image at a virtual object distance corresponding to the selected distance.

Referring to FIGS. 21A, 22B, and 21C, when the actual view includes first and second actual objects 2111 and 2112, the third sensor may measure all distances between the preset reference point and the first actual object 2111 and the second actual object 2112. When the determined distance range corresponds to the first distance range (for example, the short distance range from 0 to 1 m), the processor may determine or acquire the measured distance of the first actual object 2111 as the information on the distance between the preset reference point and the viewing point of the actual view.

Figure 25:
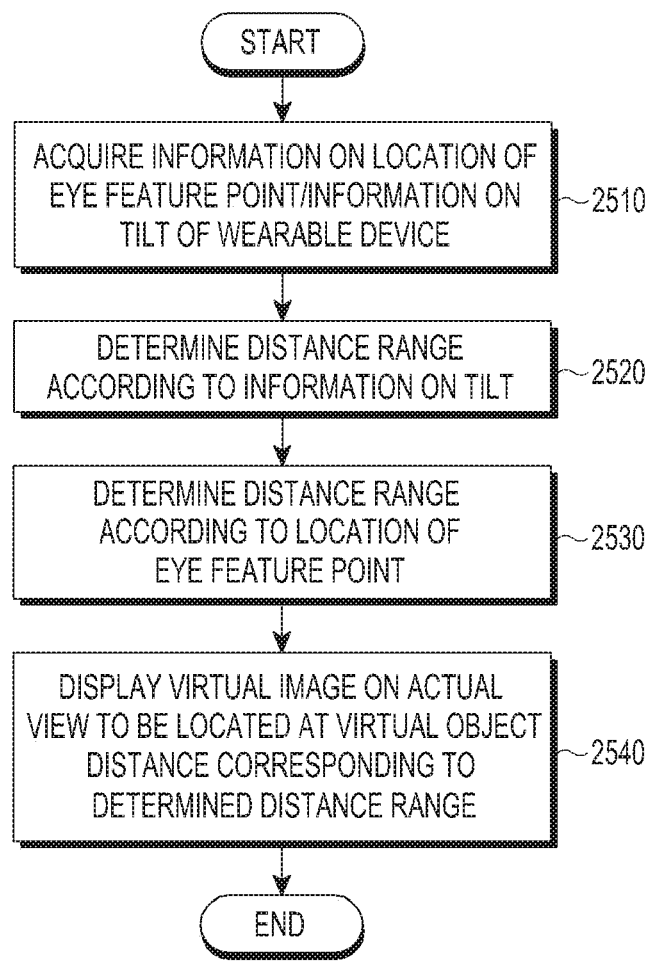
FIG. 25 is a flowchart illustrating a method of providing a virtual image according to an embodiment of the present disclosure.

FIG. 25 is a flowchart illustrating a method of providing a virtual image according to an embodiment of the present disclosure.

Referring to FIG. 25, the method of providing the virtual image may include operations 2510 to 2540.

In operation 2510, the processor (for example, the processor 120) of the wearable device (for example, the wearable device 101) may acquire an eye image through the first sensor (for example, the first sensor 191) and acquire information on a location of an eye feature point (for example, iris or pupil) from the image.

The processor may acquire information on a tilt of the wearable device through the second sensor (for example, the second sensor 192).

In operation 2520, the processor may determine a primary distance range between the preset reference point and a viewing point based on information on a tilt of the wearable device (or information on a location of the feature point).

In operation 2530, the processor may determine a secondary distance range between a preset reference point and the viewing point within the primary distance range based on the information on the location of the feature point (or the information on the tilt of the wearable device).

In operation 2540, the processor may display a virtual image on the actual view (or the optical image of the view) to place the virtual image at a virtual object distance corresponding to the secondary distance range.

For example, one of the short/middle distance range (for example, the range from 0 to 5 m) and the long distance range (for example, the range from 5 m to infinity) may be determined based on the information on the tilt of the wearable device (or the information on the location of the feature point). Further, one of the short distance range (for example, the range from 0 to 1 m) and the middle distance range (for example, the range from 1 m to 5 m) may be determined based on the information on the location of the feature point (or the information on the tilt of the wearable device).

Operations 2340 to 2360 of FIG. 23 and operation 2440 of FIG. 24 may be applied to the present disclosure illustrated in FIG. 25.

Operation 2220 of FIG. 22 may be applied to the method illustrated in FIG. 25 and each of the methods illustrated in FIGS. 23 and 24.

Figure 26:
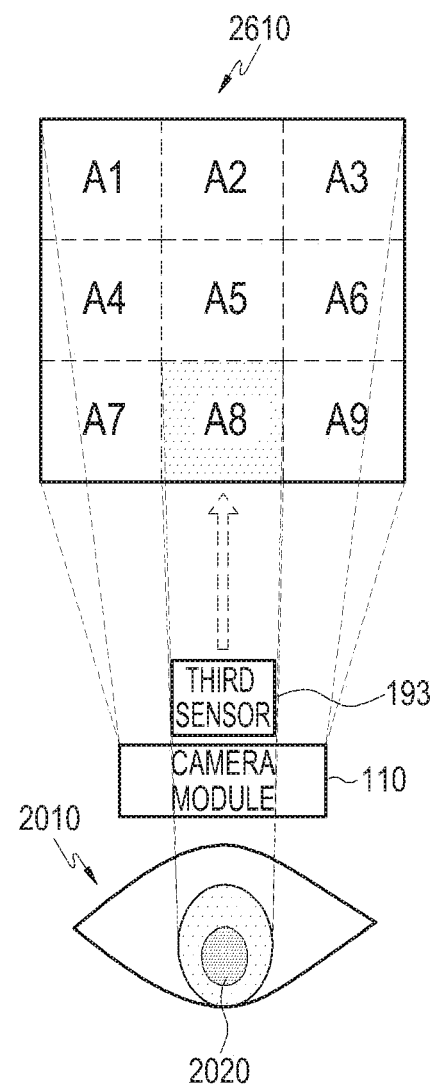
FIG. 26 illustrates a method of providing a virtual image according to an embodiment of the present disclosure.

FIG. 26 illustrates a method of providing a virtual image according to an embodiment of the present disclosure.

Referring to FIG. 26, the processor (for example, the processor 120) of the wearable device (for example, the wearable device 101) may receive a view image generated by photographing a front view 2610 which the user sees from the camera module (for example, the camera module 110).

The processor may recognize an area or an object within the view image. According to this example, it is assumed that the front view 2610 includes areas/objects A1 to A9. The processor recognizes an object/area in an input image. The processor may refer to a database stored in the memory (for example, the memory 130) to recognize the object/area. The processor may detect an image part, which matches an object/area registered in the database, in the view image. Further, the processor may recognize the object/area without referring to the database according to the type of a subject to be recognized. For example, the processor may recognize edge feature points and corner feature points in the view image, and recognize a plane object/area (for example, a quadrangle, a circle, a polygon, or the like) limited by the edge feature points and the corner feature points.

The memory may include a database for storing data or information on an object/area to be recognized and a database for storing data or information on a virtual image to be displayed in the front view 2610. The data on object/area may include an object/area image or information on a feature point of the object/area image (or referred to as a feature image or a feature pattern). The feature point may be an edge, a corner, an image pattern, a contour line, and/or the like. Further, the data on the virtual image may include an image, a text, a dynamic image, location information on the virtual image, mapping information on the object/area, and/or the like. The mapping information may include an identifier or a subject name indicating an object/area to which the virtual image is mapped or with which the virtual image is overlaid.

The processor may acquire an image of an eye 2010 through the first sensor (for example, the first sensor 191) and acquire information on a location of a feature point (for example, iris or pupil 2020) of the eye from the image.

For example, the processor may determine that the user looks at an object/area A8 on the front view based on the location of the pupil 2020.

The processor may acquire, through the third sensor (for example, the third sensor 193), information on a distance between a reference point (for example, the user's eye or the wearable device 101) and the object/area A8 at which the user looks. For example, the third sensor may be installed in the wearable device to be rotated according to a control of the processor or may be configured to control a progress direction (or directivity) of a light (for example, an infrared light or laser) output from the third sensor according to a control of the processor.

The processor may recognize the corresponding object/area (for example, one of the areas/objects A1 to A9) in the front view 2610, at which the user looks, by using the camera module and the first sensor and control the third sensor to radiate a light to the recognized object/area. Further, the processor may control the first and/or second projection type display units (for example, the first and/or second projection type display units 161 and 162) to display a virtual image related to the recognized object/area on the front view 2610.

Figure 27:
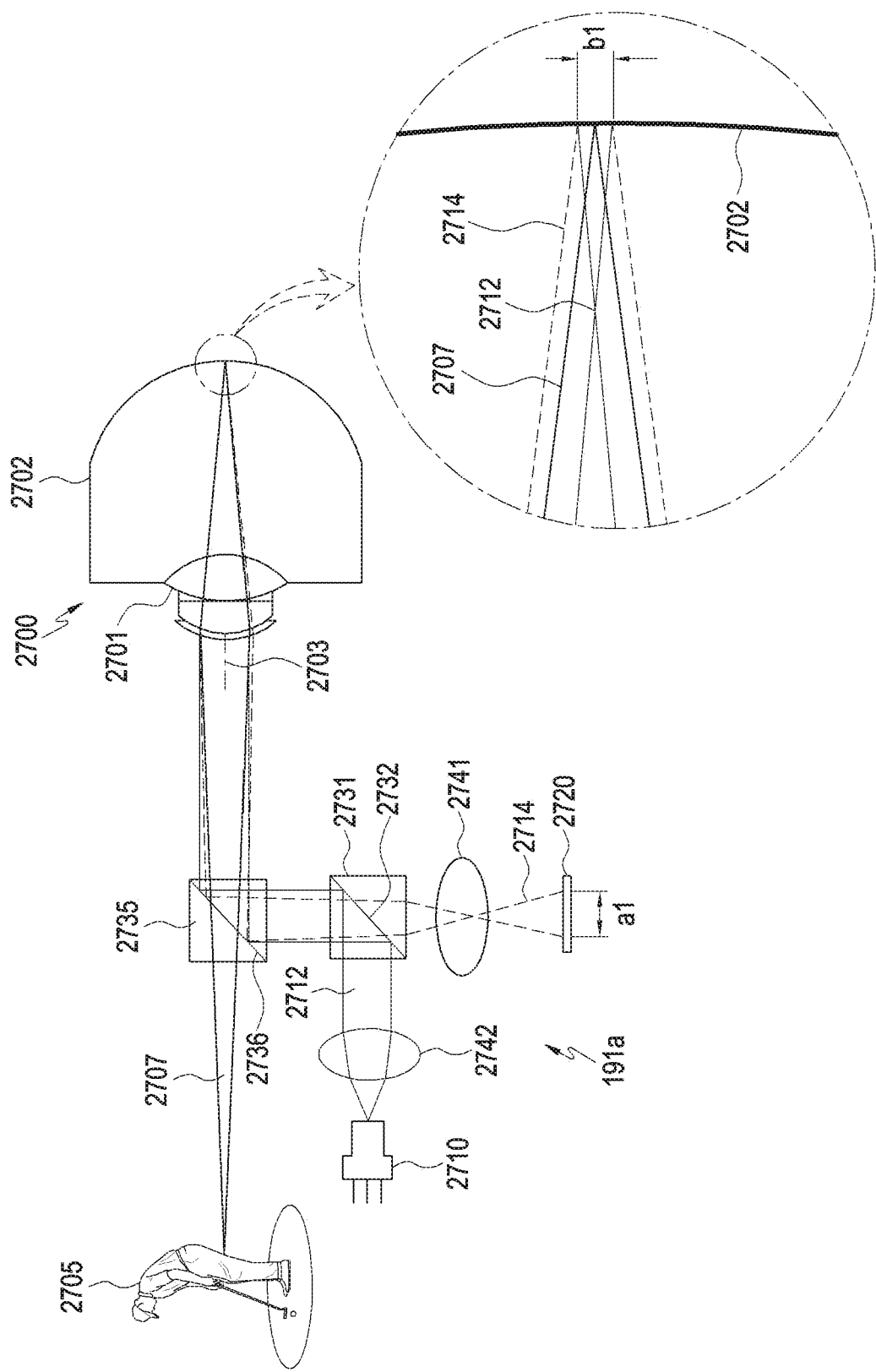
FIG. 27 illustrates a first sensor (or an illumination unit/light receiving unit) according to an embodiment of the present disclosure.

FIG. 27 illustrates a first sensor (or an illumination unit/light receiving unit) according to an embodiment of the present disclosure.

Referring to FIG. 27, at least a part of the first sensor 191a may be disposed inside the first and/or second projection type display units (for example, the first and/or second projection type display units 161 and 162) of the wearable device or may be provided separately from the first and/or second projection type display units.

The first sensor 191a may include an illumination unit 2710 (or a light source) for outputting an illumination light 2712, a light receiving unit 2720 (or an image sensor or an optical detector) for detecting an image of a reflected light 2714, and a first condensing lens 2741 for forming the image of the reflected image 2714. For example, the first sensor 191a may further include a first beam splitter 2731 for outputting the illumination light 2712 (hereinafter, it may be referred to as a test light) to a third beam splitter 2735 corresponding to the light guide element (or a part of the light guide element) and outputting the reflected light 2714 incident from the third beam splitter 2735 to the first condensing lens 2741. For example, the first sensor 191a may further include the third beam splitter 2735 for projecting the illumination light 2712 received from the first beam splitter 2731 onto an eye 2700, projecting a second light 2707 forming the actual view onto the eye 2700, and outputting the reflected light 2714 to the first beam splitter 2731. For example, the first sensor 191a may further include a second condensing lens 2742.

The illumination unit 2710 may output the illumination light 2712. For example, the illumination unit 2710 may output an infrared light. For example, the illumination unit 2710 may output an illumination light having a preset pattern (or an image pattern) (for example, a circle, a quadrangle, a triangle, a polygon, a plurality of points, and/or the like). For example, the illumination unit 2710 may be disposed output the first and/or second projection type display units.

The second condensing lens 2742 may condense and output the illumination light 2712 output from the illumination unit 2710. For example, the second condensing lens 2742 may collimate the illumination light 2712 output from the illumination unit 2710 to be a parallel light.

According to an embodiment of the present disclosure, the second condensing lens 2742 may be included in the illumination unit 2710 or may be omitted.

The first beam splitter 2731 may output the illumination light 2712 to the third beam splitter 2735. The first beam splitter 2731 may be configured to output (or reflect) the illumination light 2712, which has penetrated the second condensing lens 2742, to the third beam splitter 2735 and to output the reflected light 2714 received from the third beam splitter 2735 to the first condensing lens 2741 (or to allow the reflected light 2714 to pass therethrough the first condensing lens 2741). For example, the first beam splitter 2731 may include two triangular prisms which are attached to a reflection surface 2732 (or a reflection layer). For example, the first beam splitter 2731 (or the reflection surface 2732) may be configured to allow a part of the incident light to pass therethrough and to reflect the remaining part of the incident light, configured to allow one polarization component to pass therethrough and to reflect the other polarization component, configured to allow one wavelength component to pass therethrough and to reflect the other wavelength component, or configured to allow one direction light to pass therethrough and to reflect the other direction light.

The third beam splitter 2735 may project the illumination light 2712 onto the user's eye. The third beam splitter 2735 may be configured to project the illumination light 2712 received from the first beam splitter 2731 on the user's eye 2700, to project a second light 2707 received from an object 2705 in front of the wearable device onto the eye 2700 (or to allow the second light 2707 to pass therethrough toward the eye 2700, or to output (or reflect) the light 2714 reflected from the eye 2700 (or a retina 2702 of the eye 2700) to the first beam splitter 2731. For example, the third beam splitter 2735 may include two triangular prisms which are attached to a reflection surface 2736 (or a reflection layer).

The illumination unit 2710 may project the illumination light (for example, infrared light or laser) onto the user's eye, and the light receiving unit 2720 may detect the illumination light reflected from the user's pupils. Further, the light receiving unit 2720 may be one of an infrared camera and a visible light camera.

The eye 2700 of the user includes a crystalline lens 2701 and a retina 2702. The crystalline lens 2701 changes a curvature of the surface thereof (each of the front surface and the rear surface) according to a distance (that is, object distance) of an object 2705 which crystalline lens 2701 desires to focus. The eye focuses on a long distance object when the crystalline lens 2701 changes to be thin (that is, when the curvature of the surface is small), and focuses on a short distance object when the crystalline lens 2701 changes to be thick (that is, when the curvature of the surface is large). The user recognizes an optical image of a front surrounding scene or surrounding environment (that is, a view) formed on the retina 2702.

For example, the user's eye 2700 (or the crystalline lens 2701) focuses on the object 2705, and the crystalline lens 2701 may condense the second light 2707 received according to an optical axis 2703 of the eye 2700 from the object 2705 and form an optical image of the object 2705 on the retina 2702. The crystalline lens 2701 may condense the illumination light 2712, and the illumination light 2712 may be reflected after being incident to some areas of the retina 2702 (that is, a retina reflection surface). For example, when the illumination light 2712 is an infrared light, the user cannot recognize an image of the illumination light 2712. The light 2714 reflected from the retina 2702 may be condensed (or collimated) by the crystalline lens 2701, and the light 2714, which has penetrated the crystalline lens 2701, may be incident to the third beam splitter 2735.

The third beam splitter 2735 may output (or reflect) the light 2714 reflected from the eye 2700 to the first beam splitter 2731.

The first beam splitter 2731 may output the reflected light 2714 received from the third beam splitter 2735 to the first condensing lens 2741 (or may allow the reflected light 2714 to penetrate therethrough toward the first condensing lens 2741).

The first condensing lens 2741 may diffuse (or condense) the reflected light 2714 received from the first beam splitter 2731. The first condensing lens 2741 may form an optical image of the reflected light 2714 received from the first beam splitter 2731 on the light receiving unit 2720.

The light receiving unit 2720 may detect the reflected light 2714 received from the first condensing lens 2741. For example, the light receiving unit 2720 may detect retina image information formed by the reflected light 2714 as an electrical (or digital) image.

For example, the retina image information (for example, at least one piece of size information, area information, location information, pattern information, or brightness (or brightness distribution) information) on the retina image (that is, an image of the retina reflection surface) may be changed according to at least one piece of viewing distance information on the crystalline lens 2701 (for example, distance measurement information using the third sensor (for example the third sensor 193)), object distance information calculated based on focal length information on the crystalline lens, size information on the retina reflection surface calculated based on the retina image information (that is, defocus size), magnification information, refractive power information, curvature (or radius of curvature) information, and thickness information on the crystalline lens.

For example, the size information of the retina reflection surface (that is, defocus size) b1, the retina image (that is, image of the retina reflection surface) size a1, the focal length fe of the crystalline lens 2701, and the focal length fo of the first condensing lens 2741 may have a relation of $b1/a1=fe/fo$.

According to an embodiment of the present disclosure, the first sensor 191a may be disposed inside the first and/or second projection type display units (for example, the first and/or second projection type display units 161 and 162) of the wearable device (for example, the wearable device 101). Since the first and second projection type display units have the same configuration, the configuration of the first projection type display unit will be representatively described below.

Figure 28:
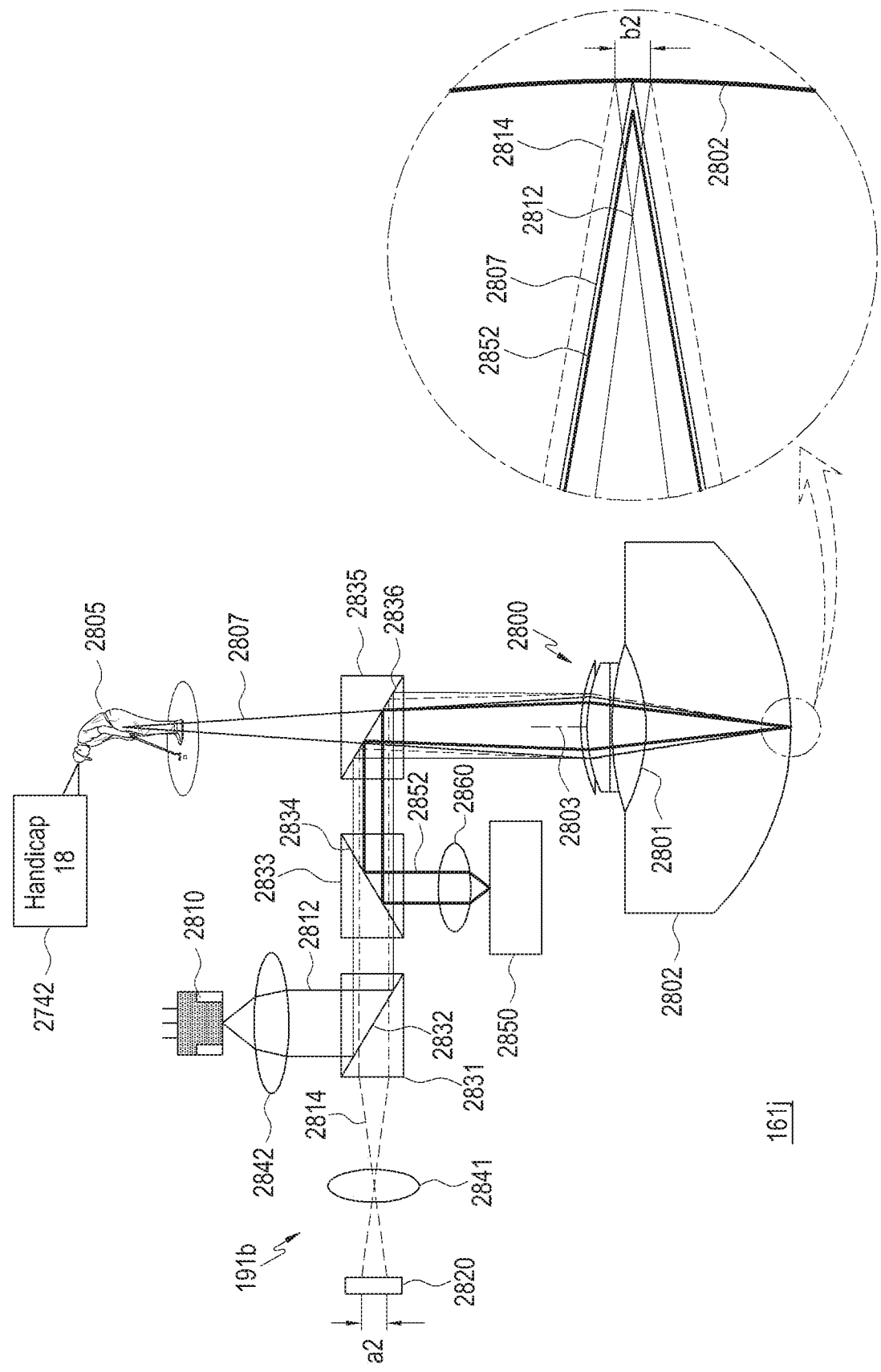
FIG. 28 illustrates a first projection type display unit according to an embodiment of the present disclosure.

FIG. 28 illustrates a first projection type display unit according to an embodiment of the present disclosure.

Referring to FIG. 28, since a first sensor 191*b* illustrated in FIG. 28 may have a similar configuration to that of the first sensor 191*a* illustrated in FIG. 27, an overlapping description will be omitted.

A first projection type display unit 161*j* may include a display element 2850 for outputting a first light 2807 forming a virtual image, a variable lens 2860 arranged on a progress path of the first light 2807 and of which a location or a refraction index is controlled according to a control signal, the first sensor 191*b* for outputting an illumination light 2812, and second and third beam splitters 2833 and 2835 correspond to a light guide element. For example, the second and third beam splitters 2833 and 2835 corresponding to the light guide element may be configured to project the first light 2807 output from the display element 2850 onto an eye 2800, to project the illumination light 2812 output from the first sensor 191*b* onto the eye 2800, and to output the reflected light 2814 to the first sensor 191*b*.

The first sensor 191*b* may include an illumination unit 2810 (or a light source) for outputting the illumination light 2812, a light receiving unit 2820 (or an image sensor or an optical detector) for detecting an image of the reflected light 2814, and a first condensing lens 2841 for forming the image of the reflected image 2814. For example, the first sensor 191*b* may further include a first beam splitter 2831 for outputting the illumination light 2812 to the light guide element (or the second beam splitter 2833), and outputting the reflected light 2814 received from the light guide element (or the second beam splitter 2833) to the first condensing lens 2841. For example, the first sensor 191*b* may further include a second condensing lens 2842.

The illumination unit 2810 may output the illumination light 2812. For example, the illumination unit 2810 may output an infrared light. For example, the illumination unit 2810 may output an illumination light having a preset pattern (or an image pattern) (for example, a circle, a quadrangle, a triangle, a polygon, a plurality of points, and/or the like).

The second condensing lens 2842 may condense and output the illumination light 2812 output from the illumination unit 2810. For example, the second condensing lens 2842 may collimate the illumination light 2812 output from the illumination unit 2810 to be a parallel light. According to an embodiment of the present disclosure, the second condensing lens 2842 may be included in the illumination unit 2810 or may be omitted.

The first beam splitter 2831 may output the illumination light 2812 to the second beam splitter 2833. The first beam splitter 2831 (or a reflection surface 2832 of the first beam splitter 2831) may be configured to output (or reflect) the illumination light 2812, which has penetrated the second condensing lens 2842, to the second beam splitter 2833 and to output the reflected light 2814 received from the second beam splitter 2833 to the first condensing lens 2841 (or to allow the reflected light 2814 to penetrate therethrough toward the first condensing lens 2841).

The display element 2850 may output the first light 2807 forming the virtual image 2742. The display element 2850 may have the form of a quadrangular flat panel. The display element 2850 may display an image in the unit of pixels according to data input from the processor (for example, the processor 120). The display element 2850 may include pixel elements corresponding to the preset resolution and display an image by driving the pixel elements. For example, the display element 2850 may include pixel elements arranged in an M×N (for example, 1190×720, 854×480, and the like) matrix structure. The display element 2850 may be a LED, an OLED, a LCD, a LCOS, and the like.

According to an embodiment of the present disclosure, the variable lens 2860 may include a first penetration surface (for example, the first penetrate surface 241 of the variable lens 240*b*) for allowing a first light 2852 received from the display element 2850 to pass therethrough, a refraction surface (for example, the refraction surface 242 of the variable lens 240*b*) for refracting the first light 2852 having penetrated the first penetration surface, and a second penetration surface (for example, the second penetration surface 243*b* of the variable lens 240*b*) for allowing the first light 2852 having penetrated the refraction surface to pass therethrough. A shape (or form) or curvature of the refraction surface may vary according to a control of the processor. The variable lens 2860 may control a location (or a virtual object distance between the user's eye 2800 and a virtual object) of a virtual image displayed on an actual view (or an optical image of the view) in the front of the wearable device (for example, the wearable device 101) by adjusting an incident angle of the first light 2852 incident to the user's eye 2800 according to a change in the shape (or form) or curvature of the refraction surface.

According to an embodiment of the present disclosure, the variable lens 2860 may include a first sub lens (for example, the first sub lens 245 of the variable lens 240*c*) for primarily refracting the first light 2852 received from the display element 2850 and a second sub lens (for example, the second sub lens 246 of the variable lens 240*c*) for secondarily refracting the primarily refracted first light 2852. A distance between the first and second sub lenses may vary according to a control of the processor. The variable lens 2860 may control a location (or a virtual object distance between the user's eye 2800 and a virtual object) of a virtual image displayed on an actual view (or an optical image of the view) in the front of the wearable device (for example, the wearable device 101) by adjusting an incident angle of the first light 2852 incident to the user's eye 2800 according to a change in the distance between the first and second sub lenses.

The second beam splitter 2833 may output the first light 2812 and the illumination light 2812 to the third beam splitter 2835. The second beam splitter 2833 may be configured to output (or reflect) the first light 2812 received from the variable lens 2860 to the third beam splitter 2835, to output the illumination light 2812 received from the first sensor 191*b* (or the first beam splitter 2831) to the third beam splitter 2835 (or to allow the illumination light 2812 to pass therethrough toward the third splitter 2835), and to output the reflected light 2814 received from the third beam splitter 2835 to the first sensor 191*b* (or the first splitter 2831) (or to allow the reflected light 2814 to pass therethrough toward the first sensor 191*b* (or the first splitter 2831)).

The third beam splitter 2835 may project the first light 2812, the illumination light 2812, and the second light 2807 forming the actual view onto the eye 2800. The third beam splitter 2835 may be configured to project (or reflect) the first light 2812 and the illumination light 2812 received from the second beam splitter 2833 onto the user's eye 2800, to project the second light 2807 received from an object 2805 in front of the wearable device onto the eye 2800 (or to allow the second light 2807 to pass therethrough toward the eye 2800), or to output (or reflect) the light 2814 reflected from the eye 2800 (or a retina 2802 of the eye 2800) to the second beam splitter 2833.

The eye 2800 of the user includes a crystalline lens 2801 and the retina 2802. For example, the user's eye 2800 (or the crystalline lens 2801) focuses on the object 2805, and the crystalline lens 2801 may condense the second light 2807 received according to an optical axis 2803 of the eye 2800 from the object 2805 and form an optical image of the object 2805 on the retina 2802. The crystalline lens 2801 may condense the illumination light 2812, and the illumination light 2812 may be reflected after being incident to some areas of the retina 2802 (that is, a retina reflection surface). For example, when the illumination light 2812 is an infrared light, the user cannot recognize an image of the illumination light 2812. The light 2814 reflected from the retina 2802 may be condensed (or collimated) by the crystalline lens 2801, and the light 2814, which has penetrated the crystalline lens 2801, may be incident to the third beam splitter 2835.

The third beam splitter 2835 may output (or reflect) the light 2814 reflected from the eye 2800 to the second beam splitter 2833.

The second beam splitter 2835 may output the reflected light 2814 received from the second beam splitter 2833 to the first beam splitter 2831 (or may allow the reflected light 2814 to penetrate therethrough toward the first beam splitter 2831).

The first beam splitter 2831 may output the reflected light 2814 received from the second beam splitter 2833 to the first condensing lens 2841 (or may allow the reflected light 2814 to penetrate therethrough toward the first condensing lens 2841).

The first condensing lens 2841 may diffuse (or condense) the reflected light 2814 received from the first beam splitter 2831. The first condensing lens 2841 may form a retina image (that is, an optical image of a retina reflection surface (corresponding to an object of the retina image)) of the reflected light 2814 received from the first beam splitter 2831 on the light receiving unit 2820.

The light receiving unit 2820 may detect the reflected light 2814 received from the first condensing lens 2841. For example, the light receiving unit 2820 may detect the retina image formed by the reflected light 2814 as an electrical (or digital) image.

For example, the retina image information (for example, at least one piece of pixel information on an ISP sensor or the light receiving unit 2820, image size information, image area information, location information, pattern information, and brightness (or brightness distribution) information on the retina image) may be changed according to at least one piece of viewing distance information on the crystalline lens 2801 (for example, distance measurement information using the third sensor (for example the third sensor 193)), object distance information calculated based on focal length information on the crystalline lens, size information on the retina reflection surface calculated based on the retina image information (that is, defocus size), magnification information, refractive power information, curvature (or radius of curvature) information, and thickness information on the crystalline lens.

For example, the size of the retina reflection surface b2, the retina image size a2, the focal length fe2 of the crystalline lens 2801, and the focal length fo of the first condensing lens 2841 may have a relation of b2/a2=fe2/fo.

At least a part (for example, the light receiving unit 2820) of the first sensor 191b may be disposed inside the corresponding projection type display unit to be optically connected to one of the light guide unit 30a of the first projection type display unit 161a illustrated in FIG. 2, the light guide unit 30b of the first projection type display unit 161b illustrated in FIG. 6, the light guide unit 30c of the first projection type display unit 161c illustrated in FIG. 8, the light guide unit 30d of the first projection type display unit 161d illustrated in FIG. 9, the light guide unit 30e of the first projection type display unit 161e illustrated in FIG. 10, the light guide unit 30f of the first projection type display unit 161f illustrated in FIG. 11, the light guide unit 30g of the first projection type display unit 161g illustrated in FIG. 13, the light guide unit 30h of the first projection type display unit 161h illustrated in FIG. 14, and the light guide unit 30i of the first projection type display unit 161i illustrated in FIG. 15.

For example, the first beam splitter 2831 (or the reflection surface 2832 of the first beam splitter 2831) may be disposed to face one of the second surface 222 of the light guide element 220a illustrated in FIG. 2, the second surface 222 of the light guide element 220a illustrated in FIG. 6, the second surface 222 of the light guide element 220b illustrated in FIG. 8, the second surface 222 of the light guide element 220c illustrated in FIG. 9, the second surface 222 of the light guide element 30e illustrated in FIG. 10, the second surface 222 of the light guide element 220a illustrated in FIG. 11, the second surface 222 of the light guide element 220b illustrated in FIG. 13, the second surface 222 of the light guide element 220c illustrated in FIG. 14, and the second surface 222 of the light guide element 220d illustrated in FIG. 15.

Figure 29:
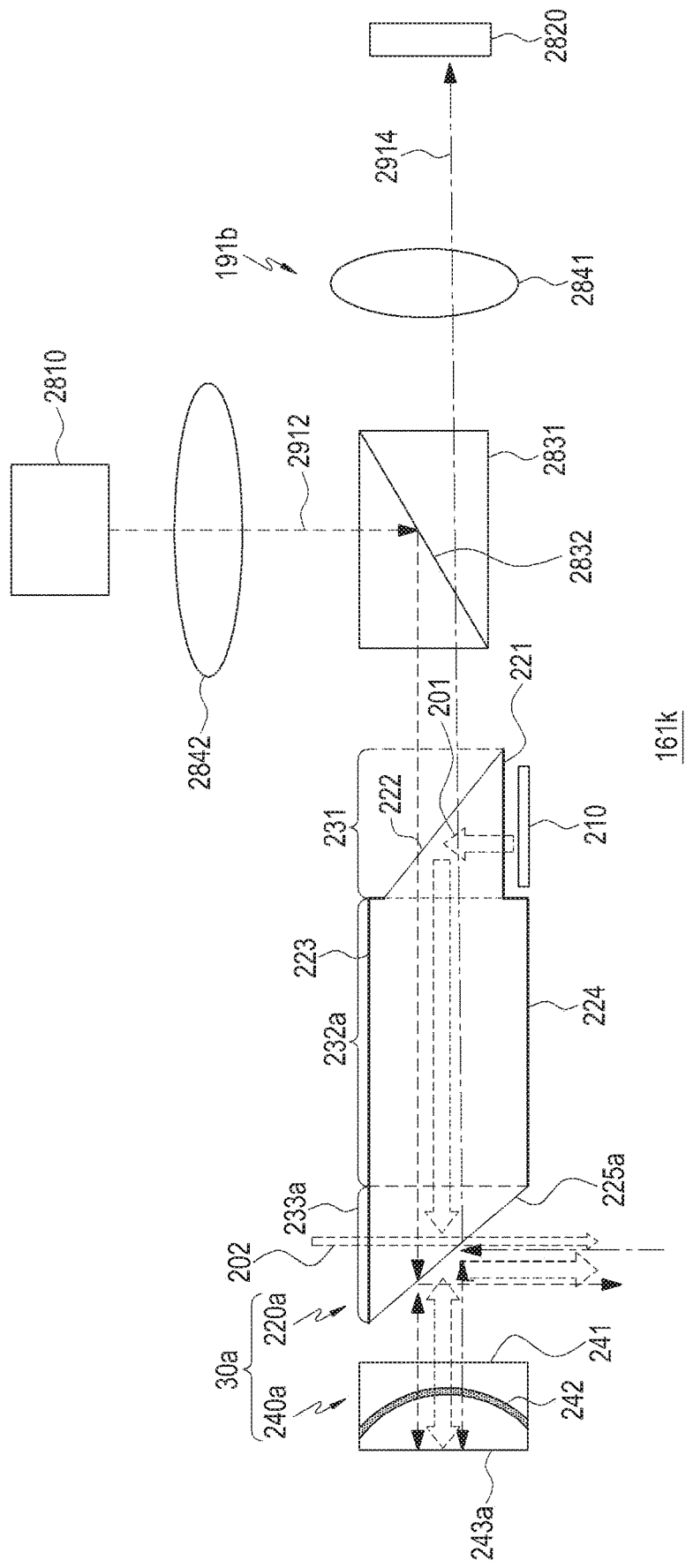
FIG. 29 illustrates a first projection type display unit according to an embodiment of the present disclosure.

FIG. 29 illustrates a first projection type display unit according to an embodiment of the present disclosure.

Referring to FIG. 29, since the first projection type display unit 161k has a configuration in which the light guide unit 30a of the first projection type display unit 161a illustrated in FIG. 2 is optically connected to the first sensor 191b illustrated in FIG. 28, an overlapping description will be omitted.

The first projection type display unit 161k may include the display element 210, the light guide unit 30a, and the first sensor 191b. The light guide unit 30a may include the light guide element 220a and the variable lens 240a. Similarly, the second projection type display unit may include a display element and a light guide unit, and the light guide unit may include a light guide element and a variable lens.

The display element 210 may output the first light 201 forming an image to the light guide element 220a.

The light guide element 220a may include first to fifth surfaces 221 to 225a. The light guide element 220a may guide the first light 201 received from the display element 210 through internal reflection (or internal total reflection) toward the variable lens 240a.

The first surface 221 may correspond to a part of the rear surface of the light guide element 220a facing the display element 210, and may allow the first light 201 received from the display element 210 to penetrate toward the second surface 222.

The second surface 222 corresponds to a first side surface of the light guide element 220a located between the first and third surfaces 221 and 223, and may reflect the first light 201 penetrating the first surface 221 toward the third or fourth surface 223 or 224.

The third surface 223 corresponds to the front surface of the light guide element 220a facing the first window 90, the fourth surface 224 corresponds to the remaining part of the rear surface of the light guide element 220a facing the user, and the third and fourth surface 223 and 224 may reflect (or totally reflect) the received first light 201 to make the first light 201 reach the fifth surface 225a. The total reflection means that the first light 201 incident to a boundary surface between the light guide element 220a and an external air layer (that is, the third or fourth surface 223 or 224) from the inside of the light guide element 220a is totally reflected from the boundary surface.

The fifth surface 225a corresponds to a second side surface of the light guide element 220a located between the third and fourth surfaces 223 and 224, and may penetrate the received first light 201 toward the variable lens 240a and reflect the first light 201 received from the variable lens 240a toward the user's eye. The fifth surface 225a may allow the second light 202 forming a front view (or an optical image of the view) of the electronic device (for example, the wearable device 101) to pass therethrough toward the user's eye.

The light guide element 220a may include a body part 232a between the third and fourth optical surfaces 223 and 224 having a uniform thickness, a first inclined part 231 between the first and second surfaces 221 and 222, of which the thickness gradually decrease from one end thereof (or from one end of the body part 232a) to the other end thereof, and a second inclined part 233a between the third and fourth surfaces 223 and 224, of which the thickness gradually decrease from one end thereof (or from the other end of the body part 232a) to the other end thereof. The second inclined part 233a may have the fifth surface 225a corresponding to a slope which faces the variable lens 240a and the user's eye.

The variable lens 240a may include a penetration surface 241 for penetrating the received first light 201, a refraction surface 242 for refracting the received first light 201, and a reflection surface 243a for reflecting the received first light 201. A shape (or form) or curvature of the refraction surface 242 may vary according to a control of the processor. The variable lens 240a may control a location (or a virtual object distance between the user's eye and a virtual object) of a virtual image displayed on an actual view (or an optical image of the view) in the front of the wearable (for example, the wearable device 101) by adjusting an angle of the first light 201 (that is, an incident light) incident to the user's eye according to a change in the shape (or form) or curvature of the refraction surface 242.

The change in the refractive power of the variable lens 240a and the location of the virtual image displayed on the actual view may have a relation of $1/u+1/v=1/f$, where u denotes a distance between the variable lens 240a and the display element 210 (for example, an LED, an OLED, an LCD, an LCOS, and the like), v denotes a distance between the variable lens 240a and the virtual image, and f denotes a focal length of the variable lens 240a.

The illumination unit 2810 may output an illumination light 2912.

The second condensing lens 2842 may condense and output the illumination light 2810 output from the illumination unit 2912. For example, the second condensing lens 2842 may collimate the illumination light 2912 output from the illumination unit 2810 to be a parallel light.

The first beam splitter 2831 may output the illumination light 2912 toward the second surface 222 of the light guide element 220a. The illumination light 2912 output from the first beam splitter 2831 may penetrate the second surface 222 to be incident to the light guide element 220a, and may penetrate the fifth surface 225a to be output toward the variable lens 240a.

The illumination light 2912 output from the light guide element 220a may penetrate the penetration surface 241 and the refraction surface 242 of the variable lens 240a to be incident to the reflection surface 243a, and the illumination light 2912 reflected from the reflection surface 243a may penetrate the penetration surface 241 and the refraction surface 242 to be output toward the fifth surface 225a. The fifth surface 225a may reflect the illumination light 2912 received from the variable lens 240a toward the user's eye.

A light 2914 reflected from the eye (or the retina of the eye) may be reflected by the fifth surface 225a and the variable lens 240a, and may penetrate the fifth surface 225a and the second surface 222 to be input to the first beam splitter 2831.

The first beam splitter 2831 may output the reflected light 2914 received from the light guide element 220a to the first condensing lens 2841 (or may allow the reflected light 2914 to penetrate the first condensing lens 2841).

The first condensing lens 2841 may diffuse (or condense) the reflected light 2814 received from the first beam splitter 2831.

The light receiving unit 2820 may detect the reflected light 2914 received from the first condensing lens 2841. For example, the light receiving unit 2820 may detect the retina image formed by the reflected light 2914 as an electrical (or digital) image.

Figure 30:
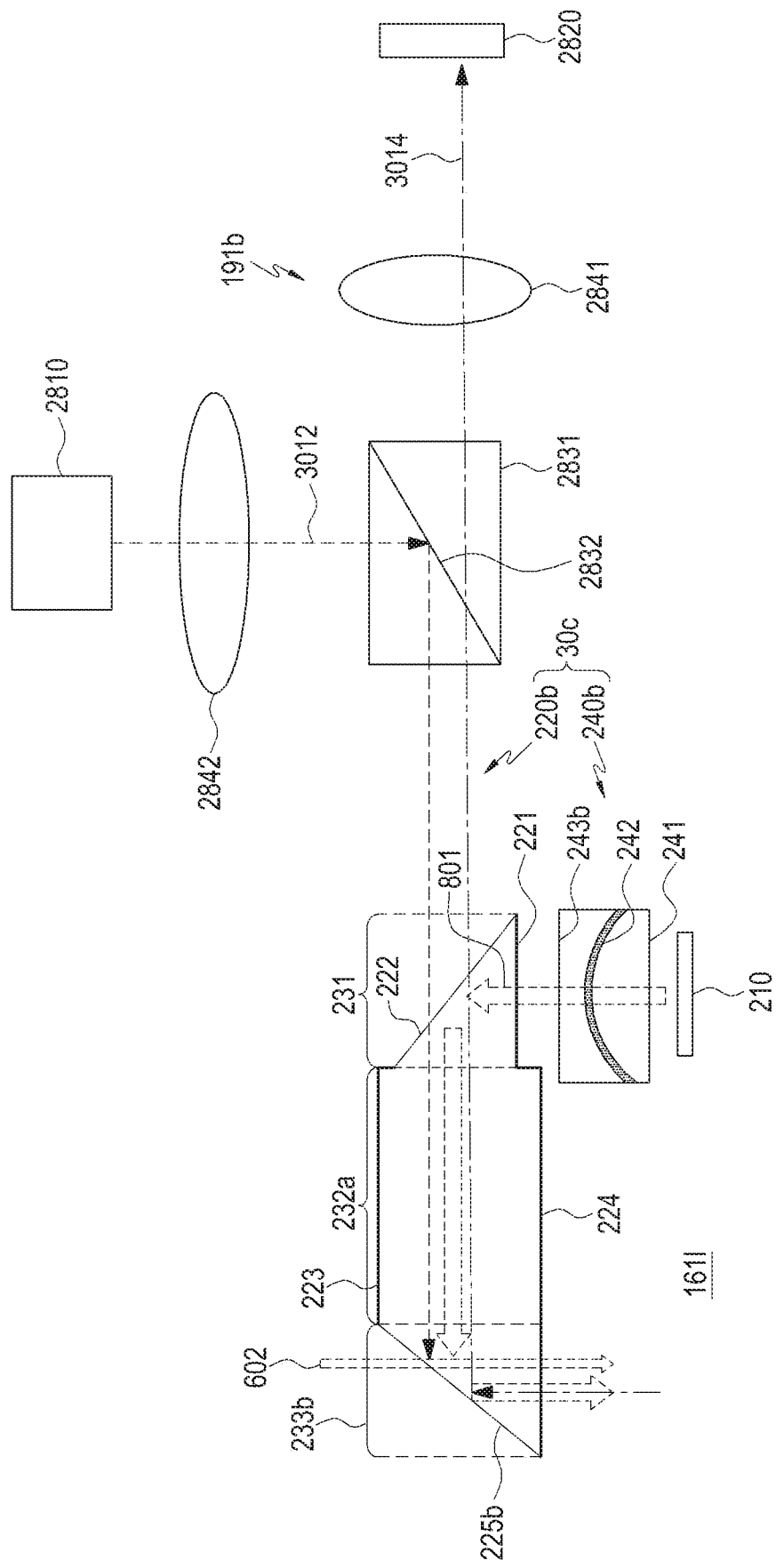
FIG. 30 illustrates a first projection type display unit according to an embodiment of the present disclosure.

FIG. 30 illustrates a first projection type display unit according to an embodiment of the present disclosure.

Referring to FIG. 30, since the first projection type display unit 161*l* has a configuration in which the light guide unit 30c of the first projection type display unit 161c illustrated in FIG. 8 is optically connected to the first sensor 191b illustrated in FIG. 28, an overlapping description will be omitted.

The first projection type display unit 161*l* may include the display device 210 and the light guide unit 30c. The light guide unit 30c may include the light guide element 220b, and the variable lens 240b.

The fifth surface 225b corresponds to a second side surface of the light guide element 220b located between the third and fourth surfaces 223 and 224, and may reflect the incident first light 801 toward the user's eye. The fifth surface 225b may allow the second light 602 forming a front view (or an optical image of the view) of the wearable device 101 to pass therethrough toward the user's eye.

The light guide element 220b may include the body part 232a between the third and fourth optical surfaces 223 and 224 having a uniform thickness, the first inclined part 231 between the first and second surfaces 221 and 222, of which the thickness gradually decrease from one end thereof (or from one end of the body part 232a) to the other end thereof, and a second inclined part 233b between the third and fourth surfaces 223 and 224, of which the thickness gradually decrease from one end thereof (or from the other end of the body part 232a) to the other end thereof. The second inclined part 233b may have the fifth surface 225b corresponding to an inclined surface facing the view in the front of the wearable device 101.

The variable lens 240b may include the first penetration surface 241 for penetrating the first light 801 received after being output from the display element 210, the refraction surface 242 for refracting the first light 801 having penetrated the first penetration surface 241, and the second penetration surface 243b for penetrating the first light 801 having penetrated the refraction surface 242. A shape (or form) or curvature of the refraction surface 242 may vary according to a control of the processor. The variable lens 240b may control a location (or a virtual object distance between the user's eye and a virtual object) of a virtual image displayed on an actual view (or an optical image of the view) in the front of the wearable device (for example, the wearable device 101) by adjusting an incident angle of the first light 801 incident to the user's eye according to a change in the shape (or form) or curvature of the refraction surface 242.

The illumination unit 2810 may output an illumination light 3012.

The second condensing lens 2842 may condense and output the illumination light 3012 output from the illumination unit 2810. For example, the second condensing lens 2842 may collimate the illumination light 3012 output from the illumination unit 2810.

The first beam splitter 2831 may output the illumination light 3012 toward the second surface 222 of the light guide element 220b. The illumination light 3012 output from the first beam splitter 2831 may penetrate the second surface 222 to be incident to the light guide element 220b, and may be reflected by the fifth surface 225a to be output toward the user's eye.

A light 3014 reflected from the eye (or the retina of the eye) may be reflected by the fifth surface 225a, and may penetrate the fifth surface 225a and the second surface 222 to be input to the first beam splitter 2831.

The first beam splitter 2831 may output the reflected light 3014 received from the light guide element 220a to the first condensing lens 2841 (or may allow the reflected light 3014 to penetrate therethrough toward the first condensing lens 2841).

The first condensing lens 2841 may diffuse (or condense) the reflected light 3014 received from the first beam splitter 2831.

The light receiving unit 2820 may detect the reflected light 3014 received from the first condensing lens 2841. For example, the light receiving unit 2820 may detect the retina image formed by the reflected light 3014 as an electrical (or digital) image.

Figure 31:
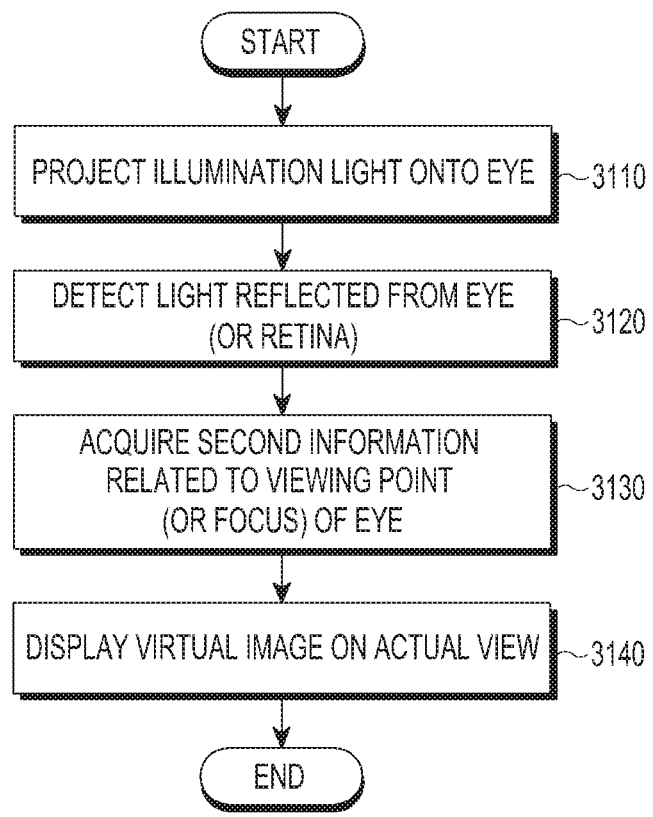
FIG. 31 is a flowchart illustrating a method of providing a virtual image according to various embodiments according to an embodiment of the present disclosure.

FIG. 31 is a flowchart illustrating a method of providing a virtual image according to an embodiment of the present disclosure.

Referring to FIG. 31, the method of providing the virtual image may include operations 3110 to 3140.

In operation 3110, the processor (for example, the processor 120) of the wearable device (for example, the wearable device 101) may be configured to project an illumination light onto the user's eye through the sensor (for example, the first sensor 191, 191a, or 191b) (or through the projection type display unit (for example, the projection type display unit 161j, 161k, or 161l)).

In operation 3120, the processor may be configured to detect a light reflected from the eye (or the retina of the eye) through the sensor or the projection type display unit.

In operation 3130, the processor may be configured to acquire viewing distance information related to a viewing point of the eye based on retina image information on the detected light.

According to an embodiment of the present disclosure, the processor may determine whether a location of an eye feature point (for example, iris or pupil) is fixed for a preset threshold time, and, when the location of the feature point is fixed for the preset threshold time, perform at least one of operations 3110, 3120, and 3130.

According to an embodiment of the present disclosure, the retina image information may include at least one piece of size information, area information, location information, pattern information, and brightness (or brightness distribution) information on an image of the light detected from the light receiving unit when the illumination light projected toward the pupil is reflected from the retina. For example, each piece of the information may include a corresponding value, a corresponding range, or a corresponding level (or an identifier/code indicating one of them).

According to an embodiment of the present disclosure, the viewing distance information may include at least one piece of distance measurement information using the third sensor (for example, the third sensor 193), focal length information, magnification information, refractive power information, the curvature (or radius of curvature) information, and thickness information on the crystalline lens. For example, each piece of the information may include a corresponding value, a corresponding range, or a corresponding level (or an identifier/code indicating one of them).

In operation 3140, the processor may display a virtual image (or a virtual object) on the actual view through the projection type display unit to place the virtual image on a location corresponding to the viewing distance information.

Referring to FIG. 21, the processor may display the virtual images 2131, 2132, and 2133 having virtual object distances (for example, distances between the user's eye and the virtual object) corresponding to the viewing distance information on the actual view including the actual objects 2111, 2112, and 2113. The following description is made based on the first projection type display unit 161a illustrated in FIG. 2 as an example. The processor may control the virtual object distance between the user's eye and the virtual object 2131, 2133, or 2133 recognized by the user to correspond to the viewing distance information by changing the variable lens 240a (or by changing a curvature of the refraction surface 242 of the variable lens 240a) to adjust an incident angle of the light 2121, 2122 or 2123 incident to the user's eye.

Figure 35:
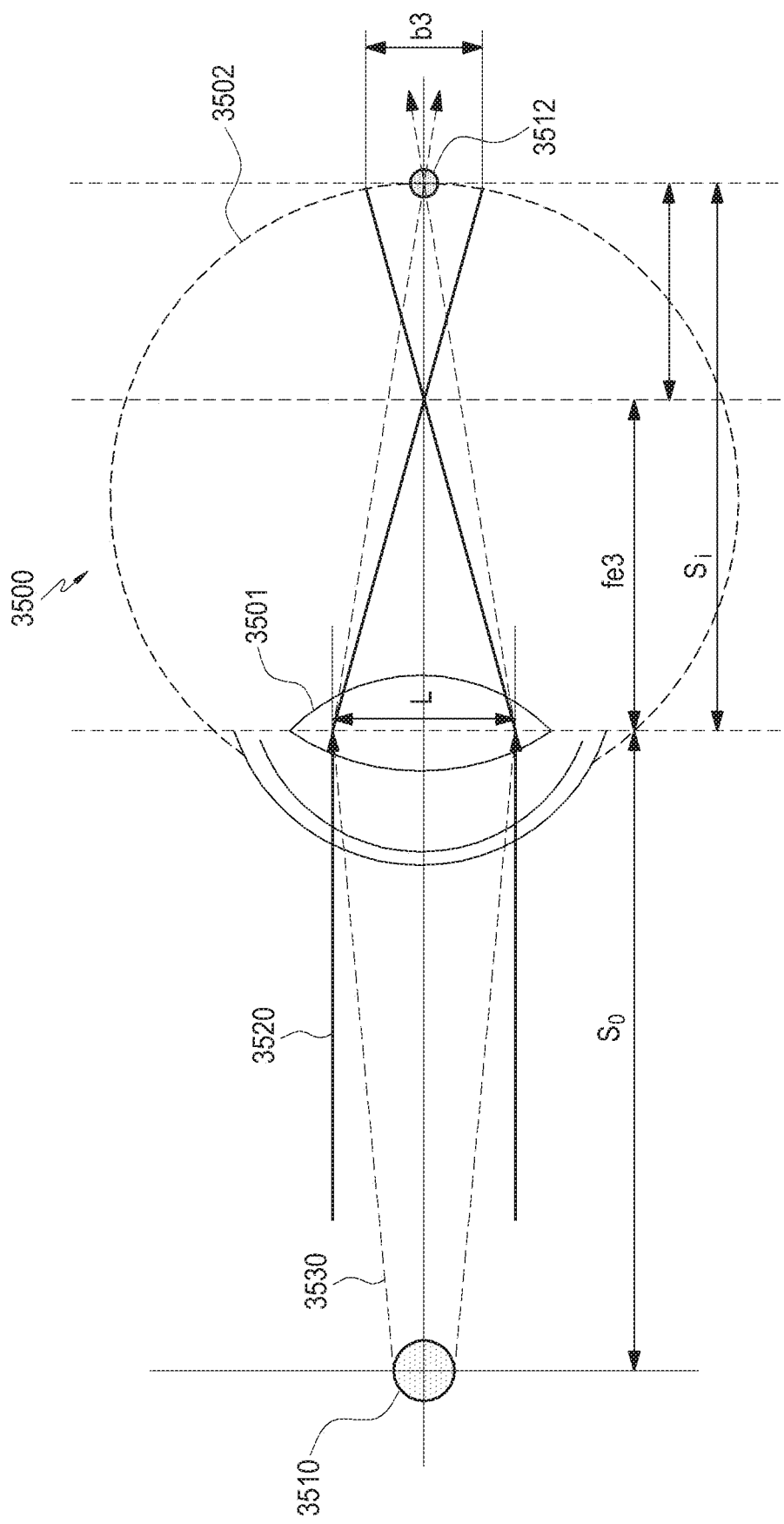
FIG. 35 illustrates a method of determining a viewing distance using an illumination light according to an embodiment of the present disclosure.

FIG. 35 illustrates a method of determining a viewing distance using an illumination light according to an embodiment of the present disclosure.

Referring to FIG. 35, a visible light 3530 starting from an object 3510 may converge by a crystalline lens 3501, and the converging visible light 3530 may form an image 3512 of the object 3510 on the retina.

For example, size information on a retina reflection surface 3502 related to an illumination light 3520 (that is, defocus size) b3, a size a3 of a retina image corresponding to an image of a part (that is, the retina reflection surface 3502) of an eye 3500, a focal length fe3 of the crystalline line 3501, a first condensing lens (for example, the first condensing lens 2741), and a focal length fo of the first condensing lens 2841 may have a relation of b3/a3=fe3/fo.

The focal length of the crystalline lens 3501 may be defined as a distance on which the image is focused after a parallel light (illumination light) penetrates the crystalline lens. Further, a pupil size L, an object distance So corresponding to a distance between the crystalline lens 3501 and the object 3510, a focal length fe3 of the crystalline lens 3501, an ID Si corresponding to a distance between the crystalline lens 3501 and the retina, and size information on the retina reflection surface 3502 (defocus size) b3 may have a relation of b3=L(Si/fe3−1) based on a triangle proportion rule. Referring to the two equations, the retina image size a3 and the focal length fe3 may have a relation of a3=Lfo/fe3 (Si/fe3−1).

For example, referring to Rossi, L., et al., "Pupil Size under Different Lighting Sources," Proceedings of CIE 2012 'Lighting Quality and Energy Efficiency', the pupil size L may have a value from 2.5 mm to 7 mm in a general case of an adult according to illumination based on a relation between the pupil size and the illumination. The processor (for example, the processor 120) may determine the pupil size L based on information on an amount or an intensity of the light detected using the illumination sensor (for example, the illumination sensor 194). For example, by using an ID (Si=17 mm) according to reduced schematic eye of Gull-Strand, the processor may acquire the focal length fe3 corresponding to the retina image size a3. Further, the processor may acquire the object distance So based on a lens formula of 1/So+1/Si=1/fe3. The processor may calculate a value of the object distance So based on the focal length fe3 by using the above equations.

FIGS. 32A, 32B, 32C, and 32D illustrate a method of providing a virtual image according to various embodiments.

Referring to FIG. 32A, actual objects of different distances which the user views are illustrated. For example, a first actual object 3211 is located within a first distance range (for example, a short distance range from 0 to 1 m) from the user, a second actual object 3212 is located within a second distance range (for example, a middle distance range from 1 m to 5 m) from the user, and a third actual object 3213 is located with a third distance range (for example, a long distance range from 5 m to infinity) from the user.

Referring to FIG. 32B, modified examples of the crystalline lens according to a distance of an object which the user views are illustrated. For example, at least one of a magnification, refractive power, curvature information, and thickness of the crystalline lens decreases in an order of a first modified example 2802a, a second modified example 2802b, and a third modified example 2802c of the crystalline lens as the distance of the object which the user views increases.

Referring to FIG. 32C, a change in an incident angle and an exit angle of the light incident to and output from the first condensing lens 2841 according to the change in the crystalline lens is illustrated.

For example, as the distance of the object which the user views increases (or at least one of the magnification, refractive power, curvature information, and thickness of the crystalline lens decreases), the incident angle gradually decreases and the exit angle gradually increases in an order of a first modified example 2814a, and a second modified example 2814b, and a third modified example 2814c of the reflected light.

Referring to FIG. 32D, an image change of the reflected light detected by the image sensor 2820 according to the change in the incident angle (or exit angle) of the reflected light incident to the first condensing lens 2841 is illustrated.

For example, as the distance of the object which the user views increases (or at least one of the magnification, refractive power, curvature information, and thickness of the crystalline lens decreases or the exit angle of the reflected light output from the first condensing lens 2841 increases), the image size (or area) may decrease (or the center brightness may increase) in an order of a first image 3221, a second image 3222, and a third image 3223. For example, as the distance of the object which the user views increases, a location or a pattern of the image of the reflected light detected by the image sensor 2820 may change.

According to an embodiment of the present disclosure, the processor may be configured to detect pupil size information corresponding to light intensity information measured by the illumination sensor in a table pre-stored in the electronic device.

As shown in Table 1 below, a first table (or database) pre-stored in the electronic device may store a plurality of pieces of information in the form of a plurality of records.

TABLE 1

| Record number | Light intensity (amount) information | Pupil size information |
|---|---|---|
| A1 | E1 | F1 |
| A2 | E2 | F2 |
| A3 | E3 | F3 |
| ... | ... | ... |

Each record Ai ($1 \leq i \leq n$, n is an integer larger than or equal to 1) includes fields, such as light intensity information Ei and pupil size information Fi. The light intensity information Ei may include at least one of the intensity, luminance, and candela of the light detected by the illumination sensor.

According to an embodiment of the present disclosure, the processor may be configured to determine the viewing distance information corresponding to the retina image information based on the table (or database) pre-stored in the electronic device.

According to an embodiment of the present disclosure, the processor may be configured to detect the viewing distance information corresponding to the retina image information in the table (or database) pre-stored in the electronic device.

As shown in Table 2 below, a second table (or database) pre-stored in the electronic device may store a plurality of pieces of information in the form of a plurality of records.

TABLE 2

| Record number | Retina image information | Viewing distance information |
|---|---|---|
| A1 | B1 | C1 |
| A2 | B2 | C2 |
| A3 | B3 | C3 |
| ... | ... | ... |

Each record Ai ($1 \leq i \leq n$, n is an integer larger than or equal to 1) includes fields, such as retina image information Bi and viewing distance information Ci. The retina image information Bi may include at least one of a size, an area, a location (or a center location or coordinate), a pattern (for example, circle, oval, a width/length ratio, and a major axis/minor axis ratio), and brightness (or brightness distribution) of the image of the reflected light detected by the image sensor. For example, each piece of the retina image information Bi may include a corresponding value, a corresponding range, or a corresponding level (or an identifier/code indicating one of them). The viewing distance information Ci may include at least one piece of distance measurement information using a third sensor (for example, the third sensor 193), object distance information calculated based on focal distance information on the crystalline lens, size information on the retina reflective surface (that is, some areas of the retina where the illumination light is incident and reflected) calculated based on the retina image information (that is, defocus size), magnification information, refractive power information, curvature (or radius of curvature) information, and thickness information on the crystalline lens. For example, each piece of the viewing distance information Ci may include a corresponding value, a corresponding range, or a corresponding level (or an identifier/code indicating one of them).

According to an embodiment of the present disclosure, the processor may be configured to detect first values corresponding to the retina image information in the table (or database) pre-stored in the electronic device. The processor may be configured to calculate the viewing distance information from second values of the table corresponding to the first values.

For example, when values B1 and B2 close to the retina image information are detected in the first table (or database), the processor may determine a middle/average value between the values B1 and B2 as the viewing distance information.

Figure 33:
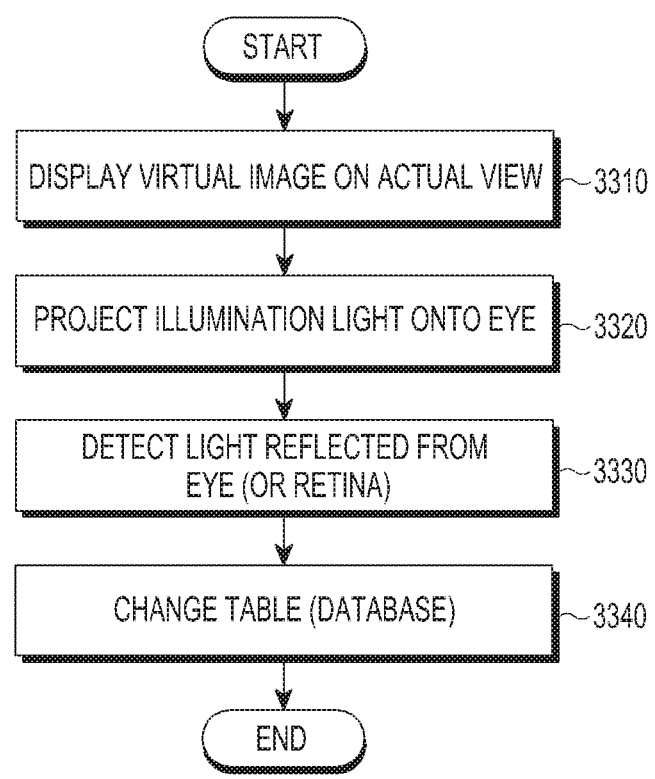
FIG. 33 is a flowchart illustrating a method of providing a virtual image according to an embodiment of the present disclosure.

FIG. 33 is a flowchart illustrating a method of providing a virtual image according to an embodiment of the present disclosure.

Referring to FIG. 33, the method of providing the virtual image may include operations 3310 to 3340.

In operation 3310, the processor (for example, the processor 120) of the wearable device (for example, the wearable device 101) may be configured to display a virtual image (or a virtual object) having already known viewing distance information on the actual view through the projection type display unit (for example, the projection type display unit 161*j*, 161*k*, or 161*l*).

Referring to FIG. 21, the processor may display the virtual image 2131, 2132, or 2133 (for example, image describing the actual object) having a virtual object distance (for example, distance between the user's eye and the virtual object) corresponding to the viewing distance information on the actual view including the actual object 2111, 2112, or 2113.

In operation 3320, the processor may be configured to project an illumination light onto the user's eye through the sensor (for example, the first sensor 191, 191*a*, or 191*b*) (or through the projection type display unit).

In operation 3330, the processor may be configured to detect a light reflected from the eye (or the retina of the eye) through the sensor (for example, the first sensor 191, 191*a*, or 191*b*).

In operation 3340, the processor may be configured to change the table (or database) pre-stored in the electronic device based on the retina image information on the detected light and the already known viewing distance information.

For example, when the information B1 corresponding to the already known viewing distance information C1 is different from the retina image information with respected to the detected light (for example, value (B1-1)) in the first table (or database), the processor may change B1 into B1-1.

Figure 34:
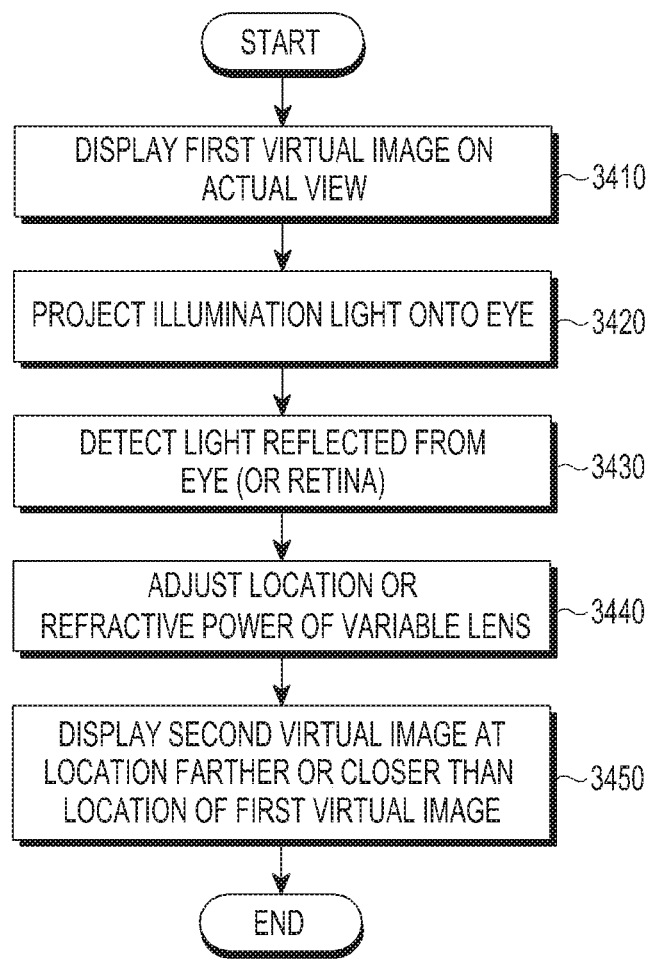
FIG. 34 is a flowchart illustrating a method of providing a virtual image according to an embodiment of the present disclosure.

FIG. 34 is a flowchart illustrating a method of providing a virtual image according to an embodiment of the present disclosure.

Referring to FIG. 34, the method of providing the virtual image may include operations 3410 to 3430.

In operation 3410, the processor (for example, the processor 120) of the wearable device (for example, the wearable device 101) may be configured to display a first virtual image on an actual view (or an optical image of the view) in the front of the wearable device through the projection type display unit (for example, the first projection type display unit 161*j*, 161*k*, or 161*l*).

For example, the processor may display the first virtual image on a location corresponding to a location of a first object within the actual view (for example, a location identical to or close to the location of the first object within the actual view) through the projection type display unit.

In another example, the processor may display the first virtual image at a preset location within the actual view through the projection type display unit.

In operation 3420, the processor may be configured to project an illumination light onto the user's eye through the sensor (for example, the first sensor 191, 191*a*, or 191*b*) (or through the projection type display unit).

In operation 3430, the processor may be configured to detect a light reflected from the eye (or the retina of the eye) through the sensor or the projection type display unit.

In operation 3440, the processor may adjust a location or refractive power of the variable lens (for example, the variable lens 2860, 240*a*, 240*b*, 240*c*, 240*d*, or 240*e*) within the projection type display unit.

For example, when the first object and/or the wearable device moves, the processor may adjust the location or the refractive power of the variable lens within the projection type display unit according to the changed location of the first object.

In another example, when it is detected that the user looks at a second object within the actual view, which is different from the first object, the processor may adjust the location or the refractive power of the variable lens 240*a*, 240*b*, 240*c*, 240*d*, or 240*e* within the projection type display unit according to a change in the viewing point.

According to an embodiment of the present disclosure, the processor may adjust the location or the refractive power of the variable lens based on retina image information or viewing distance information with respect to the detected light.

According to an embodiment of the present disclosure, the retina image information may include at least one piece of size information, area information, location information, pattern information, and brightness (or brightness distribution) information on an image of the light. For example, each piece of the information may include a corresponding value, a corresponding range, or a corresponding level (or an identifier/code indicating one of them).

According to an embodiment of the present disclosure, the viewing distance information may include at least one piece of distance measurement information using a third sensor (for example, the third sensor 193), object distance information calculated based on focal distance information on the crystalline lens, size information on the retina reflective surface (that is, some areas of the retina where the illumination light is incident and reflected) calculated based on the retina image information (that is, defocus size), magnification information, refractive power information, curvature (or radius of curvature) information, and thickness information on the crystalline lens. For example, each piece of the information may include a corresponding value, a corresponding range, or a corresponding level (or an identifier/code indicating one of them).

According to an embodiment of the present disclosure, the processor may be configured to determine control information on the variable lens corresponding to the retina image information based on the table (or database) pre-stored in the electronic device.

According to an embodiment of the present disclosure, the processor may be configured to detect control information corresponding to the retina image information in the table (or database) pre-stored in the electronic device.

As shown in Table 3 below, a second table (or database) pre-stored in the electronic device may store a plurality of pieces of information in the form of a plurality of records.

TABLE 3

| Record number | Retina image information | Viewing distance information | Control information |
|---|---|---|---|
| A1 | B1 | C1 | D1 |
| A2 | B2 | C2 | D2 |
| A3 | B3 | C3 | D3 |
| ... | ... | ... | ... |

Each record Ai (1≤i≤n, n is an integer larger than or equal to 1) includes fields, such as retina image information Bi and viewing distance information Ci. The retina image information Bi may include at least one of a size, an area, a location (or a center location or coordinate), a pattern (for example, circle, oval, a width/length ratio, and/or a major axis/minor axis ratio), and brightness (or brightness distribution) of the image of the reflected light detected by the image sensor. For example, each piece of the retina image information Bi may include a corresponding value, a corresponding range, or a corresponding level (or an identifier/code indicating one of them). The viewing distance information Ci may include at least one piece of object distance information calculated based on focal distance information on the crystalline lens, size information on the retina reflective surface (that is, some areas of the retina where the illumination light is incident and reflected) calculated based on the retina image information (that is, defocus size), magnification information, refractive power information, curvature (or radius of curvature) information, and thickness information on the crystalline lens. For example, each piece of the viewing distance information Ci may include a corresponding value, a corresponding range, or a corresponding level (or an identifier/code indicating one of them). The control information Di may indicate the type/content of the control information (for example, a form of the refraction surface, a curvature change, and/or a location movement of the variable lens), a value, a level, a code, and an identifier of particular control information (for example, value/value range/code of a voltage, a current, a voltage/current applying time, a voltage/current waveform for the shape (or form) of the refraction surface, the curvature change of the refraction surface, and/or the location movement of the variable lens, identification information on a particular file, and/or the like). For example, the control information Di may include a corresponding value, a corresponding range, or a corresponding level (or an identifier/code indicating one of them).

In operation 3450, the processor may display a second virtual image at a location, which is farther or closer than the location of the first virtual image, through a control of the projection type display unit.

For example, when the first object and/or the wearable device moves, the processor may display the second virtual image at a location corresponding to the changed location of the first object (for example, a location identical or close to the location of the first object within the actual view) through the projection type display unit. In this case, the second virtual image may be the same as the first image, differing only in the location.

In another example, when it is detected that the user looks at the second object within the actual object, which is different from the first object, the processor may display the second virtual image at a location corresponding to the location of the second object (for example, a location identical or close to the location of the second object within the actual view) through the projection type display unit. In this case, the second virtual image may have the content and location different from those of the first virtual image or may have the content identical to that of the first virtual image, differing only in the location.

According to various embodiments of the present disclosure, a method of outputting a virtual image by a wearable device may include radiating a light to eye of a user (or a wearer), acquiring retina image information by receiving a light which is reflected from a retina as the radiated light passes through a crystalline lens, calculating a focal length of the crystalline lens based on the acquired retina image information, and determining a viewing distance of the user based on the calculated focal length.

According to various embodiments of the present disclosure, a method of providing a virtual image may include photographing a retina image, calculating a focal length of the crystalline lens based on information on the photographed retina image, determined viewing distance information based on the calculated focal length of the crystalline lens, and displaying the virtual image by adjusting a location or refractive power of the variable lens based on the determined viewing distance information.

According to various embodiments of the present disclosure, a method of providing a virtual image by a wearable device including a projection type display unit may include projecting an illumination light to eye of a user through an illumination unit (or the projection type display unit), detecting a light reflected from the eye (or retina of the eye), acquiring viewing distance information related to a viewing point (or focus) of the eye based on the retina image information with respected to the detected light, and displaying the virtual image on the actual view through the projection type display unit to place the virtual image at a distance corresponding to the viewing point (or the viewing distance information).

According to various embodiments of the present disclosure, a method of providing a virtual image by a wearable device including a projection type display unit may include projecting an illumination light to eye of a user through an illumination unit, detecting a light reflected from the eye (or retina of the eye) through a light receiving unit, adjusting a location or refractive power of a variable lens within the projection type display unit based on retina image information with respect to the detected light, and displaying the virtual image through a control of the projection type display unit.

According to various embodiments of the present disclosure, a method of providing a virtual image by a wearable device including a projection type display unit may include projecting an illumination light to eye of a user, detecting a light reflected from the eye (or retina of the eye), acquiring viewing distance information related to a viewing point (or focus) of the eye based on retina image information with respect to the detected light, and displaying the virtual image (or first or second virtual image) on the actual view through the projection type display unit to place the virtual image at a distance corresponding to the viewing distance information.

According to various embodiments of the present disclosure, a method of providing a virtual image by a wearable device including a projection type display unit may include displaying a first virtual image on an actual view in the front of the wearable device through the projection type display unit, projecting an illumination light to eye of a user, detecting a light reflected from the eye (or retina of the eye), adjusting a location or refractive power of a variable lens within the projection type display unit based on retina image information with respect to the detected light, and displaying a second virtual image at a location farther or closer than a location of the first virtual image through a control of the projection type display unit.

According to various embodiments of the present disclosure, the retina image information may include at least one piece of pixel information on an ISP sensor or an image sensor, retina image size information, area information, location information, pattern information, and brightness (or brightness distribution) information on the retina image. For example, each piece of the information may include a corresponding value, a corresponding range, or a corresponding level.

According to various embodiments of the present disclosure, the viewing distance information may include at least one piece of distance measurement information using a third sensor (for example, the third sensor 193), object distance information calculated based on focal distance information on the crystalline lens, size information on the retina reflective surface (that is, some areas of the retina where the illumination light is incident and reflected) calculated based on the retina image information (that is, defocus size), magnification information, refractive power information, curvature (or radius of curvature) information, and thickness information on the crystalline lens. For example, each piece of the information may include a corresponding value, a corresponding range, or a corresponding level.

According to various embodiments of the present disclosure, the acquiring of the viewing distance information may include determining the viewing distance information corresponding to the retina image information based on a table (or database) pre-stored in the wearable device.

According to various embodiments of the present disclosure, the acquiring of the viewing distance information may include determining the viewing distance information corresponding to the retina image information based on the table (or database) pre-stored in the wearable device.

According to various embodiments of the present disclosure, the acquiring of the viewing distance information may include detecting first values corresponding to the retina image information in the table (or database) pre-stored in the wearable device, and calculating the viewing distance information from second values of the table corresponding to the first values.

According to various embodiments of the present disclosure, the method may further include displaying a third virtual image on the actual view in the front of the wearable device through the projection type display unit, projecting a second illumination light to eye of a user, detecting a light reflected from the eye (or retina of the eye), and changing the table (or database) pre-stored in the wearable device, which indicates a correspondence relation between the retina image information and the viewing distance information based on information on the detected light.

According to an embodiment of the present disclosure, based on the table (or database) pre-stored in the wearable device, control information on the variable lens corresponding to the retina image information or the viewing distance information related to the retina image information and the viewing point (or focus) of the eye may be determined.

According to an embodiment of the present disclosure, control information on the variable lens corresponding to the retina image information or the viewing distance information related to the retina image information and the viewing point (or focus) of the eye may be detected in the table (or database) pre-stored in the wearable device.

According to various embodiments of the present disclosure, the wearable device may include a first sensor that outputs the illumination light and detects the reflected light.

According to various embodiments of the present disclosure, the projection type display unit may include a display element that outputs a first light forming the virtual image (or first or second virtual image), a variable lens disposed on a progress path of the first light and configured to adjust a location or refractive power according to a control signal, a first sensor that outputs the illumination light and detects the reflected light, and a light guide element that projects the first light output from the display element onto the eye, projects the illumination light output from the first sensor onto the eye, and outputs the reflected light to the first sensor.

According to various embodiments of the present disclosure, the first sensor may include an illumination unit (or light source) that outputs the illumination light, a lens that forms an image of the reflected light, and a light receiving unit (or image sensor) that detects an image of the reflected light. According to an embodiment of the present disclosure, the lens may be included in the light receiving unit.

According to various embodiments of the present disclosure, the first sensor may include an illumination unit (or light source) that outputs the illumination light, a first beam splitter that outputs the illumination light to the light guide unit and outputs the reflected light received from the light guide element to a lens, and the lens that forms an image of the reflected light, and a light receiving unit (or image sensor) that detects the image of the reflected light.

According to various embodiments of the present disclosure, the first sensor may further include a third beam splitter that projects the illumination light received from the first beam splitter, projects a second light forming the actual view onto the eye, and outputs the reflected light to the first beam splitter.

According to various embodiments of the present disclosure, the light guide element may include a second beam splitter that outputs the first light output from the display element and the illumination light output from the illumination unit (or first sensor) to the third beam splitter and outputs the reflected light received from the third beam splitter to the light receiving unit (or first sensor), and the third beam splitter that projects the first light and the illumination light received from the second beam splitter onto the eye, projects the second light forming the actual view onto the eye, and outputs the reflected light to the second beam splitter.

According to various embodiments of the present disclosure, a method of providing a virtual image by a wearable device including a projection type display unit may include displaying a first virtual image on the actual view in the front of the wearable device through the projection type display unit, adjusting a location or refractive power of a variable lens within the projection type display unit, and displaying a second virtual image at a location farther or closer than a location of the first virtual image through the projection type display unit.

According to various embodiments of the present disclosure, a method of providing a virtual image by a wearable device may include acquiring information on a location of an eye feature point and/or information on a tilt of the wearable device, acquiring information on a distance between a preset reference point and a viewing point of the actual view based on the information on the location of the feature point and/or the information on the tilt of the wearable device, and displaying a virtual image on the actual view to place the virtual image at a virtual object distance corresponding to the information on the distance.

According to various embodiments of the present disclosure, each piece of the information on the location of the feature point and the information on the distance may include a corresponding value or a corresponding range.

According to various embodiments of the present disclosure, the information on the location may be acquired based on one of preset different location ranges of the eye.

According to various embodiments of the present disclosure, the acquiring of the information on the location may include acquiring, as the information on the location of the feature, a location range including the feature point among the preset different location ranges of the eye or a particular location within the location range.

According to various embodiments of the present disclosure, the information on the location may include a location on a preset axis of the eye.

According to various embodiments of the present disclosure, the information on the distance may be acquired based on one of the preset different distance ranges of the eye.

According to various embodiments of the present disclosure, the information on the distance may be acquired based on one of the preset different distance ranges and the different distance ranges may include at least two of a first distance range, a second distance range farther and/or wider than the first distance range, and a third distance range farther and/or wider than the second distance range.

According to various embodiments of the present disclosure, the information on the distance may include a distance on a preset axis.

According to various embodiments of the present disclosure, the acquiring of the information on the distance may include acquiring, as the information on the distance, a distance range corresponding to the information on the location of the feature point among the preset different distance ranges or a particular location within the distance range.

According to various embodiments of the present disclosure, the method may further include determining whether the location of the feature point is fixed for a preset threshold time, wherein, when the location of the feature point is fixed for the preset threshold time, the acquiring of the information on the distance may be initiated.

According to various embodiments of the present disclosure, the information on the distance may be acquired based on the information on the location of the feature point and the information on the tilt.

According to various embodiments of the present disclosure, the acquiring of the information on the distance may include acquiring, as the information on the distance, a distance range corresponding to the information on the tilt and the information on the location of the feature point among the preset different distance ranges or a particular location within the distance range.

According to various embodiments of the present disclosure, the acquiring of the information on the distance may include determining a first distance range corresponding to the information on the tilt among the preset different distance ranges, and acquiring, the information on the distance, a second distance rage corresponding to the information on the location of the feature point among preset different distance ranges within the first distance range or a particular location within the second distance range.

According to various embodiments of the present disclosure, the method may further include measuring a distance between a preset reference point and at least one object within the actual view by using a sensor of the wearable device, wherein the information on the distance may be acquired based on the information on the location of the feature point and the measured distance.

According to various embodiments of the present disclosure, the method may further include measuring a distance between a preset reference point and an actual object within the actual view by using a sensor of the wearable device, wherein the acquiring of the information on the distance may include determining a distance range corresponding to the information on the location of the feature point among the preset different distance ranges, determining whether the measured distance belongs to the determined distance range, acquiring the measured distance as the information on the distance when the measured distance belongs to the determined distance range, and acquiring, as the information on the distance, the determined distance range or a particular location within the determined distance range when the measured distance does not belong to the determined distance range.

According to various embodiments of the present disclosure, the method may further include measuring distances between the preset reference point and actual objects within the actual view by using a sensor of the wearable device, wherein the acquiring of the information on the distance may include determining a distance range corresponding to the information on the location of the feature point among the preset different distance ranges, and acquiring, as the information on the distance, a distance belonging to the determined distance range among the measured distances.

According to various embodiments of the present disclosure, the method may further include measuring a distance between the preset reference point and the actual object within the actual view by using a sensor of the wearable device, wherein the information on the distance may be acquired based on the information on the location of the feature point and the information on the tilt.

According to various embodiments of the present disclosure, the method may further include measuring a distance between the preset reference point and the actual object within the actual view by using a sensor of the wearable device, wherein the acquiring of the information on the distance may include determining a distance range corresponding to the information on the tilt and the information on the location of the feature point among the preset different distance ranges, determining whether the measured distance belongs to the determined distance range, acquiring the measured distance as the information on the distance when the measured distance belongs to the determined distance range, and acquiring, as the information on the distance, the determined distance range or a particular location within the determined distance range when the measured distance does not belong to the determined distance range.

According to various embodiments of the present disclosure, the method may further include measuring distances between the preset reference point and actual objects within the actual view by using a sensor of the wearable device, wherein the acquiring of the information on the distance may include determining a distance range corresponding to the information on the tilt and the information on the location of the feature point among the preset different distance ranges, and acquiring, as the information on the distance, a distance belonging to the determined distance range among the measured distances.

According to various embodiments of the present disclosure, the displaying of the virtual image may include adjusting a location or refractive power of a variable lens within the projection type display unit to allow an image displayed by the projection type display unit within the wearable device to have the virtual object distance, and controlling the projection type display unit to project a light forming the virtual image to be located at the virtual object distance.

According to various embodiments of the present disclosure, the wearable device may include a projection type display unit that includes a variable lens and projects a light forming an image, a first sensor that detects a light reflected from an eye of a user (or a wearer), and a processor that controls the projection type display unit to display a virtual image by controlling one of a location of the variable lens and refractive power of the variable lens based on retina image information corresponding to the detected light.

According to various embodiments of the present disclosure, the wearable device may include a projection type display unit configured to project a light forming an image, and a processor configured to display a first virtual image on the actual view in the front of the wearable device through the projection type display unit, adjust a location or refractive power of a variable lens within the projection type display unit, and displaying a second virtual image at a location farther or closer than a location of the first virtual image through the projection type display unit.

According to various embodiments of the present disclosure, the wearable device may include a sensor module, a projection type display unit configured to project a light forming an image, and a processor configured to acquire information on a location of an eye feature point and/or information on a tilt of the wearable device using the sensor module, acquire information on a distance between a preset reference point and a viewing point of the actual view based on the information on the location of the feature point and/or the information on the tilt of the wearable device, and display a virtual image on the actual view to place the virtual image at a virtual object distance corresponding to the information on the distance using the projection type display unit.

According to various embodiments of the present disclosure, the processor may be configured to acquire, as the information on the location of the feature, a location range including the feature point among the preset different location ranges of the eye or a particular location within the location range.

According to various embodiments of the present disclosure, the processor may be configured to acquire, as the information on the distance, a distance range corresponding to the information on the location of the feature point among the preset different distance ranges or a particular location within the distance range.

According to various embodiments of the present disclosure, the processor may be configured to determine whether the location of the feature point is fixed for a preset threshold time, and, when the location of the feature point is fixed for the preset threshold time, initiate an operation for acquiring the information on the distance.

According to various embodiments of the present disclosure, the processor may be configured to acquire the information on the location of the feature point through a first sensor of the sensor module and acquire the information on the tilt of the wearable device through a second sensor of the sensor module.

According to various embodiments of the present disclosure, the processor may be configured to acquire, as the information on the distance, a distance range corresponding to the information on the tilt and the information on the location of the feature point among the preset different distance ranges or a particular location within the distance range.

According to various embodiments of the present disclosure, the processor may be configured to determine a first distance range corresponding to the information on the tilt among the preset different distance ranges, and acquire, the information on the distance, a second distance rage corresponding to the information on the location of the feature point among preset different distance ranges within the first distance range or a particular location within the second distance range.

According to various embodiments of the present disclosure, the processor may be configured to measure a distance between a preset reference point and at least one object within the actual view through a third sensor of the sensor module.

According to various embodiments of the present disclosure, the processor may be configured to determine a distance range corresponding to the information on the location of the feature point among the preset different distance ranges, determine whether the measured distance belongs to the determined distance range, acquire the measured distance as the information on the distance when the measured distance belongs to the determined distance range, and acquire, as the information on the distance, the determined distance range or a particular location within the determined distance range when the measured distance does not belong to the determined distance range.

According to various embodiments of the present disclosure, the processor may be configured to determine a distance range corresponding to the information on the location of the feature among the preset different distance ranges and acquire, as the information on the distance, a distance belonging to the determined distance range among the measured distance ranges.

According to various embodiments of the present disclosure, the processor may be configured to determine a distance range corresponding to the information on the tilt and the information on the location of the feature point among the preset different distance ranges, determine whether the distance measured by the sensor module belongs to the determined distance range, acquire the measured distance as the information on the distance when the measured distance belongs to the determined distance range, and acquire, as the information on the distance, the determined distance range or a particular location within the determined distance range when the measured distance does not belong to the determined distance range.

According to various embodiments of the present disclosure, the processor may be configured to determine a distance range corresponding to the information on the tilt and the information on the location of the feature among the preset different distance ranges and acquire, as the information on the distance, a distance belonging to the determined distance range among the measured distances.

According to various embodiments of the present disclosure, the processor may be configured to adjust a location or refractive power of a variable lens within the projection type display unit to allow an image displayed by the projection type display unit to have the virtual object distance and control the projection type display unit to project a light forming the virtual image to be located at the virtual object distance.

According to various embodiments of the present disclosure, the projection type display unit may include a display element that outputs a light forming the image, a light guide element that projects the light output from the display element onto the eye, and a variable lens that is disposed on a progress path of the light and adjusts a location or refractive power according to a control signal.

According to various embodiments of the present disclosure, a refraction surface of the variable lens faces an end of the light guide element, and form of the refraction surface may change according to the control signal.

According to various embodiments of the present disclosure, the variable lens may be disposed between the display element and the light guide element, a form of the variable lens may change according to the control signal, and the light having passed through the variable lens may be coupled into the light guide element.

According to various embodiments of the present disclosure, the variable lens may be disposed within the light guide element, the form of the variable lens may change according to the control signal, and the light progressing inside the light guide element may penetrate the variable lens.

According to various embodiments of the present disclosure, the variable lens may be disposed between the display element and the light guide element, a location of the variable lens may change according to the control signal, and the light having passed through the variable lens may be coupled into the light guide element.

According to various embodiments of the present disclosure, the variable lens may be disposed within the light guide element, the location of the variable lens may change according to the control signal, and the light progressing inside the light guide element may penetrate the variable lens.

According to various embodiments of the present disclosure, the wearable device may include a projection type display unit configured to project a light forming an image, and a processor configured to project an illumination light onto an eye of a user, detect a light reflected from the eye (or retina of the eye), acquire viewing distance information related to a viewing point (or focus) of the eye based on retina image information with respect to the detected light, and display the virtual image (or first or second virtual image) on the actual view through the projection type display unit to place the virtual image at a distance corresponding to the viewing distance information.

According to various embodiments of the present disclosure, the wearable device may include a projection type display unit configured to project a light forming an image, and a processor configured to project an illumination light onto an eye of a user through an illumination unit (or first sensor), detect a light reflected from the eye (or retina of the eye) through a light receiving unit, acquire viewing distance information related to a viewing point (or focus) of the eye based on retina image information with respect to the detected light, and display the virtual image (or first or second virtual image) on the actual view through the projection type display unit to place the virtual image at a distance corresponding to the viewing distance information.

According to various embodiments of the present disclosure, the wearable device may include a projection type display unit configured to project a light forming an image, and a processor configured to display a first virtual image on the actual view in the front of the wearable device through the projection type display unit, project an illumination light onto an eye of a user through the projection type display unit, detect a light reflected from the eye (or retina of the eye) through the projection type display unit, adjust a location or refractive power of a variable lens within the projection type display unit based on retina image information with respect to the detected light, and display a second virtual image at a location farther or closer than a location of the first virtual image through the projection type display unit.

According to various embodiments of the present disclosure, the wearable device may include a projection type display unit configured to project a light forming an image, an illumination unit (or first sensor) configured to generate an illumination light, and a processor configured to display a first virtual image on the actual view in the front of the wearable device through the projection type display unit, project an illumination light onto an eye of a user through the illumination unit (or first sensor), detect a light reflected from the eye (or retina of the eye) through the illumination unit (or first sensor), adjust a location or refractive power of a variable lens within the projection type display unit based on retina image information with respect to the detected light, and display a second virtual image at a location farther or closer than a location of the first virtual image through the projection type display unit.

According to various embodiments of the present disclosure, the retina image information may include at least one piece of size information, area information, location information, pattern information, and brightness (or brightness distribution) information on an image of the detected light. For example, each piece of the information may include a corresponding value, a corresponding range, or a corresponding level.

According to various embodiments of the present disclosure, the viewing distance information may include at least one piece of distance measurement information using a third sensor (for example, the third sensor 193), object distance information calculated based on focal distance information on the crystalline lens, size information on the retina reflective surface (that is, some areas of the retina where the illumination light is incident and reflected) calculated based on the retina image information (that is, defocus size), magnification information, refractive power information, curvature (or radius of curvature) information, and thickness information on the crystalline lens. For example, each piece of the information may include a corresponding value, a corresponding range, or a corresponding level.

According to various embodiments of the present disclosure, the processor may be configured to acquire retina image information by receiving a light which is reflected from a retina as the radiated light passes through a crystalline lens, calculate a focal length of the crystalline lens based on the acquired retina image information, and determine a viewing distance of the user based on the calculated focal length.

According to various embodiments of the present disclosure, the processor may be configured to display a first virtual image on a front actual view through the projection type display unit, adjust a location or refractive power of the variable lens based on the retina image information with respect to the detected light, and display a second image at a location farther or closer than a location of the first image through the projection type display unit.

According to various embodiments of the present disclosure, the processor may be configured to determine the viewing distance information corresponding to the retina image information based on the table (or database) pre-stored in the wearable device.

According to an embodiment of the present disclosure, the processor may be configured to detect the viewing distance information corresponding to the retina image information in the table (or database) pre-stored in the wearable device.

According to various embodiments of the present disclosure, the processor may be configured to detect first values corresponding to the retina image information in the table (or database) pre-stored in the wearable device and calculate the viewing distance information from second values of the table corresponding to the first values.

According to various embodiments of the present disclosure, the processor may be configured to display a third virtual image on the actual view in the front of the wearable device through the projection type display unit, project a second illumination light onto the eye of the user through the projection type display unit or the illumination unit (or first sensor), detect a right reflected from the eye (or retina or the eye) through the projection type display unit or the light receiving unit (or first sensor), and change the table (or database) pre-stored in the wearable device, which indicates a correspondence relation between the retina image information and the viewing distance information.

According to various embodiments of the present disclosure, the processor may be configured to determine control information on the variable lens corresponding to the retina image information or the viewing distance information related to the retina image information and the viewing point (or focus) of the eye based on the table (or database) pre-stored in the wearable device.

According to various embodiments of the present disclosure, the processor may be configured to detect control information on the variable lens corresponding to the retina image information or the viewing distance information related to the retina image information and the viewing point (or focus) of the eye may be detected in the table (or database) pre-stored in the wearable device.

According to various embodiments of the present disclosure, the wearable device may include a first sensor that outputs the illumination light and detects the reflected light.

According to various embodiments of the present disclosure, the projection type display unit may include a display element that outputs a first light forming the virtual image (or first or second virtual image), a variable lens disposed on a progress path of the first light and configured to adjust a location or refractive power according to a control signal, a first sensor configured to output the illumination light and detect a reflected light, and a light guide element configured to project the first light output from the display element onto the eye, project the illumination light output from the first sensor onto the eye, and output the reflected light to the first sensor.

According to various embodiments of the present disclosure, the first sensor may include an illumination unit (or light source) configured to output the illumination light, a lens configured to form an image of the reflected light, and a light receiving unit (or image sensor) configured to detect the image of the reflected light.

According to various embodiments of the present disclosure, the first sensor may include an illumination unit (or light source) configured to output the illumination light, a first beam splitter configured to output the illumination light to the light guide unit and output the reflected light received from the light guide element to a lens, and the lens configured to form an image of the reflected light, and a light receiving unit (or image sensor) configured to detect the image of the reflected light.

According to various embodiments of the present disclosure, the first sensor may further include a third beam splitter configured to project the illumination light received from the first beam splitter onto the eye, project a second light forming the actual view onto the eye, and output the reflected light to the first beam splitter.

According to various embodiments of the present disclosure, the light guide element may include a second beam splitter configured to output the first light output from the display element and the illumination light output from the illumination unit (or first sensor) to the third beam splitter and output the reflected light received from the third beam splitter to the light receiving unit (or first sensor), and the third beam splitter configured to project the first light and the illumination light received from the second beam splitter onto the eye, project the second light forming the actual view onto the eye, and output the reflected light to the second beam splitter.

The above described components of the electronic device according to various embodiments of the present disclosure may be formed of one or more components, and a name of a corresponding component element may be changed based on the type of electronic device. The electronic device according to the present disclosure may include one or more of the aforementioned components or may further include other additional components, or some of the aforementioned components may be omitted. Further, some of the components of the electronic device according to the various embodiments of the present disclosure may be combined to form a single entity, and thus, may equivalently execute functions of the corresponding elements prior to the combination.

The "module" used in various embodiments of the present disclosure may refer to, for example, a "unit" including one of hardware, software, and firmware, or a combination of two or more of the hardware, software, and firmware. The "module" may be interchangeably used with a term, such as unit, logic, logical block, component, circuit, and the like. The "module" may be the smallest unit of an integrated component or a part thereof. The "module" may be the smallest unit that performs one or more functions or a part thereof. The "module" may be mechanically or electronically implemented. For example, the "module" according to various embodiments of the present disclosure may include at least one of an application-specific integrated circuit (ASIC) chip, a field-programmable gate arrays (FPGAs), and a programmable-logic device for performing operations which have been known or are to be developed hereafter.

According to various embodiments of the present disclosure, at least a part of a device (for example, modules or functions thereof) or a method (for example, operations) according to the various embodiments of the present disclosure may be embodied by, for example, a command stored in a computer readable storage medium in a form of a programming module. When the command is executed by one or more processors (for example, the processor 120), the one or more processors may execute a function corresponding to the command. The computer-readable storage medium may be, for example, the memory 130. At least some of the programming modules may be implemented (for example, executed) by, for example, the processor 120. At least some of the programming modules may include, for example, a module, a program, a routine, a set of instructions or a process for performing one or more functions.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a Read-Only Memory (ROM), a Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

A module or a programming module according to the present disclosure may include at least one of the described component elements, a few of the component elements may be omitted, or additional component elements may be included. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

According to various embodiments of the present disclosure, a storage medium storing commands is provided. The commands are configured to allow one or more processors to perform one or more operations when being executed by the one or more processors. The one or more operations may include displaying a first virtual image on an actual view in the front of the wearable device through a projection type display unit, adjusting a location or refractive power of a variable lens within the projection type display unit, and displaying a second virtual image at a location farther or closer than a location of the first virtual image through the projection type display unit.

According to various embodiments of the present disclosure, a storage medium storing commands is provided. The commands are configured to allow one or more processors to perform one or more operations when being executed by the one or more processors. The one or more operations may include acquiring information on a location of an eye feature point and/or information on a tilt of the wearable device, acquiring information on a distance between a preset reference point and a viewing point of the actual view based on the information on the location of the feature point and/or the information on the tilt of the wearable, and displaying a virtual image on the actual view to place the virtual image at a virtual object display corresponding to the information on the distance.

According to various embodiments of the present disclosure, a storage medium storing commands is provided. The commands are configured to allow one or more processors to perform one or more operations when being executed by the one or more processors. The one or more operations may include projecting an illumination light onto an eye of a user, detecting a light reflected from the eye (or retina or the eye), acquiring viewing distance information related to a viewing point (or focus) of the eye based on retina image information with respect to the detected light, and displaying a virtual image (or first or second virtual image) on the actual view through the projection type display unit to place the virtual image at a distance corresponding to the viewing distance information.

According to various embodiments of the present disclosure, a storage medium storing commands is provided. The commands are configured to allow one or more processors to perform one or more operations when being executed by the one or more processors. The one or more operations may include displaying a first virtual image on an actual view in the front of the wearable device through a projection type display unit, projecting an illumination light to an eye of a user, detecting a light reflected from the eye (or retina of the eye), adjusting a location or refractive power of a variable lens within the projection type display unit based on retina image information with respected to the detected light, and displaying a second virtual image at a location farther or closer than a location of the first virtual image through the projection type display unit through a control of the projection type display unit.

According to various embodiments of the present disclosure, a storage medium storing commands is provided. The commands are configured to allow one or more processors to perform one or more operations when being executed by the one or more processors. The one or more operations may include displaying a first virtual image on an actual view in the front of the wearable device through a projection type display unit, adjusting a location or refractive power of a variable lens within the projection type display unit by controlling the projection type display unit, and displaying a second virtual image at a location farther or closer than a location of the first virtual image through a control of the projection type display unit.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method of outputting a virtual image by a wearable device, the method comprising:
radiating a first light to an eye of a user wearing the wearable device;
acquiring eye information related to a viewing point of the eye by detecting a second light which is reflected from the eye based on the first light;
acquiring tilt information on a tilt of the wearable device by using a sensor of the wearable device;

identifying a viewing distance of the user based on the eye information and the tilt information; and displaying the virtual image on an actual view by using a projection type display based on the viewing distance of the user.

2. The method of claim 1, wherein the displaying of the virtual image on the actual view comprises displaying the virtual image at a point of the actual view corresponding to the viewing point of the eye.

3. The method of claim 1, further comprising changing a table comprising the eye information related to the viewing point of the eye.

4. The method of claim 1, further comprising:
radiating a third light to the eye of the user wearing the wearable device;
changing the eye information related to the viewing point of the eye by detecting a fourth light which is reflected from the eye; and
displaying another virtual image at another point of the actual view different from a point at which the virtual image is displayed by using the projection type display based on the changed eye information.

5. The method of claim 4, further comprising adjusting a location or refractive power of a variable lens within the projection type display.

6. The method of claim 1, wherein the eye information comprises information regarding to one piece of pixel on an image signal processor (ISP) sensor, size information of the eye, area information of the eye, location information of the eye, pattern information of the eye, or brightness information of the eye.

7. The method of claim 1,
wherein the viewing distance is identified based on focal length information on a crystalline lens of the eye, retina reflection surface size information on the crystalline lens, magnification information on the crystalline lens, refractive power information on the crystalline lens, curvature information on the crystalline lens, or thickness information on the crystalline lens.

8. The method of claim 1, further comprising:
detecting ambient illumination through an illumination sensor;
identifying a pupil size based on the ambient illumination, and
identifying a focal length of a crystalline lens of the eye based on the pupil size and the eye information.

9. A wearable device comprising:
a projection type display comprising a variable lens, and configured to project a light forming an image;
a first sensor configured to detect a light reflected from an eye of a user wearing the wearable device based on the projected light;
a second sensor configured to detect a tilt of the wearable device; and
at least one processor configured to:
acquire eye information related to a viewing point of the eye based on the light detected by using the first sensor,
acquire tilt information on the tilt of the wearable device by using the second sensor,
identify a viewing distance of the user based on the eye information and the tilt information, and
control the projection type display to display a virtual image by controlling one of a location of the variable lens or a refractive power of the variable lens based on the viewing distance.

10. The wearable device of claim 9, wherein, to control the projection type display to display the virtual image, the at least one processor is further configured to control the projection type display to display the virtual image at a point of an actual view corresponding to the viewing point of the eye.

11. The wearable device of claim 9, wherein the at least one processor is further configured to change a table comprising the eye information related to the viewing point of the eye.

12. The wearable device of claim 9,
wherein the first sensor is further configured to detect another light reflected from the eye, and
wherein the at least one processor is further configured to:
change the eye information related to the viewing point of the eye based on the other light detected from the first sensor, and
control the projection type display to display another virtual image at another point different from a point at which the virtual image is displayed based on the changed eye information.

13. The wearable device of claim 9, wherein the eye information comprises information regarding to one piece of pixel on an image signal processor (ISP) sensor, size information of the eye, area information of the eye, location information of the eye, pattern information of the eye, or brightness information of the eye.

14. The wearable device of claim 9,
wherein the viewing distance is identified based on focal length information on a crystalline lens of the eye, retina reflection surface size information on the crystalline lens, magnification information on the crystalline lens, refractive power information on the crystalline lens, curvature information on the crystalline lens, or thickness information on the crystalline lens.

15. The wearable device of claim 9, wherein the projection type display further comprises:
a display element configured to output a first light forming the virtual image, the variable lens being disposed on a progress path of the first light, and configured to adjust a location or a refractive power according to a control signal;
a light source configured to output an illumination light;
a light receiver configured to detect the reflected light; and
a light guide element configured to:
project the first light output from the display element onto a retina,
project the illumination light output from the light source onto the retina, and
output the reflected light to the light receiver.

16. The wearable device of claim 15,
wherein the projection type display further comprises a lens configured to form an image of the reflected light, and
wherein the light receiver is configured to detect the image of the reflected light.

17. The wearable device of claim 16, wherein the projection type display further comprises a first beam splitter configured to:
output the illumination light to the light guide element, and
output the reflected light received from the light guide element to the lens.

18. The wearable device of claim 15,
wherein the light guide element comprises:
a second beam splitter; and
a third beam splitter, wherein the second beam splitter is configured to:
output the first light output from the display element and the illumination light output from the light source to the third beam splitter, and
output the reflected light input from the third beam splitter to the light receiver, and wherein the third beam splitter is configured to:
project the first light and the illumination light received from the second beam splitter on the retina,
project a second light forming an actual view onto the retina, and
output the reflected light to the second beam splitter.

19. At least one non-transitory computer readable storage medium for storing a computer program comprising instructions configured to be readable by at least one processor for configuring the at least one processor to execute a computer process for performing the method of claim 1.

* * * * *